United States Patent [19]
Jessell et al.

[11] Patent Number: 5,750,502
[45] Date of Patent: May 12, 1998

[54] CLONING, EXPRESSION AND USES OF A SECRETED PROTEIN, F-SPONDIN

[75] Inventors: Thomas M. Jessell, New York, N.Y.; Avihu Klar, Jerusalem, Israel

[73] Assignee: The Trustees of Columbia University in City of New York, New York, N.Y.

[21] Appl. No.: 313,288

[22] PCT Filed: Apr. 2, 1993

[86] PCT No.: PCT/US93/03164

§ 371 Date: Jan. 5, 1995

§ 102(e) Date: Jan. 5, 1995

[87] PCT Pub. No.: WO93/20196

PCT Pub. Date: Oct. 14, 1993

Related U.S. Application Data

[63] Continuation-in-part of Ser. No. 862,021, Apr. 2, 1992, Pat. No. 5,279,966.

[51] Int. Cl.$^6$ .................................................. A61K 38/16
[52] U.S. Cl. .......................... 514/12; 435/69.1; 530/350
[58] Field of Search .............................. 435/69.1, 252.3, 435/240.2, 325, 320.1; 514/2, 12; 530/350, 412

[56] References Cited

PUBLICATIONS

Frazier, W.A., "Thrombospondin: a Molecular Adhesive Glycoprotein of Platelets and Nucleated Cells", J. Cell. Biol., vol. 105, Aug. 1987, pp. 625–632.

Henderson C.E., et al., "Neurite Outgrowth from Embryonic Chicken Spinal Neurons is Promoted by Media Conditioned by Muscle Cells", Proceedings of the National Academy of Sciences USA, vol. 78, No. 4, Apr. 1981, pp. 2625–2629.

Jacobson, M., "The Germinal Cell, Histogenesis, and Lineages of Nerve Cells", 1991 Developmental Neurobiology, (3rd Edition) Plenum Press—New York & London, pp. 41–93.

Jessell, T.M. and Dodd, J., "Floor Plate–Derived Signals and the Control of Neural Cell Pattern in Vertebrates", 1992, The Harvey Lectures, Series 86, pp. 87–128.

Jessell, T.M. and Dodd, J., "Cell Differentiation, Axon Guidance, and Target Recognition in Vertebrate Neural Development: A Brief Overview", (1991), Neurodegenerative Disorders: Mechanisms and Prospects for Therapy, pp. 105–126.

Klar A., et al., "F–Spondin: a Gene Expressed at High–Levels in the Floor Plate Encodes a Secreted Protein That Promotes Neural Cell Adhesion and Neurite Extension", Cell, vol. 69, Apr. 3, 1992, pp. 95–110.

Kosfeld M.D. et al., "Cell Attachment Activity of the Carboxy–Terminal Domain of Human Thrombospondin Expressed in *Escherichia coli*", J. Biol. Chem., vol. 266, No. 36, Dec. 25, 1991, pp. 24257–24259.

O'Shea K.S. et al., "Thrombospondin and a 140Kd Fragment Promote Adhesion and Neurite Outgrowth from Embryonic Central and Peripheral Neurons and from PC12 Cells", Neuron, vol. 7, Aug. 1991, pp. 231–237.

Osterhout D.J., et al., "Thrombospondin Promotes Process Outgrowth in Neurons from the Peripheral and Central Nervous Systems", Development Biology, vol. 150, 1992, pp. 256–265.

Placzek M. et al., "Mesodermal Control of Neural Cell Identity: Floor Plate Induction by the Notochord", Science, vol. 250, Nov. 16, 1990, pp. 985–988.

Sigma Catalog, 1989, p. 116.

*Primary Examiner*—John Ulm
*Assistant Examiner*—Karen E. Brown
*Attorney, Agent, or Firm*—John P. White

[57] ABSTRACT

This invention provides an isolated vertebrate nucleic acid molecule encoding F-spondin. This invention also provides a probe comprising a nucleic acid molecule of at least 15 nucleotides capable of specifically hybridizing with a sequence included within the sequence of a nucleic acid molecule encoding an F-spondin. This invention further provides a method of attaching nerve cells to a matrix comprising contacting the matrix with nerve cells and purified F-spondin at a concentration effective to effect attachment of the cells to the matrix. This invention also provides a method of stimulating growth of a nerve cell comprising contacting the nerve cell with purified F-spondin at a concentration effective to stimulate growth of the nerve cell. This invention provides a method of regenerating nerve cells in a subject comprising administering to the subject purified F-spondin at a concentration effective to regenerate nerve cells in the subject. Finally, this invention provides a pharmaceutical composition comprising a pharmaceutically acceptable carrier and purified F-spondin.

6 Claims, 22 Drawing Sheets

Floor plate induction by the notochord

Control of D-V cell pattern by the floor plate

Chemotropic guidance of commissural axons by the floor plate

Contact-dependent guidance of commissural axons by the floor plate

FIGURE 5A

```
CCCTCCCCTCTCTTCGGCGCTCCTTCGCACCGCCCGCCCCTCAGCTTCCGCTGCTCCGCTGCTCCGC
TCAGAGCAGGCCAGCTCCGCAGCCAAAGCGAGGCGGGCTCGGGCTCCGGCTCCCCACCGCCAGTGC
CACCCGGGCTCCTCCTCCAGCTTTCGCTCTGCTCCGTCCCGTCACTTGGAGTAAAAGTGTCCT
GACAGGGTCTGCAACATCAGCAGAAAGTTGGGAGTCCTCGAGAATGAGGCTATCTCCC
                                        M  R  L  S  P
GCGCCCCCTGAGGCTTAGCCGGGGTCCCGGCCCTGGCCCTGGCGCTGCCCCTGGCCCGCA
 A  P  L  R  L  S  R  G  P  A  L  L  A  L  A  L  P  L  A  A
GCGGTCGCTTTCTCGGATGAGACCCTGGACAAAGTGGCCAAGTCGGAGGGCTACTGCAGC
 A  L  A  F  S  D  E  T  L  D  K  V  A  K  S  E  G  Y  C  S
CGCATCTTGCGCGCCCAGGGCACACGGCGTGAGGGATACACAGAGTTCAGCCTCCGCGTG
 R  I  L  R  A  Q  G  T  R  R  E  G  Y  T  E  F  S  L  R  V
GAAGGGCGACCCTGACTTCTATAAGCCAGGAAGCAGCTACCGAGTGACACTCTCGGCTGCC
 E  G  D  P  D  F  Y  K  P  G  S  S  Y  R  V  T  L  S  A  A
CCTCCCCTACTTCAGAGGCTTCACGTTAATTGCTCTCAAAGAGAACCGCGAAGGCGAT
 P  P  S  Y  F  R  G  F  T  L  I  A  L  K  E  N  R  E  G  D
AAGGAAGAAGAACCACGCGGGCACCTTCCAGATCATAGATGAAGAAACCCAGTTTATG
 K  E  E  D  H  A  G  T  F  Q  I  I  D  E  E  E  T  Q  F  M
AGTAACTGTCCTGTGGCAGTCACTGAAGCACCCCTCGAGGAGGACACGGATCCAGGTG
 S  N  C  P  V  A  V  T  E  S  T  P  R  R  R  T  R  I  Q  V
TTTTGGATAGCGCCACCCACCAGGACAGGCTGTGTGATTCTGAAGGCCAGCATTGTACAG
 F  W  I  A  P  P  T  G  T  G  C  V  I  L  K  A  S  I  V  Q
AAACGCATTATCTATTTCAAGACGGAAGCGGACCTCTTAGACTTGCTGCCTGAACAGGAT
 K  R  I  I  Y  F  Q  D  E  G  S  L  T  K  K  L  C  E  Q  D
CCCACACTTGATGGAGTTACGGACCGATCTTAGACTTAGACTGCGCCCTGCGCCGGAACTGCC
 P  T  L  D  G  V  T  D  R  P  I  L  D  C  C  A  C  G  T  A
AAGTACAGACTCACGTTTTATGGAACTGGTCGGAGAAGACTCATCCAAAGGATTACCCT
 K  Y  R  L  T  F  Y  G  N  W  S  E  K  T  H  P  K  D  Y  P
```

FIGURE 5B

```
CGTCGGGCTAATCACTGGTCTCTGCCATCATTGGCGGATCCCACTCCAAGAACTACGTGCTG
 R  R  A  N  H  H  W  S  L  P  A  I  I  G  G  S  H  S  K  N  Y  V  L
TGGGAGTACGGAGGGTATGCCAGTGAAGGGGTGAAGCAAGTTGCTGAACTTGGCTCACCA
 W  E  Y  G  G  Y  A  S  E  G  V  K  Q  V  A  E  L  G  S  P
GTAAAAATGGAGGAAGAAATTCGACAACAGAGTGATGAAGTCCTCACTGTCATCAAAGCC
 V  K  M  E  E  E  I  R  Q  Q  S  D  E  V  L  T  V  I  K  A
AAAGCCCAGTGGCCATCCTGGCAGCCTGTGTCAATGTGAGAGCACCCTCAGCCGAATTC
 K  A  Q  W  P  S  W  Q  P  V  N  V  R  A  A  P  S  A  E  F
TCAGTGGACAGGACACGCCACTTGATGTCCTTCCTAACCATGATGGGCCCAGTCCCTGAC
 S  V  D  R  T  R  H  L  M  S  F  L  T  M  G  P  S  P  D
TGGAACGTGGGCCTATCTGCAGAGGATCTGTGCACCAAGGAGTGTGGGTGGGTCCAGAAA
 W  N  V  G  L  S  A  E  D  L  C  T  K  E  C  G  W  V  Q  K
GTGGTGCAGGACCTAATTCCCTGGGATGCTGGCACGGAGTGACCTAGTCTGGACCATCCT
 V  V  Q  D  L  I  P  W  D  A  G  T  D  S  G  V  T  Y  E  S
CCAAACAAGCCCACAATTCCCAGGAAAAAATCGACCCCCTGACTAGTCTGGACCATCCT
 P  N  K  P  T  I  P  Q  E  K  I  R  P  L  T  S  L  D  H  P
CAGAGTCCCTTTCTATGACCCGGAAGGTGGGTCCATCACAAGTGGCCAGAGTCGTCATC
 Q  S  P  F  Y  D  P  E  G  G  S  I  T  Q  V  A  R  V  V  I
GAGAGAATTGCCCGGAAGGAGAACAATGTCAACATTGTACCTGACAATGTGGATGATATT
 E  R  I  A  R  K  G  E  Q  C  N  I  V  P  D  N  V  D  D  I
GTAGCCGACCTGGCTCCAGAAGAAAAGATGAAGATGACACCCCTGAAACCTGCATCTAC
 V  A  D  L  A  P  E  E  K  D  E  D  D  T  P  E  T  C  I  Y
```

FIGURE 5C

```
TCCAACTGGTCCCCATGGTCTCGGCCTGCAGCTCTTCCACTTGTGAAAGGGTAAGAGGATG
 S  N  W  S  P  M  V  S  A  C  S  S  T  C  E  K  G  K  R  M
CGGCAACGCATGCTGAAGGCACAGCTGGACCTCAGTGCCCCTGTCTGACACCCAGGAC
 R  Q  R  M  L  K  A  Q  L  D  L  S  V  P  C  P  D  T  Q  D
TTCCAGCCCTGCATGGGCCCCGGCTGTCACCCTGCAGTGTCTCGCAGTGGCTCCACCATGTCG
 F  Q  P  C  M  G  P  G  C  H  P  A  V  S  S  A  V  A  P  P  M  S
GAGTGGATCACCTGGTCACCCTGCAGTGTCTCGTGGTATGGGCATGAGGTCCCGGGAG
 E  W  I  T  W  S  P  C  S  V  S  C  G  M  R  S  R  E
AGGTACGTGAAGCAGTTCCCGGAAGACGGTCCACCTGCCACCGGAAGAGACA
 R  Y  V  K  Q  F  P  E  D  G  S  V  C  M  L  P  T  E  E  T
GAGAAGTGCACGGTCAACGAGGAGTGCTCTCCAGCCTGGTGACTGAGTGGGGT
 E  K  C  T  V  N  E  E  C  S  P  S  C  L  V  T  E  W  G
GAGTGGGATGACTGCAGCGCCACCTGTGCAAGCGGCATGAAGAAGCGCCATCGCATGGTC
 E  W  D  D  C  S  A  T  C  G  M  K  K  R  H  R  M  V
AAGATGAGCCCGGCCGATGGCAGCATGTGCAAGGCGGAGACTTCGCAGGCGGAGAAATGC
 K  M  S  P  A  D  G  S  M  C  K  A  E  T  S  Q  A  E  K  C
ATGATGCCTGAGTGCCATATACCCGGCTTGTCCTTGCCTTGGTCCGAGTGGAGCGAC
 M  M  P  E  C  H  T  I  P  C  L  L  S  P  W  S  E  W  S  D
TGTAGCGTGACTTGTGGGAAGGGCATGCGCACCCGAATGCTCAAGTCTCTCTGGCA
 C  S  V  T  C  G  K  G  M  R  T  R  Q  R  M  L  K  S  L  A
GAGCTGGGGGACTGTAATGAGGATCTGGAGCAGGCGGAGAAGTGTATGCTGCCAGAGTGC
 E  L  G  D  C  N  E  D  L  E  Q  A  E  K  C  M  L  P  E  C
```

FIGURE 5D

```
CCCATTGACTGCGAACTCAGTGAGTGGTCCCAGTGGTCTGAATGTAACAAGTCCTGTGGG
 P  I  D  C  E  L  S  E  W  S  Q  W  S  E  C  N  K  S  C  G
AAGGTCACATGATTCGAACCCGGACAATCCAAATGGAACCTCAGTTTGGAGGTGCACCC
 K  G  H  M  I  R  T  R  T  I  Q  M  E  P  Q  F  G  G  A  P
TGCCCAGAGACTGTGCAACGCAAGAAGTGCCGTGCCCGGAAATGCCTTCGCAGCCCATCG
 C  P  E  T  V  Q  R  K  K  C  R  A  R  K  C  L  R  S  P  S
ATCCAGAAGCTGCGCTGGAGGGAGGCCCGAGAGAGCAGGAGTGAGCAGCTGAGGGAA
 I  Q  K  L  R  W  R  E  A  R  E  S  R  R  S  E  Q  L  R  E
GAGTCAGATGGAGAGCAGTTCCCAGGCTGTCGGATGCGCCCGTGGACTGCAGCCTGGTCAGAG
 E  S  D  G  E  Q  F  P  G  C  R  M  R  P  W  T  A  W  S  E
TGCACCAAACTGTGCGGAGGTGGGATCCAAGAACGCTACATGACTGTGAAGAAGAGGTTC
 C  T  K  L  C  G  G  G  I  Q  E  R  Y  M  T  V  K  K  R  F
AAAAGCTCCCAGTTTACCAGCTGCAAAGACAAGAAGGAGATCAGAGCGTGCAACGTGCAC
 K  S  S  Q  F  T  S  C  K  D  K  K  E  I  R  A  C  N  V  H
CCTTGTTAGTAGGGGTTCAACTCCCCAGGGCTGCATTCCAGATTCTAGTCACCAATGGTT
 P  C
GGGTGGTGTGTATTTGCTTGTTTAAGATGATTTAAATTGTGTCCACATGTTTTCATTTTAC
CGGTGTGGTTTGCCCAATAGTCTTATGGAGGCCGAGGGACATCTTGTCTGAATACTTCTT
GGTGAGTACAGGCCAAGCGGGACATCTGTCCCCAGGCCATCTTCCTGCTGCACTGAGTTG
AGTAGTGTTGGTTCACCTTGGTACTAAACTGAATCGTGTCCCTCTGGAGCATCCCCTGGT
CAAGCAGGGTGGAGACTTTGGCAAGACCAACCAGGAGCATGCGGG
AGACACAGCCATTAATTGCAAAGACAGATCCCTCTCTCACCTTTGGCCTTGCTCACTC
TTACAGAAACCTGTGTTTCCGCCCTCTTCGGTGCCCTGAAGGAGAAGCCCTGAGGTGGCA
AGTCTCCAGGTCATGGGTTCTTCGGTGCATCAAGGTCAGCAGGTCAGCAGGTGATGATGG
TTTGTTACAAACCTCCCAATACTGCTTTACTGCCGTGATTTCCGTTGTTGTTGGTGCTGCATAAAT
CTACTTCATTTGTGAGCCCTTGTCAGCCCTTGTCAGCAGACACATCAGCCTTCTTTGAGCCAATGT
GTCCTAGGATGCTGGACGGACACATCAGCCTTGTCAGCAGATCCCTTCTTTGAGCCAATGT
```

FIGURE 5E

```
AGACAGTAAGCTGGGCACTGGTTCCAAAGCCAACTTAAAATCTTCCTACACATATCCAGA
CCTTTTTTAGGTTGCCCAGGAAGCCCCCAAGTCAATTCTTCAACAAAATACTATCTTCCCTACT
GATAAGTCTGCCAGGAAGCCCCCAAGTCAATTCTTCAACAAAATACTATCTTCCCTACT
TAATTTTTTAAGTCATGATATTTATAGTTAGAGGAGAGAGACAATCTATTCCCAT
GACTAAGACACAAACCTACAAGAAAGGGTTACTCAGTCAAGCCTGTGCCTGACTTCTGGA
CCAGGCCCCTGATTTCATGGATAGTCCAAAGGAAGGCCAGGGTTCCCACTGACTCCAA
GCCATCAGCAGCACCCAAACCCAGGAGCAACAAATATTCAGAGAAAGAGGATGTTTATCT
CAGCTATGAGCTCATTGGCAGGTTGTACTCATGCATCTGTTAAAAGCACCACATCCT
TTTGCAAGTCTGTTTATTACCGCTTCATCCAAATACATTTTGTGGTCAAGATCGACACAG
TGCTATGAATACAGTACTTTAAGGTCTGCATTAAACACATCAGAATATTCCTGCCACAT
CTATGTACAACCCCTGAATATGTATTTTTCCTTAACACAAGAGAGCCTGTTCAATTAAAA
AAAAAAAA
```

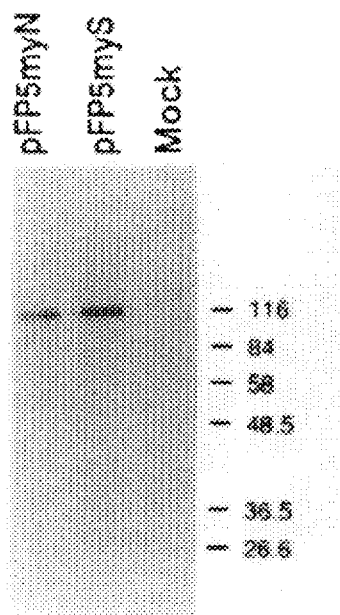
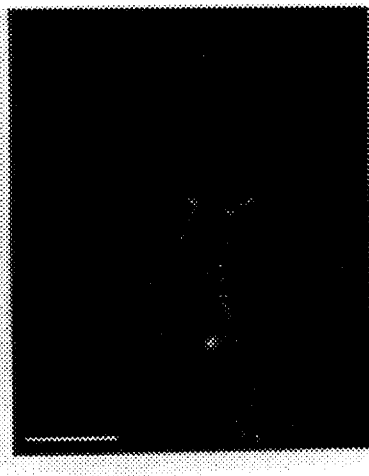
FIGURE 8B
FIGURE 8C
FIGURE 8D

FIGURE 10A
FIGURE 10B
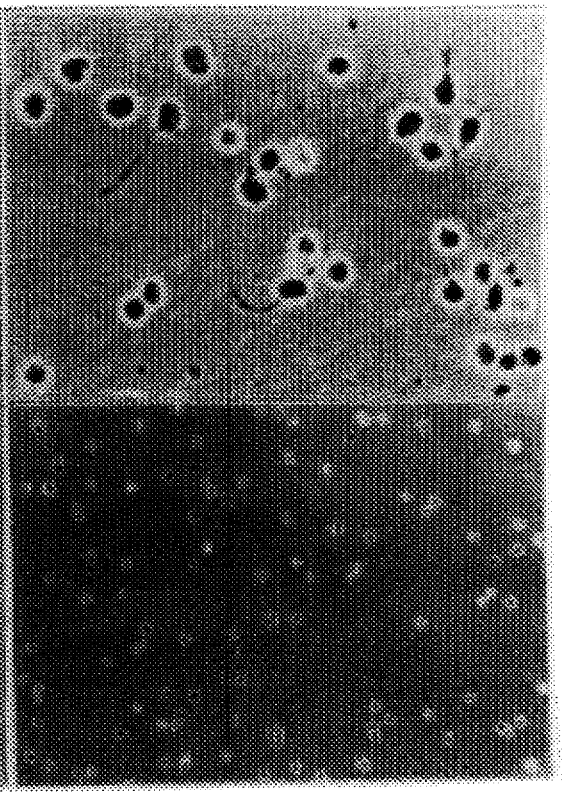
FIGURE 10C
FIGURE 10D 5,750,502

CLONING, EXPRESSION AND USES OF A SECRETED PROTEIN, F-SPONDIN

This application is a 371 of PCT/US93/03164, filed Apr. 2, 1993, which is a continuation-in-part of U.S. Ser. No. 07/862,021, filed Apr. 2, 1992, now U.S. Pat. No. 5,279,966.

BACKGROUND OF THE INVENTION

Throughout this application various references are referred to within parenthesis. Disclosures of these publications in their entireties are hereby incorporated by reference into this application to more fully describe the state of the art to which this invention pertains. Full bibliographic citation for these references may be found at the end of this application, preceding the sequence listing and the claims.

The early development of the vertebrate nervous system is controlled by local cell interactions that determine the identity of specific neural cell types and the pathways of growing axons. One of the first cell types to differentiate within the embryonic nervous system is the floor plate, a small group of epithelial cells located at the ventral midline of the neural tube (Schoenwolf and Smith, 1990). The differentiation of the floor plate is induced by local, possibly contact-dependent signals from the notochord (FIG. 1) (van Straaten et al., 1988; Placzek et al., 1990c; Hatta et al., 1991). Signals that derive from the floor plate have been implicated in the control of cell identity in the neural tube and in the guidance of axons (FIG. 1) (Jessell and Dodd, 1991).

Evidence that the floor plate is a source of polarizing signals that control cell identity and pattern in the neural tube has come from experiments in chick embryos in which floor plate cells grafted next to the neural tube of host embryos give rise to additional ectopic motor neurons and to other ventral neuronal types defined by cell specific antigenic markers (Yamada et al., 1991; Placzek et al., 1991). Inversely, preventing floor plate differentiation by removing the notochord leads to the formation of a spinal cord that is devoid of motor neurons and other ventral neurons. These grafting experiments suggest that the floor plate has a central role in establishing the identity and pattern of neuronal cell types present in the ventral spinal cord. The floor plate also has limb polarizing activity when grafted into the chick wing bud, possibly through the release of morphogenically active retinoids (Wagner et al., 1990).

After the identity of spinal cord neurons has been established, the floor plate appears to provide both long-range and local guidance cues that promote the growth of axons to and across the ventral midline of the spinal cord. First, the floor plate secretes a diffusible chemoattractant which can orient the growth of axons of commissural neuron in vitro (FIG. 1) (Tessier-Lavigne et al., 1988; Placzek et al., 1990a; Tessier-Lavigne and Placzek, 1991) and may account for the homing of these axons to the floor plate in vitro (Weber, 1938; Placzek et al., 1990b; Bovolenta and Dodd, 1991; Yaginuma and Oppenheim, 1991). Second, the floor plate may contribute to the change in trajectory of commissural axons from the transverse to the longitudinal plane that occurs immediately after crossing the ventral midline (FIG. 1) (Holley and Silver, 1987; Dodd et al., 1988; Bovolenta and Dodd, 1990). In support of this proposal, genetic mutations in mice and zebrafish that result in the absence of the floor plate during embryonic development lead to errors in the pathfinding of commissural axons at the midline of the spinal cord (Bovolenta and Dodd, 1991; Bernhardt and Kuwada, 1990).

Third, the floor plate may promote the fasciculation of commissural axons that occurs after they cross the midline of the spinal cord (Holley and Silver, 1987) by regulating the expression of glycoproteins of the immunoglobulin superfamily (Dodd et al., 1988; Schachner et al., 1990; Furley et al., 1990). The specialized role of the floor plate in vertebrate neural development has parallels in invertebrate organisms in that cells at the midline of the embryonic Diosophila and C. elegans central nervous systems have been implicated in neural patterning and axon guidance (Klambt et al., 1991; Nambu et al., 1991; Hedgecock and Hall, 1990).

To identify molecules that may mediate the diverse functions of the floor plate during early neural development, subtractive hybridization techniques have been used to isolate cDNA clones expressed selectively by the floor plate. The characterization of cDNA clones encoding a novel secreted protein, F-spondin, that is expressed at high levels by the floor plate during embryonic development is described here. The predicted amino acid sequence of F-spondin reveals that the protein contains domains similar to those present in the thrombospondin and other proteins implicated in cell adhesion and neurite outgrowth. In vitro assays show that F-spondin promotes neural cell adhesion and neurite outgrowth suggesting that the secretion of this protein by the floor plate contributes to the growth and guidance of axons in the developing CNS.

SUMMARY OF THE INVENTION

This invention provides an isolated vertebrate nucleic acid molecule encoding F-spondin. The isolated nucleic acid may be cDNA or RNA. The isolated vertebrate nucleic acid may be derived from human, rat, chicken or Xenopus.

This invention also provides a nucleic acid probe comprising a nucleic acid molecule of at least 15 nucleotides capable of specifically hybridizing with a sequence included within the sequence of a nucleic acid molecule encoding F-spondin. The nucleic acid probe may be DNA or RNA.

This invention provides a method to obtain F-spondin nucleic acid molecule. In an embodiment, a rat F-spondin gene is isolated by substractive hybridization. In another embodiment, a chicken F-spondin gene is isolated by screening a chicken cDNA library using a rat F-spondin probe. In a further embodiment, a Xenopus F-spondin is also isolated.

This invention further provides a host vector system for the production of a polypeptide having the biological activity of F-spondin. The isolated vertebrate F-spondin nucleic acid molecule is linked to a promoter of RNA transcription and then to a plasmid. The suitable host is a bacterial cell, insect cell, or animal cell, depending on the type of promoter and plasmid used. This invention also provides a method of producing a polypeptide having the biological activity of F-spondin, which comprises growing the selected host vector system under suitable conditions permitting production of the polypeptide and recovering the polypeptide so produced.

This invention further provides purified vertebrate F-spondin. Such purified F-spondin will be useful for adhesion and outgrowth of axon. This invention provides a method of attaching nerve cells to a matrix comprising contacting the matrix with nerve cell and purified F-spondin at a concentration effective to effect attachment of the cells to the matrix. This invention further provides a method of stimulating growth of a nerve cell comprising contacting the nerve cell with purified F-spondin at a concentration effective to stimulate growth of the nerve cell. This invention provides a method of regenerating nerve cells in a subject comprising administering to the subject purified F-spondin at a concentration effective to regenerate nerve cells in the subject. Finally, this invention provides a pharmaceutical composition for stimulating nerve cell growth comprising a pharmaceutically acceptable carrier and purified F-spondin at a concentration effective to stimulate nerve cell growth.

3A. Preferential expression of F-spondin mRNA in E13 (embryonic day 13) floor plate compared with E13 dorsal spinal cord at adult spleen. Two transcripts of 4.5 and 4.7 kb are detected in floor plate RNA.

3B. NCAM, Neural Cell Adhesion Molecule, mRNA is expressed at approximately equivalent levels in E13 floor plate and dorsal spinal cord and P0 (postnatal; day 0) brain.

3C. F-spondin mRNA is detected in blots of total RNA adult kidney and brain but not in adult liver or sciatic nerve.

Figure 4:
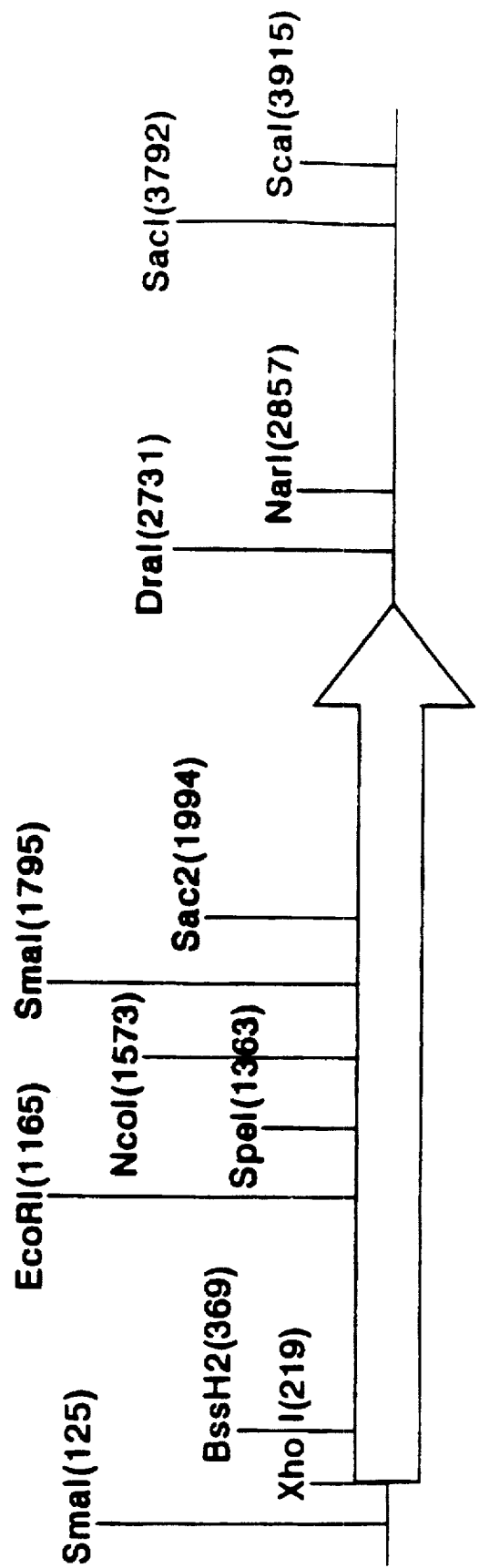

FIG. 4. Restriction map of the F-spondin cDNA. The arrow indicates the direction of translation. The restriction sites are indicated above the cDNA.

FIGS. 5A–5F. cDNA and predicted amino acid sequence of F-spondin.

5A–5E. Nucleotide (SEQ ID NO: 9) and amino acid sequence (SEQ ID NO: 10) of rat F-spondin determined from cDNA clones. The numbering of amino acids starts at the first methionine. Underlined NH$_2$ terminal residues indicates the putative signal sequence. Potential sites of N-linked glycosylation are indicated by double lines.

5F. Analysis of the hydrophobicity of the predicted F-spondin amino acid sequence. The plot was generated using the parameters given in Kyte and Doolittle (1982). The NH$_2$ terminus of the protein is to the left. Negative values indicate hydrophobic residues.

Figure 6A:
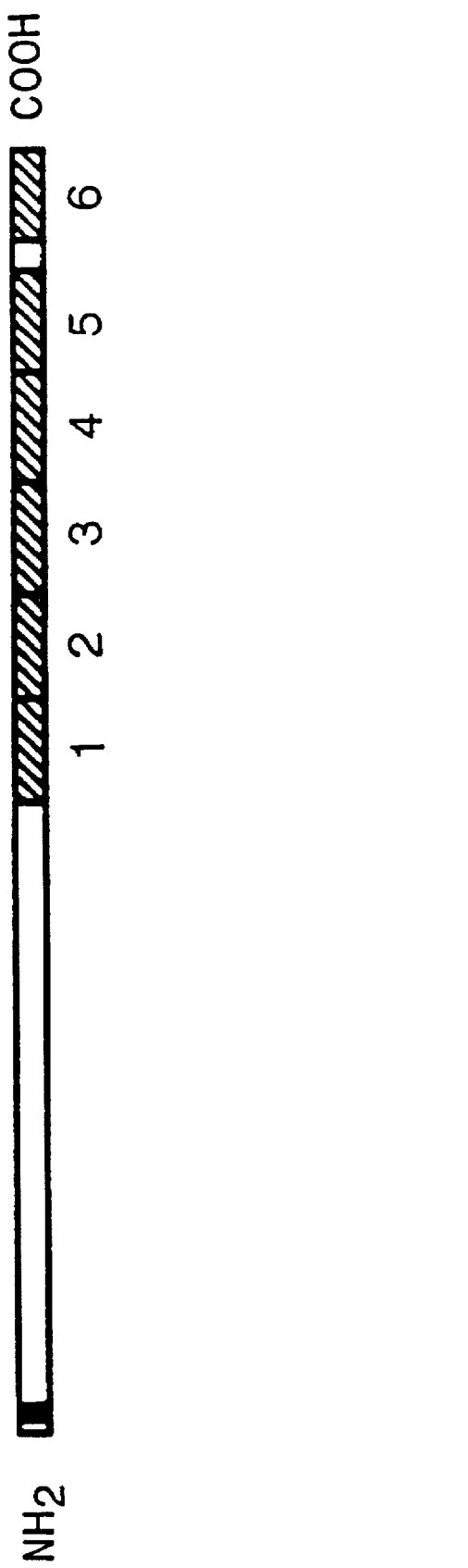
Figures 6B, 6C:
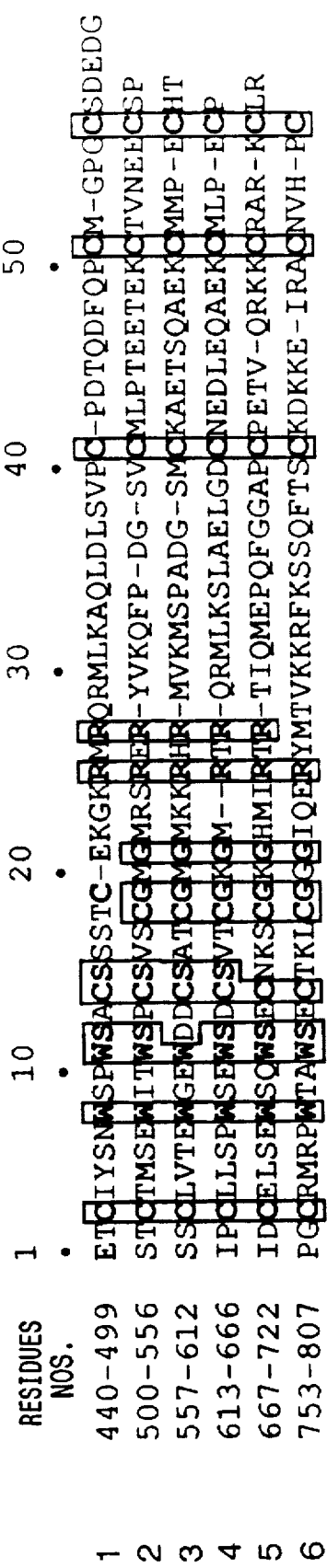

FIGS. 6A, 6B and 6C. Alignment of the carboxy terminal domain F-spondin and homology to thrombospondin type one repeats in other proteins.

6A. Schematic representation of the domain structure of F-spondin. The black box represents the signal sequence. The hatched box represents the thrombospondin type 1 repeats (TSRs).

6B. Alignment of the six repeats motifs in F-spondin which occupy residues 440–807 of the protein [residues 440–499 (Seq. I.D. No.: 15); residues 500–556 (Seq. I.D. No.: 16); residues 557–612 (Seq. I.D. No.: 17); residues 613–666 (Seq. I.D. No.: 18); residues 667–722 (Seq. I.D. No.: 19) and residues 723–807 (Seq. I.D. No.: 20)]. The position of the first and last amino acids of each repeat is shown on the left. Numbers over each repeat refer to the position of residues. Positions in which there are four or more identical residues are enclosed in boxes.

6C. Comparison of the conserved F-spondin motif with the conserved TSRs found in thrombospondin I, (SEQ. I.D. NO.: 21) thrombospondin II (SEQ. I.D. NO.: 22), region II of the plasmodial circumsporooite (Cs) proteins (SEQ. I.D. NO.: 27) thrombospondin-related anonymous protein (TRAP) (SEQ. I.D. NO.: 28), properdin (SEQ. I.D. NO.: 24) and in the N-and C-terminal regions of the complement proteins C6, C7, C8a, C8b and C9 (Seq. I.D. No.: 26 and Seq. I.D. No.: 25, respectively). The number at the right of the figure indicates the number of TSR domains that contain VTCG sequence (SEQ. I.D. NO.: 6) as a proportion of the total number of TSR domains.

FIGS. 7A, 7B, 7C, 7D, 7E, 7F, 7G and 7H. Localization of F-spondin mRNA in the developing spinal cord.

7A. Autoradiographic localization of F-spondin mRNA in the hindbrain of a day 10 rat embryo by in situ hybridization using an antisense RNA probe. Intense hybridization is detected at the ventral midline of the neural tube and possible also in the axial mesoderm underlying the neural tube.

7B. Localization of whole mount in situ F-spondin mRNA by E11 (embryonic day 11) rat embryos hybridization histochemistry using digoxigenin-labelled antisense probe. Hybridization is detected in the floor plate of the midbrain, hindbrain and spinal cord (arrow heads).

7C. Bright field micrograph showing localization of F-spondin mRNA in E12 (embryonic day 12) rat spinal cord. The floor plate is intensely labelled.

7D. Dark field micrograph of a similar section showing a low level of hybridization is in the ventral horn in addition to intense labelling in the floor plate. Hybridization is also detected in the ventral root.

7E. Dark field micrograph showing the floor plate and the ventral ventricular zone of E13 spinal cord express high levels of F-spondin mRNA.

7F. Bright field micrograph of E16 (embryonic day 16) spinal cord showing that F-spondin mRNA levels are still high in the floor plate and the ventral ventricular zone.

7G. Dark field micrograph showing that by E16, significant hybridization is also detected in ventral and intermediate regions of the spinal cord.

7H. Dark field micrographs showing a uniform distribution of F-spondin mRNA.

Scale bar: A=100 µm; B=350 µm; C=80 µm; E=100 µm; F=170 µm; G=170 µm; H=120 µm.

FIGS. 8A, 8B, 8C and 8D. F-Spondin$^{myc}$ is secreted by cos cells and associated with the cell surface.

8A. Position of insertion of an oligonucleotide encoding for a 10 amino acid region of the c-myc oncogene ligated into unique NcoI site or SpeI sites within the F-spondin cDNA.

8B. Immunoprecipitation of conditioned media obtained by exposure of 40 h to cos cells transfected with pFP5myS, pFP5myN and to mock transfected cells. Both constructs generated a single protein band at 116 kDa.

8C. Phase contrast micrograph showing a small group of transfected cos cells.

8D. Immunofluorescence micrograph showing the localization of F-spondin$^{myc}$ on the cell surface. Immunoreactivity is detectable at much higher levels at cell-cell rather than at cell-substrate contacts.

Scale bar in C, D=20 µm

FIGS. 9A, 9B, 9C and 9D. F-spondin$^{myc}$ promotes the extension of neurites from DRG neurons in vitro. F-spondin$^{myc}$ protein obtained from transfected cos cells supernatants was affinity purified and analyzed by SDS-PAGE(8–25%) and silver staining. (9A) Two stained bands are observed, which may reflect differences in the glycosylation of F-spondin. Neural cells isolated from E14 rat dorsal root ganglia were plated on F-spondin (9B) or on cos cell-conditioned media (9C) or BSA (not shown) substrates for 14h and then fixed and labelled with MAb 3A10 and visualized by indirect immunofluorescence. (9D) The length of the longest neurite of each 3A10-positive neurons was measured (or recorded as 0 mm if no neurite was seen). The percentage of neurons (ordinate) with neurites longer than a given length in μm (abscissa) is plotted. Similar results were obtained in 5 experiments. Only non-fasciculated neurites were included in the plots shown in D. Scale bar in B and C=100 μm.

FIGS. 10A, 10B, 10C, 10D, 10E and 10F. F-spondin promotes the adhesion of dorsal spinal cord cells. A single cell suspension of E13 dorsal spinal cord cells ($10^6$ cells/35 mm disk) was plated on, F-spondin$^{myc}$ (10A and 10B), on BSA (10C) and on F-spondin$^{myc}$ substrate in the presence of heparin (1 mg/ml) (10D), for 1 h. Cells were then washed in PBS, fixed and counted.

10E. Box plot showing dose-dependent adhesion of E13 dorsal spinal cord cells to different amounts of F-spondin$^{myc}$ substrate. Each box represents cell counts from 10 different fields. Similar results were obtained in 3 separate experiments.

10F. Box plot showing inhibition of the adhesion of E13 dorsal spinal cord cells to F-spondin$^{myc}$ in the presence of different concentrations of heparin and chondroitin sulfate. The inhibition at all concentrations of chondroitin sulfate and heparin is significant ($p<0.001$; Ttest). Scale bar in A, C, D=200 μm. B=50 μm Box plot: The box enclosed 50% of the population with the median marked as a bold line and the mean as a dot. The range of the data is indicated by the extent of the lines. Each plot represents 10 determinations from one of three similar experiments.

DETAILED DESCRIPTION OF THE INVENTION

This invention provides isolated vertebrate nucleic acid molecules which encode F-spondin. As used herein, the term F-spondin encompasses any amino acid sequence, polypeptide or protein having the biological activities provided by the F-spondin.

In one embodiment of this invention, the isolated nucleic acid molecules described hereinabove are DNA. In other embodiments of this invention, the isolated nucleic acid molecules described hereinabove are cDNA, or RNA. In the preferred embodiment of this invention, the isolated nucleic molecules are cDNAs as shown in Sequence I.D. Nos. 9, 11 and 13.

This invention also encompasses DNAs and cDNAs which encode amino acid sequences which differ from those of F-spondin, but which should not produce phenotypic changes. Alternatively, this invention also encompasses DNAs and cDNAs which hybridize to the DNA and cDNA of the subject invention. Hybridization methods are well known to those of skill in the art.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These sequences include: the incorporation of codons "preferred" for expression by selected non-mammalian host; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecules are useful for generating new cloning and expression vectors, transformed and transfected procaryotic and eucaryotic host cells, and new and useful methods for cultured growth of such host cells capable of expression of the polypeptide and related products.

Moreover, the isolated nucleic acid molecules are useful for the development of probes to study neurodevelopment.

F-spondin may be produced by a variety of vertebrates. In an embodiment, a rat F-spondin nucleic acid is isolated. A restriction map of the cDNA of rat F-spondin is shown in FIG. 4. The Xho1-Dra1 fragment of rat F-spondin was excised from the F-spondin cDNA. The Xho1 site was blunt-ended with T4 DNA polymerase, and Bgl2 linkers (12 mers) was ligated. The fragment was subcloned into BamH1 site of pBluescript SK (Strategene). The 5' of the gene is located near the T3 promoter. The resulting plasmid, pFP5/KS, encoding the rat F-spondin was deposited on Mar. 19, 1992 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pFP5/KS was accorded ATCC accession number 75215.

In another embodiment, a chicken F-spondin cDNA was isolated (Seq. ID No. 11). The translation initiates at nucleotide position 136. In a further embodiment, a partial Xenopus F-spondin was isolated (Seq. ID No. 13).

Throughout this application, references to specific nucleotides are to nucleotides present on the coding strand of the nucleic acid. The following standard abbreviations are used throughout the specification to indicate specific nucleotides:

C=cytosine A=adenosine
T=thymidine G=guanosine

For the purpose of illustration only, applicants used a substractive hybridization techniques to isolate and characterize F-spondin cDNA clones in rats. Similar substractive hybridization techniques are applicable to isolate and characterize the F-spondin genes in different vertebrates.

Alternatively, the F-spondin genes may be isolated using the probe generated from the rat F-spondin gene. The chicken and Xenopus homologous F-spondin genes have recently been cloned by applicants. These genes are extremely conserved and share 90% homology at the amino acid level and about 70% homology at the nucleic acid level. The chicken gene was isolated by low stringency screening of embryonic spinal cord cDNA library whereas the Xenopus F-spondin gene was isolated by low stringency screening of the whole embryo cDNA library, both using probes from the coding region of rat F-spondin.

For the human F-spondin gene, it is conceivable that the degree of homology between rat and human would be even greater since both rat and humans are mammals. Human embryonic brain cDNA library, available from Clontech, and human genomic library may be used for such screening. Duplicated filters of human libraries may be screened with radiolabelled probe derived from the rat F-spondin. The probe may be encompassing the coding region, since the homology of F-spondin across species is through the whole coding region. The filters containing the human libraries will be hybridized with the probes at low stringency (Sambrook et al. 1989) and positive clone will be further analyzed by DNA sequencing techniques which are well known to an ordinary skilled artisan.

This invention provides a nucleic probe comprising a nucleic acid molecule of at least 15 nucleotides capable of specifically hybridizing with a sequence included within the sequence of a nucleic acid molecule encoding a F-spondin, for example, with a coding sequence included within the sequence shown in FIG. 5 and Sequence ID number 9. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes F-spondin into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

The probes are useful for 'in situ' hybridization to locate tissues which express this gene, or for other hybridization assays for the presence of this gene or its mRNA in various biological tissues.

Vectors which comprise the isolated nucleic acid molecule described hereinabove also are provided. Suitable vectors comprise, but are not limited to, a plasmid or a virus. These vectors may be transformed into a suitable host cell to form a host cell vector system for the production of a polypeptide having the biological activity of F-spondin.

This invention further provides an isolated DNA or cDNA molecule described hereinabove wherein the host cell is selected from the group consisting of bacterial cells (such as E. coli), yeast cells, fungal cells, insect cells and animal cells. Suitable animal cells include, but are not limited to Vero cells, HeLa cells, Cos cells, CV1 cells and various primary mammalian cells.

This invention provides a method to identify and purify expressed F-spondin proteins. A myc-epitope was first introduced into the F-spondin protein. This F-spondin carrying myc-spondin may be linked to an expression vector. Such vector may be used to transfect cells and the distribution of F-spondin in the cells can be detected by reacting myc antibodies known to be reactive to the introduced myc-epitope with the transfected cells which express the F-spondin carrying myc-epitope. Taking advantage of this myc-epitope, F-spondin may be purified by an antibody affinity column which binds with this myc-epitope.

In one embodiment, myc-epitope is introduced in the NcoI site of the rat F-spondin. After that the SmaI (125), Dra (2731) fragment of the rat F-spondin was isolated. Bgl2 linkers were added, and the fragment was subcloned into the BamH 1 site of pcDNA neo (InVitrogene). The 5' end of the gene is located near the T7 RNA promoter. The resulting plasmid, pcFP5.myn, was deposited on Mar. 19, 1992 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pcFP5.myn was accorded ATCC designation number 75216.

The above uses of the myc-epitope for identification and purification of F-spondin should not be considered limiting only to the myc-epitope. Other epitopes with specific antibodies against them which are well known to one of ordinary skill in the art could be similarly used.

Also provided by this invention are complete F-spondin protein sequences (seq. ID Nos. 10, 12). In an embodiment a complete rat F-spondin protein sequence is disclosed (Seq. ID No. 10). In another embodiment a complete chicken F-spondin protein sequence is provided (Seq. ID No. 12). In a further embodiment a partial Xenopus F-spondin protein sequence is also provided (Seq. ID No. 14).

Further provided by this invention is a purified, F-spondin polypeptide. As used herein, the term "purified F-spondin" shall mean isolated naturally-occurring F-spondin or protein (purified from nature or manufactured such that the primary, secondary and tertiary conformation, and posttranslational modifications are identical to naturally-occurring material) as well as non-naturally occurring polypeptides having a primary structural conformation (i.e. continuous sequence of amino acid residues). Such polypeptides include derivatives and analogs.

F-spondin will be useful for adhesion and outgrowth of axon. Therefore, this invention also provides a method of attaching nerve cells to a matrix comprising contacting the matrix with nerve cells and purified F-spondin at a concentration effective to effect attachment of the cells to the matrix.

Methods to determine such a concentration are well-known in the art. The effective concentration of F-spondin may be determined by using different concentrations of purified F-spondin to the matrix and the nerve cell. The concentration in which attachment of the matrix and the nerve cell is observed is the effective concentration.

This invention further provides a method of stimulating growth of a nerve cell comprising contacting the nerve cell with purified F-spondin at a concentration effective to stimulate growth of the nerve cell.

This invention also provides a method of regenerating nerve cells in a subject comprising administering to the subject purified F-spondin at a concentration effective to regenerate nerve cells in the subject.

Finally, this invention provides a pharmaceutical composition for stimulating nerve cell growth comprising a pharmaceutically acceptable carrier and purified F-spondin at a concentration effective to stimulate nerve cell growth.

For the purposes of this invention "pharmaceutically acceptable carriers" means any of the standard pharmaceutical vehicles. Examples of suitable vehicles are well known in the art and may include, but not limited to, any of the standard pharmaceutical vehicles such as a phosphate buffered saline solutions, phosphate buffered saline containing Polysorb 80, water, emulsions such as oil/water emulsion, and various type of wetting agents.

This invention will be better understood from the Experimental Details which follow. However, one skilled in the art will readily appreciate that the specific methods and results discussed are merely illustrative of the invention as described more fully in the claims which follow thereafter.

Experimental Details Experimental Procedures Library Construction and Screening

Directional cDNA libraries were constructed in Lambda ZAP® II (Stratagene®) from embryonic day (E) 13 floor plate and dorsal spinal cord poly (A)+-selected RNA. The 5' ends of the cDNA inserts were located downstream of the T3 RNA polymerase promotor, and the 3' ends downstream of the T7 RNA polymerase promotor. DNA was prepared from the library using the plate lysate method (Sambrook et al., 1989). The DNA was linearized with XhoI and RNA was transcribed with T3 RNA polymerase (Stratagene®). RNA from the dorsal spinal cord library was transcribed in the presence of UTP-biotin (Clontec) diluted 1:10 with UTP. First-strand cDNA was transcribed from the T3 floor plate RNA using an oligo dT XhoI linker (Stratagene®).

Solution hybridization of first strand floor plate cDNA and the dorsal T3 biotinylated RNA was performed as described by Sive and St. John (1988). Approximately 1 µg of cDNA was hybridized with a 30-fold molar excess of RNA. The nucleic acids were dissolved in 10 µl of hybridization buffer containing 50 mM HEPES (pH 7.6), 0.2% SDS, 2 mM EDTA, 500 mM NaCl, and incubated at 68° C. Under these conditions, CoT values greater than 100 were obtained. The hybridization mixture was diluted to 60 µl with hybridization buffer without SDS, and 10 µg streptavidin was added. The cDNA/biotin RNA hybrids were removed by phenol-chloroform extraction. The remaining single strand cDNA was isolated and hybridized with a 300 fold excess of biotinylated RNA as described above. About 10% of the starting cDNA was recovered in the first hybridization and about 15-20% from the second hybridization.

The subtracted cDNAs were subjected to 20 cycles of a PCR reaction using oligo dT XhoI linker primer and SK primers (Stratagene®). The products of the PCR reaction were cut with EcoRI and XhoI, the primers and the flanking sequences were removed with sephacryl S-300 spin columns (Pharmacia®). The inserts were cloned into Lambda ZAP II arms.

Duplicate filters of the subtracted floor plate library were screened with radiolabelled first strand cDNA derived from floor plate and dorsal spinal cord. 100 ng of mRNA was incubated in 20 µl of 50 mM Tris pH 8.3, 10 mM MgCl$_2$, 150 mM KCl, 1.0 mM dGTP, 1.0 mM dTTP, 100 µCi[32p]dATP (3000 Ci/mmol), 100 µCi[$^{32}$P]dCTP (3000 Ci/mmol), 100 mg/ml oligo dT, 10 mM DTT, 10 U of RNasin (Promega), 20 U of MU1V reverse transcriptase (BRL), for 30 min in 37° C. 4×10$^3$ recombinant phage were plated and screened. Hybridization and washes were performed at high stringency (Sambrook et al., 1989). The floor plate cDNA probe selectively hybridized with 24 phages. Cross hybridization analysis revealed that these phages corresponded to three different cDNAs designated FP2, FP5 and FP24. The pattern of expression in the spinal cord was determined by in situ hybridization. FP2 and FP5 are expressed selectively in the floor plate while FP24 is expressed in the floor plate, roofplate and in the ventricular zone of the spinal cord. The degree of enrichment as determined by screening the floor plate enriched library and floor plate library with FP2, FP5 and FP35, which is expressed selectively in the floor plate (McKanna & Cohen, 1989) is about 50-fold.

RNA Transfer Analysis

Total RNA was prepared from various tissues using the RNA Azol method (Biotex Laboratories) and then enriched for poly (A)$^+$ containing transcripts by passage over an oligo (dT) cellulose matrix. RNA transfer was performed as described by Thomas (1980). Probes were labelled by random priming (Feinberg and Vogelstein, 1984) and hybridized under standard conditions.

DNA Sequencing and Analysis cDNA inserts were excised directly as Bluescript plasmids (Stratagene®). The nucleotide sequence of the inserts were determined by the dideoxy chain-termination method (Sanger et al., 1977) using both double-stranded and single-stranded DNA as template for T7 DNA polymerase (Sequenase, United States Biochemicals). The nucleotide sequence of the entire coding region was determined by sequencing both strands. Sequences were assembled on an Apple Macintosh computer using the MacVector (IBI) program.

In Situ Hybridization

In situ hybridization was preformed as described previously (Wilkinson et al., 1987) using a T3 or T7 RNA polymerase-derived [$^{35}$S]UTP-labelled single stranded antisense RNA probe which encompasses a region of the 3' sense RNA untranslated region of F-spondin (nt 3359–4029), or the TSRs (nt 1545–2626). Exposure times range from four to fourteen days. Sense probes were used as controls.

For whole mount in situ hybridization, E11 rat embryos were fixed in 0.1M MOPS, 2 mM EGTA, 1 mM Mg SO4, 3.7% formaldehyde for 2 hours. In situ hybridization was preformed essentially as described by Harland (1991), with a few modifications: anti-digoxygenin antibody (Boehringer Mannheim), was preabsorbed to E14 rat acetone powder (1%) (Harlow and Lane, 1988) before addition to the hybridization mixture. The chromogenic reaction was carried out for 1–2 h.

DNA Constructs

The myc epitope was introduced as follows: Two partially complementary oligonucleotides with the sequence: 5'-CTAGCGAGCAGAAGCTGATCTCCGAGGAGGAC-CTCA-3' (Seq. ID No. 1) and 5'-CTAGTGAGGTCCTCCTCGGAGATCAGCTTCTGC-TCG-3' (Seq. ID No. 2) were annealed to obtain a double-stranded DNA fragment coding for the c-myc proto-oncogene epitope EQKLISEEDL (Seq. ID No. 3) flanked by a SpeI site. The fragment was cloned into a unique SpeI site (nt 1365) in F-spondin. The same epitope was also introduced into a NcoI site (nt 1575) using the oligonucleotides: 5'-CATGGGAGCAGAAGCTGATCTCCGAGGAGGACC-TCG-3' (Seq. ID No. 4) and 5'-CATGCGAGGTCCTCCTCGGAGATCAGCTTCTGCT-CC-3' (Seq. ID No. 5). The tagged F-spondin DNA was subcloned into the expression vector pMT21 (provided by Genetics Institute), or pcDNA-I (InVitrogen).

cos Cells Transfection

Cos cells were transfected by the DEAE-Dextran method as follows: 80% confluent overnight cultures were transfected with 5 µg DNA, per 100 mm dish, in 250 µg/ml DEAE Dextran (Pharmacia®), 100 mM Tris pH 7.3, in DMEM. After 6 h cells were washed and incubated in DMEM 10% calf serum, 0.1 mM choloroquine (Sigma) for 2.5 h, followed by incubation in DMEM 10% calf serum overnight. For isolation of F-spondin the medium was changed to OPTI-MEM (BRL), and the cells were incubated for 48 h.

Metabolic Labeling of Cos Cells and Immunoprecipitation

Transfected cos cells were preincubated in methionine-free DMEM (BRL®-GIBCO). After 1 h at 37° C., 250 µCi/ml[$^{35}$S] methionine (NEN) was added, and the cells were incubated for an additional 3 h. The medium was collected and incubated with anti-myc antibody (MAb 9E10) for 1 h. The immune complex was precipitated with fixed *Staphylococcus aureus* (BRL®) for 1 h. Pellets were washed three times with PBS, before resuspension in 1x sample buffer. $^{35}$S-labelled immunoprecipitated proteins were visualized after electrophoresis on 10% SDS-polyacrylamide gels.

Immunocytochemistry

F-spondin tagged with the c-myc epitope was detected with MAb 9E10 (Evan et al., 1985). Fluoresceinated isotype-specific second antibody (Boehringer® Mannheim; goat antimouse IgG) was used at a dilution of 1:100. For immunofluorescence labelling (Dodd and Jessell, 1985), cultures were washed once at 22° C. with L15 and then incubated with primary antibody for 30 min at 22° C. Cultures were then washed twice in L15-1% normal goat serum (NGS) and incubated with secondary FITC conjugated isotype-specific antibody diluted in L15-1% NGS for 30 min at 22° C. Cultures were washed twice and fixed in 4% paraformaldehyde in 0.2M phosphate buffer (PB) for 20 min, rinsed in 0.12M PB and coverslipped in 0.05% paraphenylenediamine (Sigma) in 0.2M sodium carbonate (pH 9.0); glycerol (1:1). Cultures were viewed on a Zeiss Axioplan microscope under epifluorescence optics.

Cell Culture

Spinal cords dissected from embryonic day (E) 13 rats and placed into L15 medium at 4° C. The dorsal region of the spinal cord was dissected and incubated with 0.05 trypsin (Gibco) for 20 min in a $Ca^{2+}/Mg^{2+}$-free modified essential medium (S-MEM) (Gibco) supplemented with 8 mg ml$^{-1}$ glucose. The tissue was then washed with S-MEM and triturated to give a single cell suspension. Spinal cord cells were plated in 35 mm tissue culture dishes on appropriate substrates and grown in Ham's E12 medium (Gibco) supplemented with N3 additive (F12-N3) (Romijin et al., 1982) at a density of $10^6$ cells/dish in a 5% CO2 humidified incubator at 37° C. Dorsal root ganglia were dissected from E14 rats and treated as described above. Cells were incubated with 0.1 trypsin, and plated with F12-N3 supplemented with 100 ng NGF at a density of $4 \times 10^4$/dish.

Neurite Outgrowth Assays $5 \times 10^{10}$ cos cells were transfected with pFP5myN and conditioned medium was collected. F-spondin$^{myc}$, was affinity purified on a monoclonal anti-myc (9E10) affinity column. Affinity purified F-spondin$^{myc}$ (20 µl/ml) was absorbed onto nitrocellulose (Lemmon et al., 1989). For controls, parental cos cell conditioned medium was purified on the same column and used as a substrate on nitrocellulose. The nitrocellulose was then blocked with bovine serum albumin (10 mg/ml) which provided a further control for background neurite outgrowth. E14 dorsal root ganglion (DRG) neurons were plated on immobilized protein substrates at a density of $2-10 \times 10^4$ cells/35 mm tissue culture dish (Nunc, 35 mm diameter) and grown for 14 h. Cultures were then fixed in 4% paraformaldehyde, permeabilized with 0.1% Triton X-100 and stained using MAb 3A10 (Furley et al., 1990; available from Developmental Studies Hybridoma Bank), which recognizes a neuronal filament-associated protein and serves as a marker for fine neurites. Neuronal cell bodies and neurites were visualized by indirect immunofluorescence on a Zeiss Axioplan microscope. Neurite lengths were measured as the distance from the edge of the soma (sharply defined by 3A10 fluorescence) to the tip of its longest neurite. Neurite lengths were only measured if the entire length to the neurite could be unambiguously identified. About 25 neurites were measurable within each protein-coated area (3–4 mm$^2$).

Adhesion Assay

Dissociated E13 dorsal spinal cord cells were plated on immobilized protein substrate at a density of $10^6$ cells/35 mm tissue culture dish (Nunc, 35 mm diameter). After one hour the cultures were washed twice with PBS and fixed in 4% paraformaldehyde. Cells were counted on a Zeiss Axioplan microscope at 400x magnification. Ten independent counts were taken from each experiment. The floor plate is a transient neural cell group implicated in the control of cell pattern and axonal growth in the developing vertebrate nervous system.

Figure 1A:
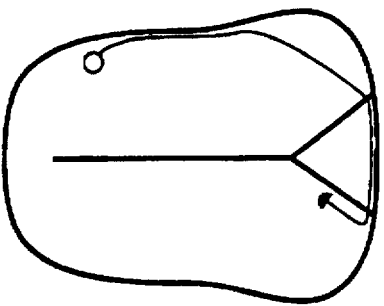
FIG. 1. Diagram showing the induction and proposed functions of the floor plate during early spinal cord development. For details see text.
Figure 1B:
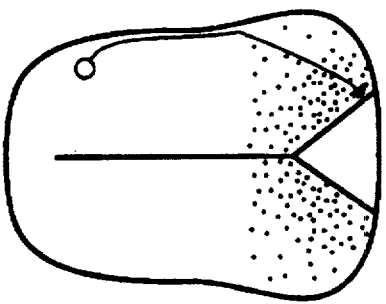
Figure 1C:
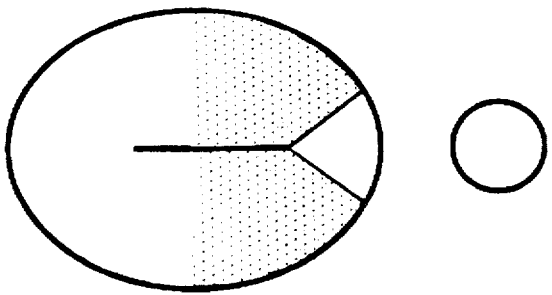
Figure 1D:
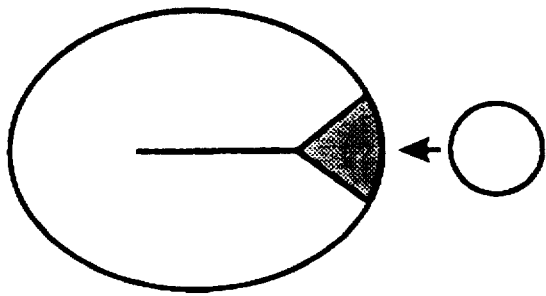
Figure 2:
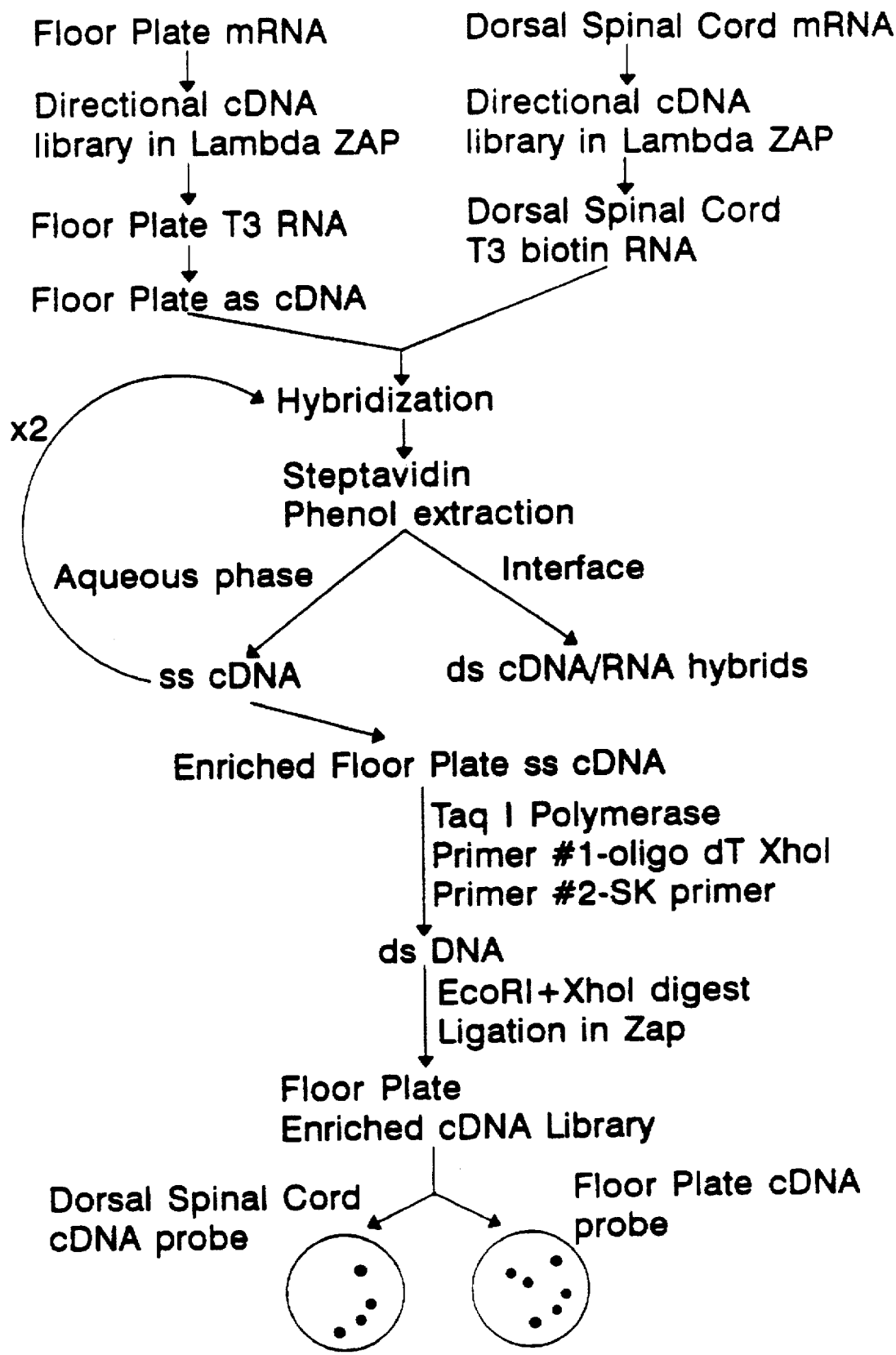
FIG. 2. Schematic diagram of the subtractive hybridization protocol used to identify floor plate specific cDNA clones. For details see text.
Figure 3A:
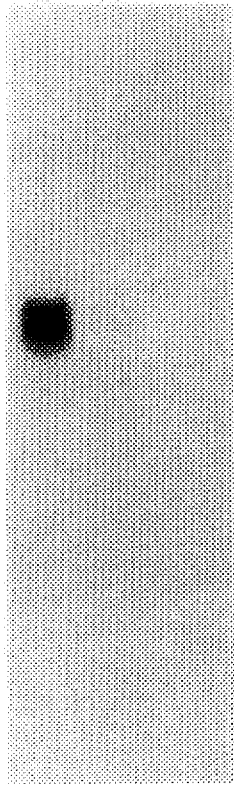
FIGS. 3A, 3B and 3C. Expression of F-spondin mRNA. Total cellular RNA or poly (A)$^+$ RNA was isolated from different tissues and separated on 1% agarose-formaldehyde gels and blotted to nylon membranes. The blot was analyzed with cDNA probes derived from the F-spondin 3' noncoding region labelled by random priming.
Figure 3B:
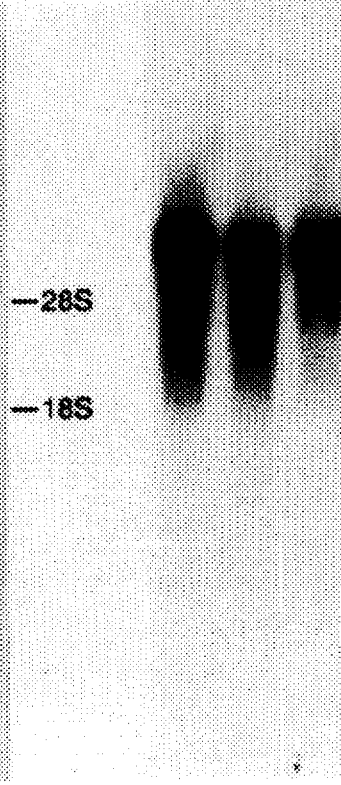
Figure 3C:
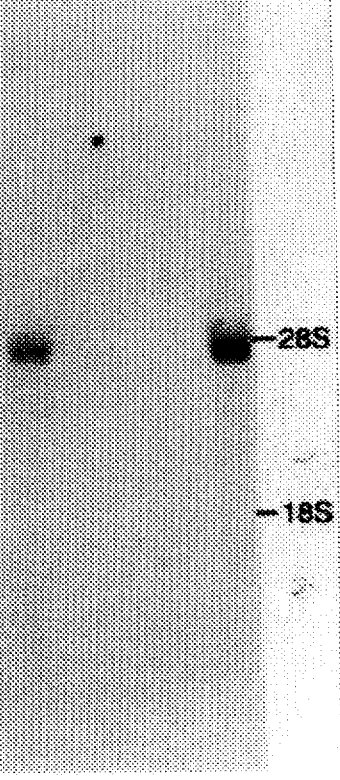

Experimental Results Identification and Sequence of a Floor Plate-Enriched cDNA Clone Cellular assays have revealed that the floor plate has several specialized signalling functions during the embryonic development of the spinal cord. Floor plate-derived signals are likely to be encoded by proteins whose mRNAs are restricted to or are highly enriched in the floor plate. In order to identify such molecules subtractive hybridization techniques have been used to isolate cDNA clones that are expressed by the floor plate but not by the dorsal spinal cord in embryonic day (E) 13 rat embryos (see FIG. 2 and Experimental Procedures). One cDNA clone identified in this screen, designated FP5, contained a 0.5 kb insert which hybridized to two major transcripts of 4.5 and 4.7 kb in poly (A)$^+$-selected RNA derived from E13 rat floor plate (FIG. 3A). Very faint hybridization to the same two transcripts was detected in RNA derived from E13 dorsal spinal cord (FIG. 3A) and post-natal day (P) 0 brain (FIG. 3C), whereas no hybridization was detected to RNA derived from adult liver and spleen (FIGS. 3A and 3C). The specificity of expression of FP5 transcripts within E13 rat spinal cord was confirmed by in situ hybridization histochemistry which showed that FP5 mRNA is expressed at very high levels in the floor plate but is undetectable in the dorsal region of E13 rat spinal cord (see below). These studies indicate that FP5 transcripts are highly enriched in the floor plate.

Screening of an E13 rat floor plate cDNA library with the 0.5 kb cDNA insert from the FP5 clone identified several additional cDNA clones of which clone FP5-9 contained a 4 kb insert. The FP5-9 cDNA contains a single long open reading frame that starts with a methionine codon at nucleotide 226 associated with a conventional translation initiation sequence (Kozak, 1984) and ends with a TGA stop codon at nucleotide 2646 (FIGS. 5A–5E). No in-frame methionine codons were found upstream of the putative translation initiation site and sequences 5' of the initiation site contain stop codons in all three reading frames. Sequencing of several other independently isolated FP5 cDNA subclones spanning the entire coding region did not reveal any differences in the nucleotide sequence of the open reading frame.

Figure 5F:
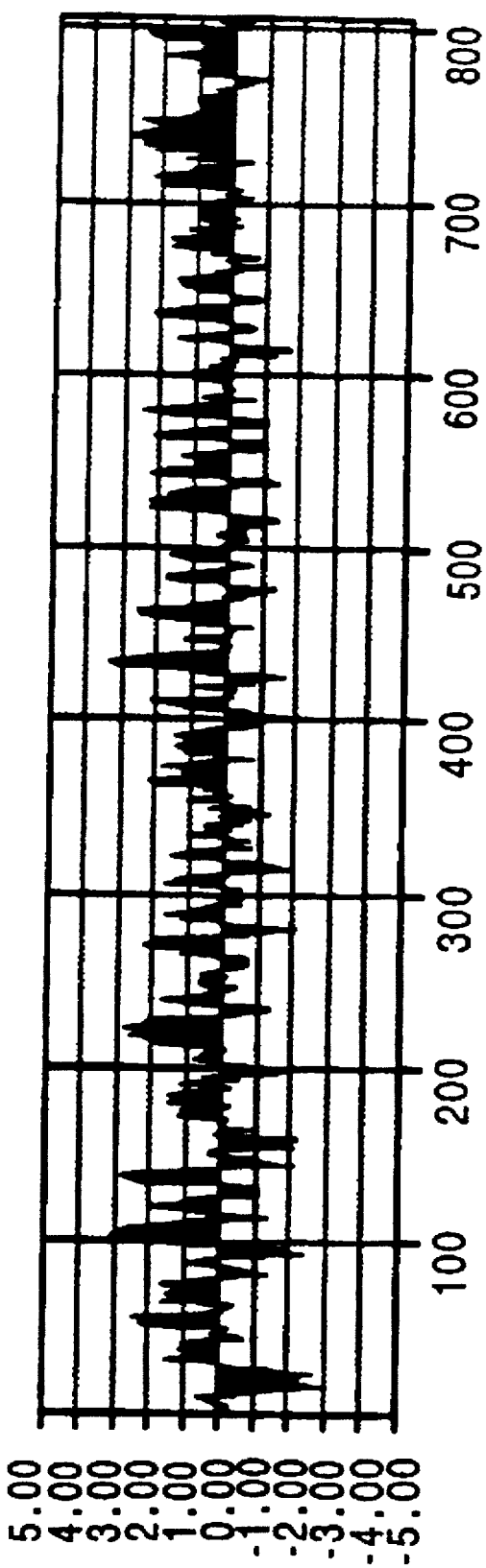

Translation of the open reading frame FP5-9 predicts a protein 807 amino acids with a molecular mass of 90,766 daltons, and N-terminal hydrophobic leader sequence (FIG. 5A; Seq. ID No. 9) with a consensus signal peptide cleavage site (von Heijne, 1985). No other long stretches of hydrophobic residues were observed (FIG. 5F) suggesting that the protein does not possess a transmembrane spanning domain. The amino terminal domain of FP5-9 contains a region of clustered basic residues (residues 138–142) which could represent a site for proteolytic processing by mammalian subtilisin-like cleavage enzymes (Steiner, 1991). In addition, the predicted protein contains three N-linked glycosylation sites (FIGS. 5A–5F). Collectively, these features suggest that the FP5-9 cDNA encodes a secreted protein.

The Protein Encoded by the FP5-9 cDNA has Structural Features of Cell and Substrate Adhesion Molecules Analysis of the predicted amino acid sequence of the FP5-9 encoded protein reveals that it is separable into two major domains (FIG. 6A). The NH$_2$-terminal domain of 440 residues contains 10 cysteine residues and exhibits no sequence homology to other proteins in the Genbank database. The COOH terminal of the protein extends from residues 441–807 and contains six repeats of a domain 55–59 amino acids in length which can be aligned on the basis of conserved cysteine, tryptophan and arginine residues (FIGS. 6B and 6C).

Similar domains are present in a small number of proteins (Patthy, 1988; Smith et al., 1991). In particular, the adhesive glycoprotein encoded by the thrombospondin I and II genes (Lawler and Hynes, 1986; Bornstein et al., 1991) each possess 3 of these domains which have been designated thrombospondin type 1 repeats (TSRs) (Lawler and Hynes, 1986) (FIG. 6C). Two TSRs are found in protein C6–C9 of the alternative complement cascade, one at the NH$_2$-terminal and one at the COOH-terminal of each protein (Haefliger et al., 1989; Smith et al., 1991). Moreover, the complement-binding protein properdin, contains 6 TSRs which comprise 80% of the protein (Goundis and Reid, 1988). In addition to these vertebrate proteins, the central core of the TSR is similar to region II of malarial circumsporozoite (CS) and other plasmodial proteins (FIG. 6C) (Rich et al., 1990; Robson et al., 1988) which appear to mediate the binding of malarial sporozoites to host cells in the early stages of parasitic infection (Dame et al., 1984). Finally, two TSRs are present in the C.elegans gene Unc-5, which appears to regulate axonal pathfinding in a subset of neurons (Hedgecock et al., 1990; Culotti et al., 1991). The organization of cysteine and tryptophan residues in the TSRs of the FP5-9 encoded protein is not similar to that of the NH$_2$-terminal TSRs of the C6–C9 complement proteins (FIG. 6B). However, the core region of the TSRs in FP5-9 (residues 14–19) is most similar to that of thrombospondin, properdin and the malarial CS proteins (FIG. 6B). We have named the FP5-9 gene F-spondin to reflect its high level of expression in the floor plate (see below) and the presence of the TSRs.

The TSRs in thrombospondin promote the adhesion of a variety of different cell types (Prater et al., 1991). Similarly, the TSR core region of the plasmodium vivax CS protein promotes the attachment of human hematopoietic cell lines in vitro (Rich et al., 1990). The amino acid sequence VTCG which is contained within this common motif appears to be critical to the cell adhesive properties of the CS proteins. A VTCG sequence (Seq. ID No. 6) is also present in the two TSRs of thrombospondin that promote cell adhesion (Prater et al., 1991). Strikingly, there is a VTCG in the fourth TSR of F-spondin and the second and third TSRs of F-spondin contain sequences (VSCG, Seq. ID No. 7; ATCG, Seq. ID No. 8) that vary by a single conservative substitution (FIG. 6B). These observations raise the possibility that the TSRs in F-spondin mediate cell adhesion. A search of the Genbank database for other proteins implicated in cell adhesion and recognition that contain a VTCG sequence identified V-CAM1 (Hession et al., 1991) and the VLA4 integrin α subunit (Takada et al., 1989).

Analysis of the predicted amino acid sequence of F-spondin reveals several other structural features that may contribute to the functional properties of the protein. The charged region that is interposed between the fifth and sixth TSRs contains the sequence LRE that has been shown to function as a neuronal cell attachment site in the extracellular matrix glycoprotein S-laminin (Hunter et al., 1989a, b). The first, third, fifth and sixth TSR's of F-spondin contain clusters of basic residues that have been implicated in the binding of proteins to heparin and other sulfated glycosaminoglycans (Cardin and Weintraub, 1989). The first, fourth and fifth TSRs of F-spondin also contain a WSXWS sequence (FIG. 6B) which is present in the variant fibronectin type III repeats found in the receptors for several growth and differentiation factors, including ciliary neurotrophic factor (CNTF), leukemia inhibitory factor (LIF) and the interleukins (ILs) 2–7 (Bazan, 1990; Davis, et al., 1991; Patthy, 1990). The function of the WSXWS motif is unclear although mutation at this site in the IL2 receptor blocks transmembrane signalling (Miyazaki et al., 1991).

Expression Pattern of F-Spondin mRNA

Figure 7A:
Figure 7B:
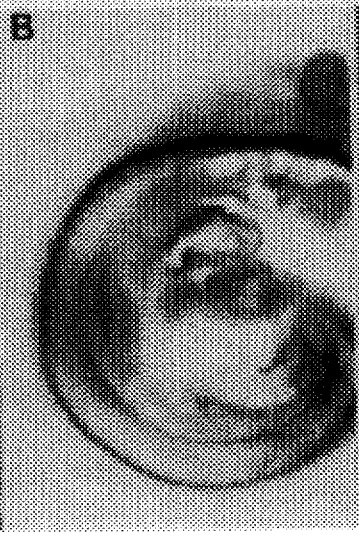

Northern blot analyses of E13 embryos indicate that F-spondin is expressed at much higher levels in the floor plate than in the dorsal spinal cord. More detailed information on the distribution of F-spondin was provided by localizing its mRNA in developing rat embryos by in situ hybridization. F-spondin mRNA was first detected at E10.5 in cells located at the ventral midline of the neural tube at the level of the prospective midbrain, hindbrain and spinal cord (FIG. 7A). At this stage, cells at the ventral midline of the neural tube have acquired floor plate-derived chemoattractant activity (Placzek, et al., 1990c) although no antigenic markers of floor plate differentiation can be detected. The expression of F-spondin mRNA therefore provides an early molecular marker of floor plate differentiation.

Figure 7C:
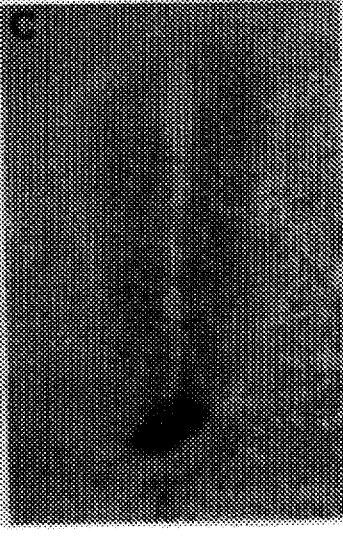
Figure 7D:
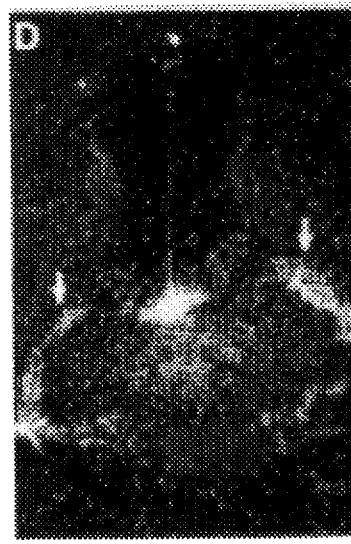
Figure 7E:
Figure 7F:
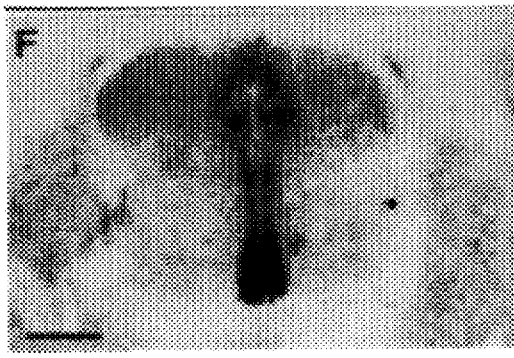
Figure 7G:
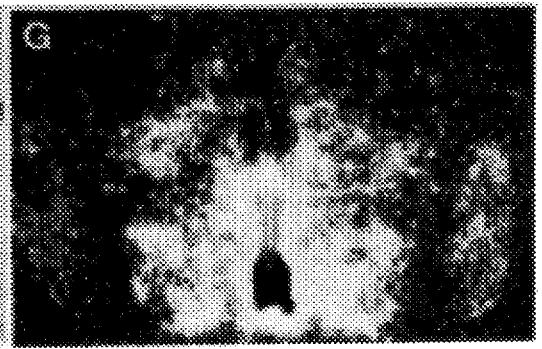
Figure 7H:
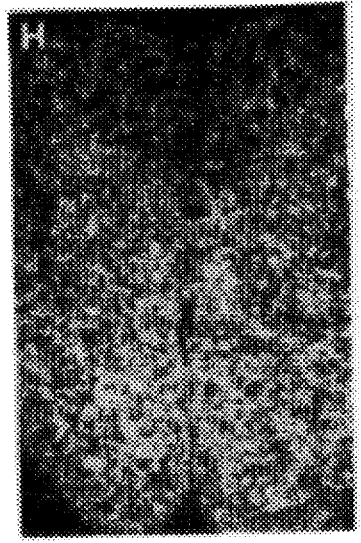

The expression of F-spondin mRNA is maintained at high levels in E11–E12 floor plate (FIG. 7B) whereas other regions of the spinal cord and hindbrain exhibit undetectable levels of hybridization at this stage. By E12–E13 low levels of mRNA are detected in the ventral horn although there is still no detectable mRNA in the dorsal horn (FIGS. 7C and 7D). In addition, the ventral ventricular zone immediately above the floor plate begins to express high levels of F-spondin mRNA (FIG. 7D) whereas hybridization to cells in the ventricular zone in the dorsal half of the spinal cord is not detectable (FIG. 7E). Thus, expression of F-spondin mRNA reveals a molecular difference between ventricular zone cells in the dorsal and ventral spinal cord. Recent studies have suggested that the ventral ventricular zone is the site of origin of oligodendrocyte and astrocyte precursors that subsequently migrate laterally and dorsally to populate the remainder of the spinal cord (Miller, 1991). F-spondin mRNA levels remain high in the floor plate and ventral ventricular zone at E16 and by this stage significant hybridization is also detected in cells in the ventral and intermediate regions of the spinal cord (FIGS. 7F and 7G). By P0, the levels of F-spondin mRNA in the floor plate have decreased and there is an increase in hybridization to other cells in the spinal cord, resulting in an uniform expression of F-spondin mRNA (FIG. 7H). F-spondin mRNA is also preferentially expressed in the floor plate of the E11–E16 hindbrain and midbrain and becomes more widely expressed in the brain at later embryonic stages (not shown).

In addition to the expression of F-spondin in the embryonic CNS, from E11–E12 onwards hybridization is also detected in association with sensory and motor nerve branches that project into the periphery (FIG. 7D). The association with peripheral nerve branches suggests that F-spondin mRNA is expressed in Schwann cells. The expression of F-spondin mRNA in association with peripheral nerves persists until E16, but appears to decrease at later stages, and by P0, little or no hybridization is detected in peripheral nerve (FIG. 3C). These results provide evidence that over the period of initial outgrowth of central and peripheral axons, F-spondin mRNA is expressed predominantly by the floor plate with lower levels of expression in cells of the peripheral nerves, probably Schwann cells.

F-spondin mRNA is also expressed outside the nervous system. In particular, mesodermal cells underlying the ventral midline of the spinal cord express low levels of F-spondin mRNA from E11 (FIG. 7D). In addition, embryonic and P0 kidney (FIG. 3C), lung and condensing cartilage (not shown) expresses F-spondin mRNA. Expression of mRNA in the CNS, lung and kidney persists post-natally and in the adult (not shown).

Secretion and Cell Surface Association of F-Spondin

Figure 8A:
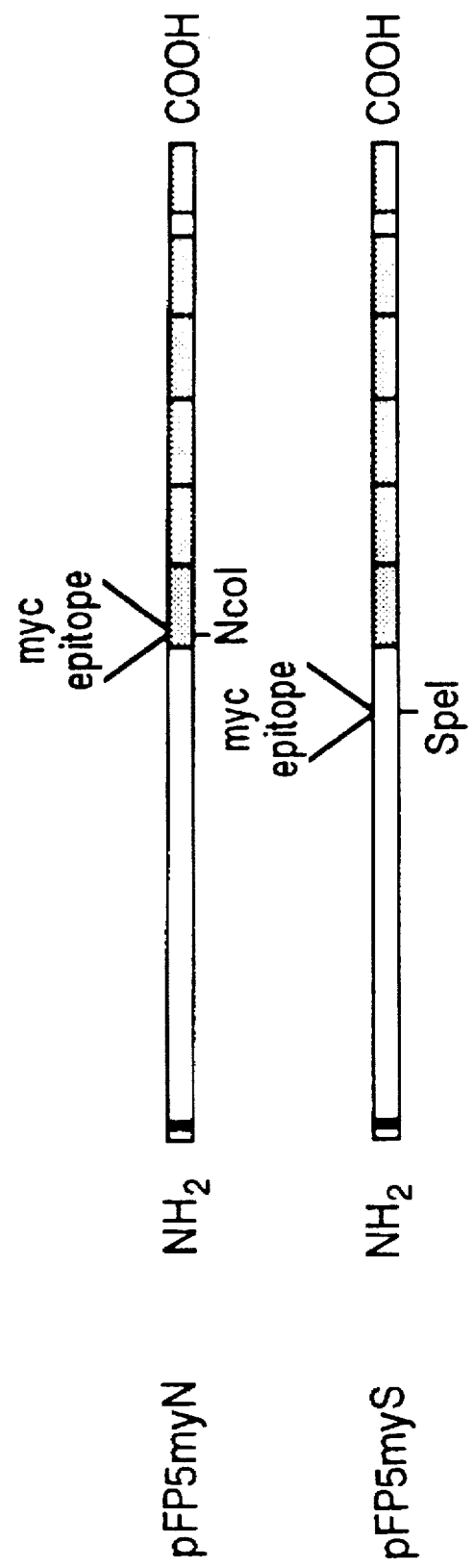

To determine the cellular localization of the F-spondin protein when expressed in mammalian cells, two epitope-tagged derivatives, F-spondin$^{myc}$ were generated, each of which contain a 10 amino acid insert derived from the human c-myc proto-oncogene that can be detected by MAb 9E10 (Evan et al., 1985) (FIG. 8A). The cDNAs encoding F-spondin$^{myc}$ were cloned into a mammalian expression vector and transfected into cos cells. To examine whether F-spondin$^{myc}$ is present in medium conditioned by transfected cells, cos cells were labelled with $^{35}$S-methionine for 3–4 h and the released proteins were immunprecipitated with MAb 9E10. Immunoprecipitates from cos cells transfected with two different F-spondin$^{myc}$ constructs revealed a single major band of 116 kDa that was absent from mock-transfected cells (FIG. 8B). Immunoprecipitation of proteins extracted from the cos cells indicated that the amount of F-spondin recovered from the medium was similar to that associated with the cells (not shown). Thus cos cells release a significant fraction of synthesized F-spondin$^{myc}$. Other myc epitope-tagged proteins, for example the drosophila wingless protein, are synthesized by cos cells but are not detected in the medium (K. Basler, Personal communication) suggesting that the presence of F-spondin$^{myc}$ in the medium does not result from leakage from damaged cells. Thus, under these in vitro conditions F-spondin$^{myc}$ is secreted from cells. The apparent molecular weight of F-spondin determined by SDS-PAGE (116 kDa) is significantly greater than that predicted from the amino acid sequence (90 kDa). This difference in molecular weight may derive, in part, from glycoslyation of the core protein.

The cellular localization of F-spondin$^{myc}$ in transfected cos cells was also determined by immunocytochemistry. High levels of immunoreactivity were associated with the cell surface (FIGS. 8C and 8D) with both F-spondin$^{myc}$ constructs (FIG. 8A). No immunoreactivity was detected on the surface of untransfected cos cells (not shown).

The absence of a membrane spanning region and the presence of multiple heparin attachment sites in F-spondin suggests that the cell surface association of F-spondin$^{myc}$ involves the binding of the secreted protein to the cell surface or extracellular matrix. In support of this, F-spondin$^{myc}$ present in the medium removed from transfected cos cells was found to bind to the surface of untransfected cos cells in vitro (not shown).

F-Spondin Promotes Neural Cell Adhesion and Neurite Outgrowth in vitro

The structural features of F-spondin combined with its secretion and association with the cell surface raise the possibility that F-spondin can promote the adhesion of neural cells and the outgrowth of axons. Since F-spondin is expressed at highest levels in the floor plate, the effect of F-spondin on the adhesion and outgrowth of dorsal spinal cord cells include the population of commissural neurons that project to and across the floor plate was examined. In addition, the expression of F-spondin mRNA in peripheral nerves suggested that the dorsal root ganglion (DRG) neurons might adhere to and extend neurites on F-spondin.

Figure 9A:
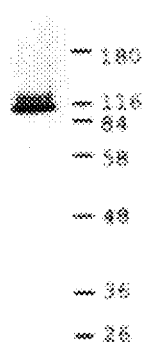
Figure 9B:
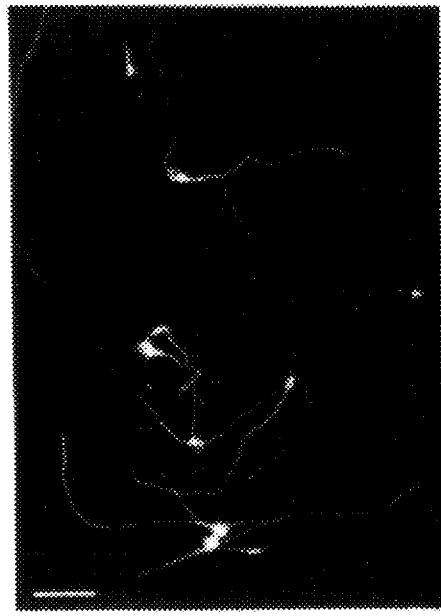
Figure 9C:
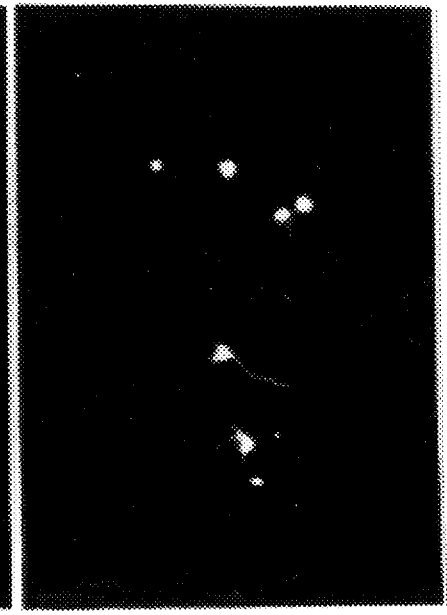
Figure 9D:
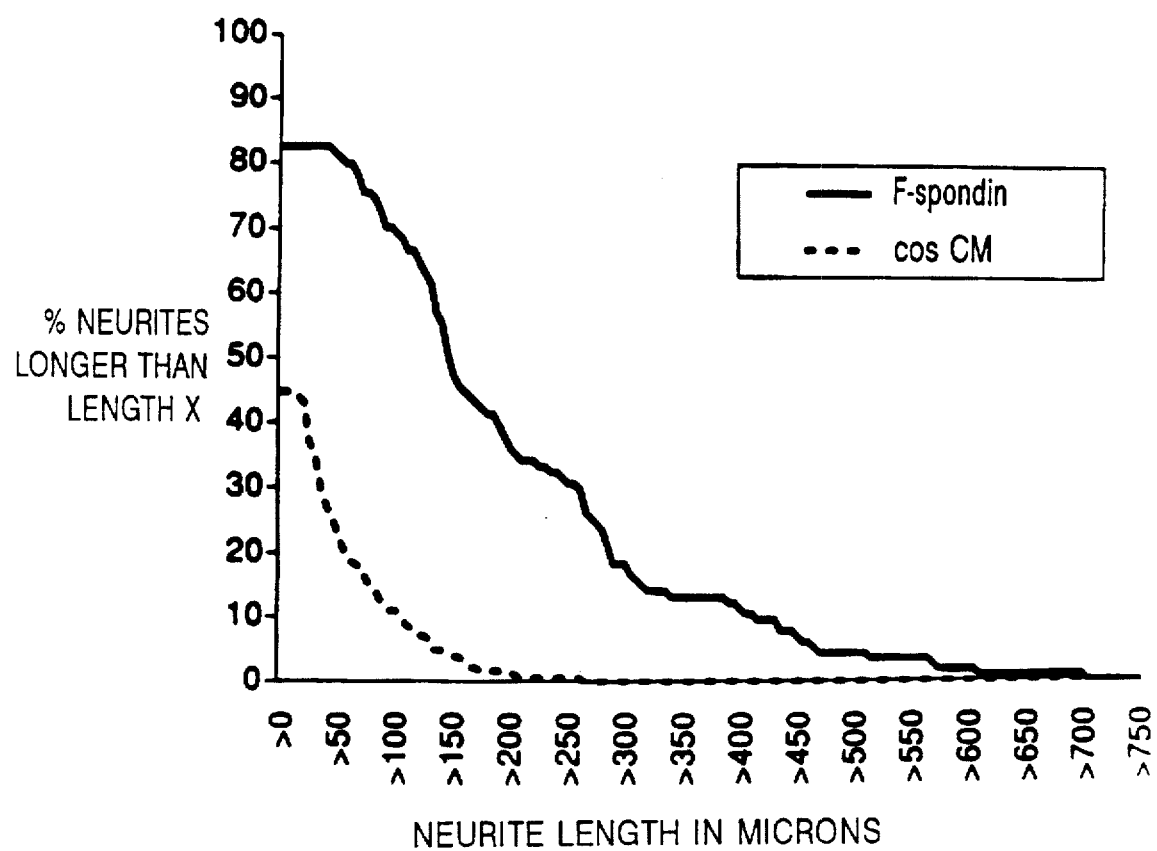

The F-spondin$^{myc}$ protein was purified on a MAb 9E10 affinity column from medium exposed to transfected cos cells (FIG. 9A) and immobilized onto a nitrocellulose substrate (Lemmon et al., 1989). The ability of F-spondin$^{myc}$ to promote the outgrowth of E14 DRG neurons was compared with that of MAb 9E10 affinity-purified proteins secreted from untransfected cos cells and BSA. Outgrowth of DRG neurons on EHS laminin was used as a positive control. Over 80% of DRG neurons extended neurites on F-spondin (FIGS. 9C and 9D) and the length of DRG neurites that extended on F-spondin was similar to that on laminin (not shown) and significantly greater than that on parental cos cell proteins and on BSA (FIGS. 9C and 9D). Similar results were obtained with both versions of F-spondin$^{myc}$ (not shown). In addition, the number of DRG neurons that adhered to a substrate of F-spondin$^{myc}$ after 18 h was about 3 fold greater than that to BSA and parental cos cell proteins, and similar to that on laminin (not shown). These observations provide evidence that F-spondin can promote the adhesion of DRG neurons and the extension of neurites in vitro. The expression of F-spondin by peripheral nerve cells in vivo occurs before many sensory neurons have extended peripheral projections and could therefore contribute to the growth of developing sensory axons in the peripheral nervous system.

Figure 10E:
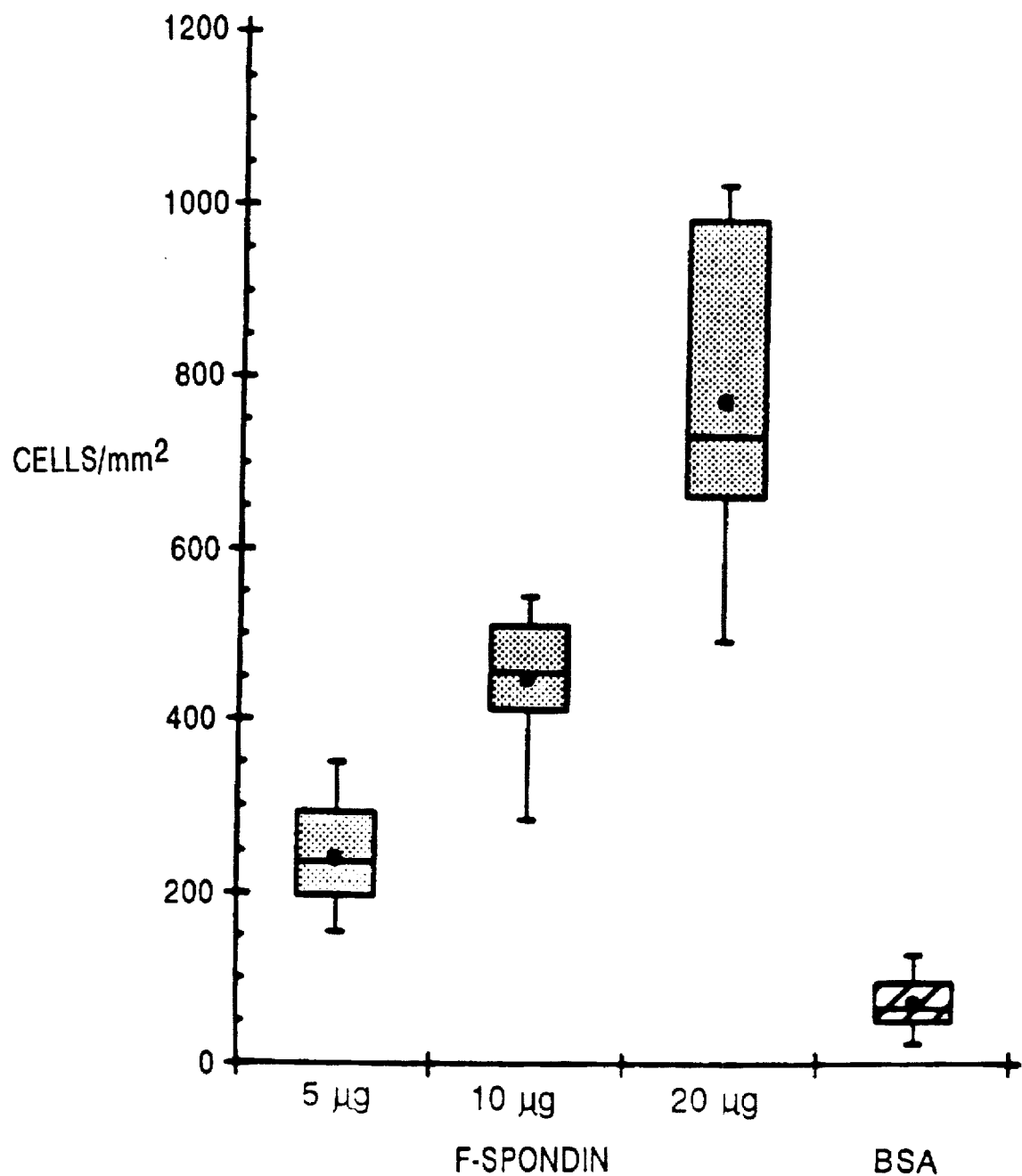

The ability of F-spondin$^{myc}$ to promote the adhesion and outgrowth of dorsal spinal cord cells was also examined. We found that dorsal spinal cord cells adhered well to F-spondin$^{myc}$. Within 60 min (FIGS. 10A and 10E) the number of cells adhering to F-spondin was 10–15 fold greater than that to MAb 9E10 affinity-purified proteins secreted from untransfected cos cells or to BSA (FIGS. 10C and 10E). The majority (>60%) of the adherent cells are neurons as determined by detection of the polysialic acid side chain of NCAM with MAb 5A5 (not shown; see Dodd et al., 1988; Karagogeos et al., 1991). Moreover, many adherent spinal cord neurons extended short neurites during this time period (FIG. 10B). To examine further whether F-spondin promotes the outgrowth of spinal cord neurites the neurite length of adherent spinal cord neurons after 18 h in vitro was determined. The length of spinal cord neurites on F-spondin$^{myc}$ had increased by 18 hours; however neurites outgrowth on purified cos cell proteins and on BSA has also increased significantly and was not detectably different from that on F-spondin$^{myc}$. Thus it remains unclear whether F-spondin promotes extensive neurite outgrowth as well as the adhesion of spinal cord neurons.

Figure 10F:
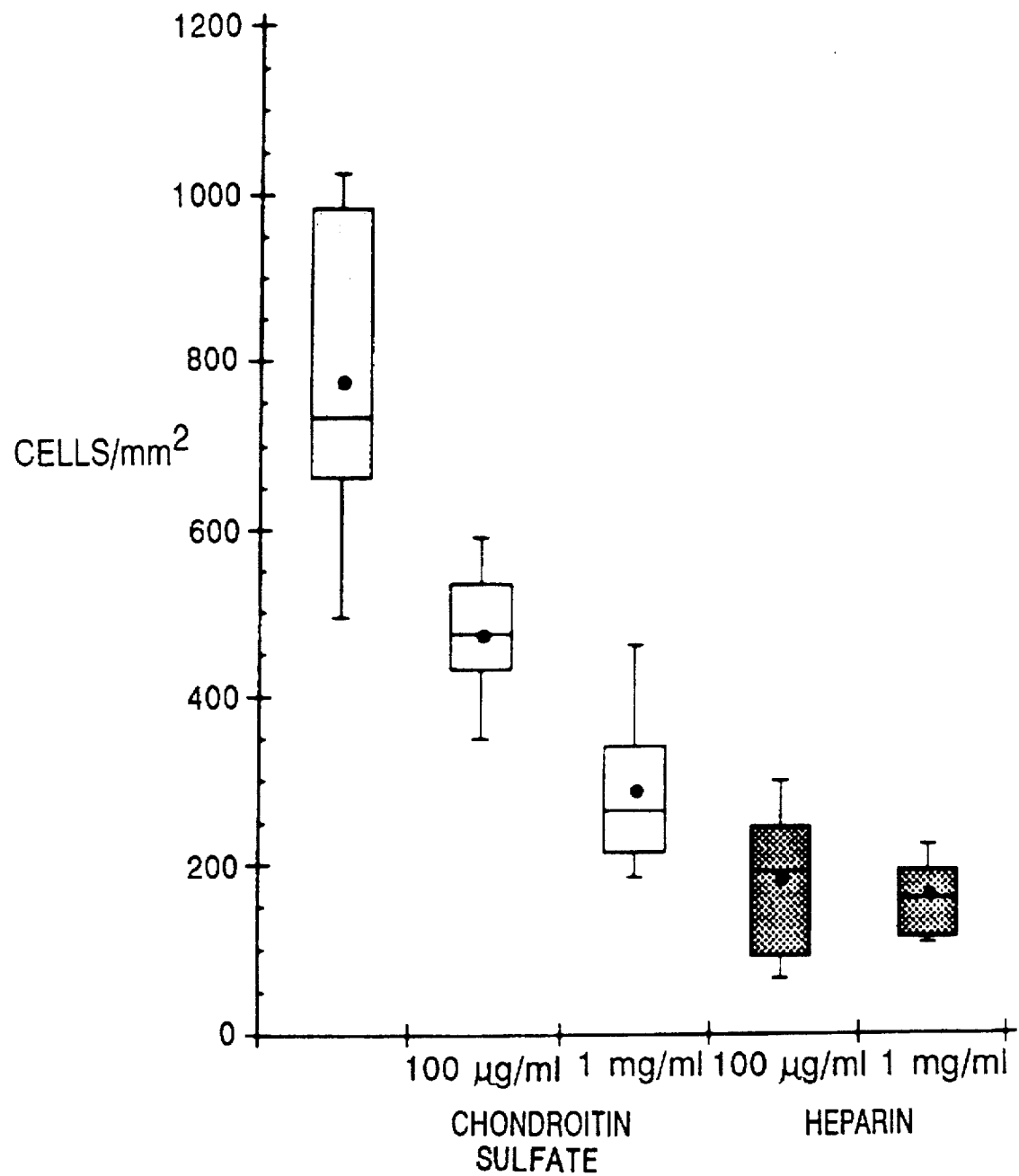

The adhesion of a variety of cell lines to TSRs or to peptide derived from these repeats has been shown to be inhibited by glycosaminoglycans and other sulfated glycoconjugates (Roberts, 1988; Bernfield and Sanderson, 1990; Prater et al., 1991). Moreover, heparin sulfate proteoglycans have been suggested to function as cell surface receptors for thrombospondin (Holt et al., 1984; Sun et al., 1989; Bernfield and Sanderson, 1990). It is possible therefore that the interactions of neural cells with F-spondin may be inhibited by the addition of soluble glycosaminoglycans. It was found that adhesion of dorsal spinal cord neurons to F-spondin was markedly inhibited by heparin, dextran sulfate (not shown) and to a lesser extent by chondroitin sulfate (FIGS. 10D and 10F). To control for non-specific inhibition of the interactions of spinal cord cells with all adhesive substrates, it was determined that spinal cord neurons adhere well to fibronectin and it was found that their adhesion is not significantly affected by concentrations of heparin that block adhesion to F-spondin (not shown). Heparin also reduced to near background levels the adhesion of DRG neurons to F-spondin (not shown). It was not possible to determine whether the outgrowth of neurites from DRG neurons is also blocked by the addition of glycosaminoglycans because heparin caused the detachment of virtually all neurons from the F-spondin substrate, even when added to DRG neurons that had been permitted to settle on F-spondin for 2–3 h.

Experimental discussion

Floor plate cells are located at the ventral midline of the developing nervous system and have been implicated in the control of neural cell identity and in the guidance of developing axons (Jessell and Dodd, 1991). In order to identify genes that might contribute to the functions of the floor plate, subtractive hybridization techniques have been used to isolate cDNA clones encoding a novel protein, F-spondin. F-spondin mRNA expressed at high levels by the developing floor plate and at low or undetectable levels in other regions of the embryonic spinal cord over the period that axons first extend. The predicted structure of F-spondin together with its biochemical properties indicate that it is a secreted glycoprotein with homology to other proteins that mediate cell adhesion and neurite outgrowth. F-spondin promotes the adhesion and outgrowth of axons from embryonic neurons in vitro, suggesting that it may contribute to the growth and guidance of commissural axons at the ventral midline of the spinal cord and of sensory axons in the periphery.

Localization of F-Spondin

Several lines of evidence suggest that the F-spondin protein may be associated with the extracellular matrix. First, F-spondin has several clusters of basic residues that function as glycosaminoglycan binding domains in other secreted proteins. Second, F-spondin is associated with the surface of cos cell transfectants. Third, the complement binding protein properdin, which consists almost entirely of 6 TSRs has been shown to bind sulfated glycoconjugates (Holt et al., 1990).

The restricted distribution of F-spondin mRNA in the embryonic nervous system contrasts with that of other secreted glycoproteins which promote neural cell adhesion and neurite outgrowth. For example, the expression of F-spondin mRNA is more restricted than that of thrombospondin I (O'Shea and Dixit, 1988; O'Shea et al., 1990) and of tenascin/cytotactin (Wehrle and Chiqet, 1990) which appears to be widely expressed in the embryonic central nervous system. Similarly, laminin and fibronectin are expressed in many regions of the developing peripheral nervous system (Sanes et al., 1990). One glycoprotein which has a restricted distribution during nervous system development is S-laminin, an isoform of the laminin B chain (Hunter et al., 1989a).

The TSRs of F-Spondin may be Responsible for Neural Cell Adhesion and Axon Extension The domains of F-spondin that mediate neural cell adhesion and neurite extension have not been mapped although several indirect lines of evidence suggest that the TSRs may be involved. First, proteolytic fragments of thrombospondin which contain the TSRs promote the adhesion of melanoma cells and antibodies directed against the TSRs domain block cell adhesion (Prater et al., 1991). Second, both native thrombospondin and a 140 kDa proteolytic fragment which includes the TSR domains promote the outgrowth of neurites from central and peripheral neurons in vitro (Osterhout and Higgins, 1990; Osterhout et al., 1992; Neugebauer et al., 1991; O'Shea et al., 1991). In addition, antibodies directed against the TSR domains block neurite outgrowth on thrombospondin (Osterhout and Higgins, 1990; Osterhout et al., 1992). Third, the plasmodial CS proteins, which contain the core domain of the TSRs also promote the adhesion of a wide variety of mammalian cells (Rich et al., 1990).

The adhesive properties of the CS proteins have been mapped to the VTCG (SEQ ID NO: 6) sequence (Rich et al., 1990). In addition, the two peptides derived from the TSRs in thrombospondin that are potent attachment factors for melanoma cells also contain the VTCG (SEQ ID NO: 6) sequence whereas the peptide derived from the third TSR which does not contain this sequence is not adhesive (Prater et al., 1991). Thus, the presence of a VTCG (SEQ ID NO: 6) in the fourth TSR of F-spondin suggests that this domain could be involved in the adhesive properties of F-spondin. Nevertheless, other domains within F-spondin may be involved in neural cell adhesion or neurite outgrowth. For example, the region interposed between the fifth and sixth TSR repeats of F-spondin contains an LRE sequence that mediates the neuronal attachment properties of S-laminin (Hunter et al., 1989b).

The ability of neural cells to adhere to and extend neurites on F-spondin suggests that there are neural receptors for this protein. The inhibition by heparin of the adhesion of dorsal spinal cord cells and DRG neurons to F-spondin suggests that proteoglycans may constitute neuronal F-spondin receptors or may regulate receptor function.

The conservation of TSRs in F-spondin and thrombospondin also raises the possibility that receptors for the TSR domains of thrombospondin may interact with the related domains of F-spondin. There is evidence that the TSRs of thrombospondin can interact with 3 distinct classes of cellular receptors (Frazier, 1991). First, thrombospondin and a VTCG-containing peptide (SEQ ID NO: 6) from the TSR core region can bind to an 88 kDa membrane glycoprotein, GPIV, or CD36, which is present on many cell types (Asch et al., 1990, 1991). Second, thrombospondin can bind to sulfated glycoconjugates including the heparin sulfate proteoglycan syndecan (Roberts, 1988; Sun et al., 1989; Holt et al., 1989; Bernfied and Sanderson, 1990). In addition, the adhesion of cells to VTCG-containing peptides (SEQ ID NO: 6) derived from the TSR domains of thrombospondin and plasmodial CS proteins can be inhibited by heparin and other glycosaminoglycans (Holt et al., 1990; Prater et al., 1991; Rich et al., 1991). Third, antibodies against integrins block neurite outgrowth on thrombospondin (Neugebauer et al., 1991). Since antibodies to the TSR domains of thrombospondin block the outgrowth of neurites on thrombospondin (Osterhout and Higgins, 1990; Osterhout et al., 1992) it is possible that sequences within the TSRs interact with neuronal integrins.

Possible Functions of F-Spondin in Neural Development

The most prominent expression of F-spondin in the embryonic nervous system is in the floor plate, an epithelial cell group that has been implicated in several aspects of spinal cord development. Midline neural plate cells that give rise to the floor plate undergo marked cell shape changes during the closure of the neural tube. Thus, one possible function of F-spondin could be to mediate adhesive interactions between floor plate cells that maintain the integrity of the floor plate during the formation of the embryonic spinal cord. The expression of F-spondin mRNA in floor plate cells is highest at the time that the floor plate has been suggested to have roles in the chemotropic (Tessier-Lavigne et al., 1988; Placzek et al., 1990a) and contact (Dodd et al., 1988) guidance of commissural axons. It is found that recombinant F-spondin$^{myc}$ secreted from cos cells does not mimic the ability of the floor plate derived chemoattractant to promote the outgrowth of commissural axons from dorsal spinal cord explants (Klar, Placzek, Tessier-Lavigne, Dodd and Jessell, unpublished observations). This suggests that F-spondin may not be involved in the long-range guidance of commissural axons to the floor plate, at least through chemotropism.

F-spondin could be involved in the contact-dependent guidance of commissural axons once they reach the ventral midline of the spinal cord under the influence of chemotropic guidance cues. The growth cones of commissural neurons cross the midline by growing between the basal surface of floor plate cells and the underlying basal lamina (Kuwada et al., 1990; Yaginuma et al., 1991). F-spondin secreted by the floor plate may accumulate at high levels in association with the basal surface of floor plate cells or with the underlying basal lamina thus generating a difference in adhesive properties of the floor plate and the lateral neuroepithelium. The growth cones of commissural neurons may adhere preferentially to F-spondin, prompting them to change trajectory at the boundary of the floor plate and lateral neuroepithelium. It is also possible that F-spondin has a more active signalling role which induces changes in the properties of commissural growth cones that permits them to respond to other midline guidance cues. Several proteins are expressed selectively on the surface of floor plate cells at this stage of spinal cord development (Dodd and Jessell, 1988; Chuang and Lagenaur, 1990) and could provide cues that contribute to the guidance of commissural axons at the midline.

F-spondin mRNA is also expressed by cells in the peripheral nerve, presumably Schwann cells, from E11 to E16 over the period that motor and sensory axons project to their peripheral targets. Non-neuronal cells in peripheral nerve are known to secrete a variety of extracellular matrix glycoprotein, including laminin and fibronectin that can promote the growth of developing axons. Antibody inhibition studies have provided evidence for the existence of additional molecules that mediate neuronal outgrowth on peripheral nerve substrates (Tuttle et al., 1989). The ability of recombinant F-spondin to promote the outgrowth of embryonic sensory neurons in vitro suggests that the protein may be released by non-neuronal cells in the peripheral nerve and could contribute to the initial outgrowth of sensory axons in vivo.

Taken together, the present studies identify F-spondin as a novel secreted protein with potential roles in neural cell adhesion and neurite outgrowth in vivo. The development of antibodies that recognize native F-spondin will be important in determining the localization of the protein within the nervous system and in assessing its function in more detail.

REFERENCES

1. Asch, A. S., Heimer, E. and Nachman, R. L. (1990) An amino acid sequence motif in thrombospondin is responsible for CD36 binding. Blood 76:445a, Suppl. 1.
2. Asch, A. S., Tepler, J., Silbiger, S. and Nachman, R. L. (1991) Cellular attachment to thrombospondin: Cooperative interactions between receptor systems. J. Biol. Chem. 226:1740–1745.
3. Bazan, J. F. (1990) Structural design and molecular evolution of cytokine receptor superfamily. Proc. Natl. Acad. Sci. 87:6934–6938.
4. Bernfield, M. and Sanderson, R. D. (1990) Syndean, a developmentally regulated cell surface proteoglycan that binds extracellular matrix and growth factors. Philos. Trans. R. Soc. Lond. 327:171–186.
5. Bernhardt, R. R. and Kuwada, J. Y. (1990) Floor plate ablations induces axonal pathfindings errors by spinal commissural cells in the zebrafish embryo. Soc. Neurosci. Abst. 16:139.2.
6. Bornstein, P., O'Rourke, K., Wikstrom, K., Wolff, F. W., Katz, R., Li, P. and Dixit, V. M. (1991) A second, expressed thrombospondin gene (Thbs2) exists in the mouse genome. J. Biol. Chem 266:12821–12824.
7. Bovolenta, P. and Dodd, J. (199) Guidance of Commissural growth cones at the floor plate in the embryonic rat spinal cord. Development 109:435–447.
8. Bovolenta, P. and Dodd, J. (1991) Perturbation of neuronal differentiation and axon guidance in the spinal cord of mouse embryos lacking a floor plate: Analysis of Danforth's short-tail mutation. Development 113:625–639.
9. Cardin, A. D. and Weintraub, H. J. R. (1989) Molecular modeling of protein-glycosaminoglycan interactions. Arteriosclerosis 9:21–32.
10. Chuang, W. and Lagenaur, C. F. (1990) Central nervous system antigen P84 can serve as a substrate for neurite outgrowth. Dev. Biol. 137:219–232.
11. Culotti, J. G., Spence, A., Zhou, Y., Scott, I., Leugn-Hagesteijn, C., Stern, B. and Hedgecock, E. (1991) The unc-5 axon guidance gene of C. elegans has features of a cell adhesion receptor. J. Cell Biol. 115:122a.
12. Dame, J. B., Williams, J. L., McCutchan, T. F., Weber, J. L., Writz, R. A., Hockmeyer, W. T., Maloy, W. L., Haynes, J. D., Schneider, I., Roberts, D., Sanders, G. S., Reddy, E. P., Diggs, C. L. and Miller, L. H. (1984) Structure of the gene encoding the immunodominant surface antigen on the sporozoite of the human malaria parasite plasmodium falciparum. Science 225:593–599.
13. Davis, S., Aldrich, T. H., Valenzuela, D. M., Wong, V. V., Furth, M. E., Squinto, S. P. and Yancopoulos, G. D. (1991) The receptor for ciliary neurotrophic factor. Science 253:59–63.
14. Dodd, J. and Jessell, T. M (1985) Lactoseries carbohydrates specify subsets of dorsal root ganglion neurons and projecting to the superficial dorsal horn of rat spinal cord. J. Neurosci. 6:3278–3294.
15. Dodd, J. and Jessell, T. M (1988) Axon guidance and the patterning of neuronal projections in vertebrates. Science 242:692–699.
16. Dodd, J., Morton, S. B., Karagogoes, D., Yamamoto, M. and Jessell, T. M. (1988) Spatial regulation of axonal glycoprotein expression on subsets of embryonic spinal neurons. Neuron 1:105–116.
17. Evan, G. I., Lewis, G. K., Ramsay, G., Bishop, J. M. (1985) Isolation of monoclonal antibodies specific for human c-myc proto-oncogene product. Mol. Cell. Biol. 5:3610–3616.
18. Feinberg, A. P. and Volgelsten, B. (1983) A technique for radiolabelling DNA restriction endonuclease fragments to high specific activity. Anal. Biochem. 132:6–13.
19. Frazier, W. A. (1991). Thrombospondins. Current Opinions in Cell Biology 3:792–799.
20. Furley, A. J., Morton, S. B., Manalo, D., Karagogeos, D., Dodd, J. and Jessell, T. M. (1990) The axonal glycoprotein TAG-1 is an immunoglobulin superfamily member with neurite outgrowth-promoting activity. Cell 61:157–170.
21. Goundis, D. and Reid, K. B. M. (1988) Properdin, the terminal complement components, thrombospondin and the circumsporozoite protein of malaria parasites contain similar sequence motifs. Nature 335:62–65.
22. Haefliger, J-A., Tschopp, J., Vial, N. and Jennet, D. E. (1989) Complete primary structure and functional characterization of the sixth component of the human complement system. J. Biol. Chem. 264:18041–18051.

23. Harland, R. M. (1991) In situ hybridization: an improved whole mount method for Xenopus embryos. Methods in Cell Biology 36:675–685.
24. Harlow, E. and Lane, D. (1988) Antibodies: A Laboratory Manual. Cold Spring Harbor Laboratory.
25. Hatta, K., Kimmel, C. B., Ho, R. K. and Walker, C. (1991) The cyclops mutation blocks specification of the floor plate of the zebrafish central nervous system. Nature 350:339–341.
26. Hedgecock, E. M., Culotti, J. G. and Hall, D. H. (1990) The unc-5, unc-6 and unc-40 genes guide circumferential migrations of pioneer axons and mesodermal cells on the epidermis in C. Elegans. Neuron 2:61–85.
27. Hedgecock, E. M. and Hall, D. H. (1990) Homologies in the neurogenesis of nematodes, arthropods and chordates. Seminar in Neurosci. 2:159–172.
28. Hession, C., Tizard, R., Vassallo, C., Schiffer, S. B., Goff, D., Moy, P., Chi-Rosso, G., Luhowskyj, S., Lobb, R. and Osborn, L. (1991) Cloning of an alternate form of vascular cell adhesion molecule-1 (VCAM1). J. Biol. Chem. 266:6682–6685.
29. Holley, J. and Silver, J. (1987) Growth pattern of pioneering chick spinal cord axons. Devl. Biol. 123:375–388.
30. Holdt, G. D., Kaesberg, P. R., Ershler, W. B., Esko, J. D. and Mcsher, D. F. (1989) Chinese hamster ovary cell adhesion to human platelet thrombospondin is dependent on cell surface heparan sulfate proteoglycan. 83:994–1001.
31. Holt, G. D., Pangburn, M. K. and Ginsburg, V. (1990) Properdin binds to sulfatide [Gal(3-SO$_4$)B1-1Cer] and has a sequence homology with other proteins that bind sulfated glycoconjugates. J. Biol. Chem. 265:2852–2855.
32. Hunter, D. D., Shah, V., Merlie, J. P. and Sanes, J. R. (1989b) A laminin-like adhesive protein concentrated in the synaptic cleft of the neuromuscular junction. Nature 338:229–233.
33. Hunter, D. D., Porter, B. E., Bulock, J. W., Adams, S. P., Merlie, J. P. and Sanes, J. R. (1989) Primary sequence of a motor neuron-selective adhesive site in the synaptic basal lamina protein S-laminin. Cell 59:905–913.
34. Jessell, T. M. and Dodd, J. (1991) Floor plate-derived signals and the control of neural cell pattern in vertebrates. Harvey Lecture Series (In Pres).
35. Karagogeos, D., Morton, S. B., Casano, F., Dodd, J. and Jessell, T. M. (1991) Developmental expression of the axonal glycoprotein TAG-1: Differential regulation by central and peripheral neurons in vitro. Development 112:61–67.
36. Klambt, C., Jacobs, J. R. and Goodman, C. S. (1991) The midline of the drosophila central nervous system: a model for the genetic analysis of cell fate, cell migration and growth cone guidance. Cell 64:801–815.
37. Kozak, M. (1984) Compilation and analysis of sequences upstream from the translational start site in eukaryotic mRNA. Nucl. Acids Res. 12:857–872.
38. Kuwada, J. Y., Bernhardt, R. R. and Nguyen, N. (1990) Development of spinal neurons and tracts in the zebrafish embryo. J. Comp. Neurol. 302:617–628.
39. Kyte, J. and Doolittle, R. F. (1982) A simple method for displaying the hydropathic character of a protein. J. Mol. Biol. 157:105–132.
40. Lawler, J. and Hynes, R. O. (1986) The structure of human thrombospondin, an adhesive glycoprotein with multiple calcium-binding sites and homologies with several different proteins. J. Cell. Biol. 103:1635–1648.
41. Lemmon, V., Farr, K. L. and Lagenaur, C. (1989) L1-mediated axon outgrowth occurs via a homophilic binidng mechanism. Neuron 2:1597–1603.
42. McKanna, J. A. and Cohen, S. (1989) The EGF receptor kinase substrate p35 in the floor plate of the embryonic rat CNS. Science 243:1477–1479.
43. Miller, R. H. (1991) Ventral origin of A2B5-immunoreactive glial precursor cells in the developing rat spinal cord. Soc. Neuro. Sci. Abst. 17:235.
44. Miyazaki, T., Maruyama, M., Yamada, G., Hatakeyama, M. and Taniguchi, T. (1991) The integrity of the conserved 'WS motif' common to IL-2 and other cytokine receptors is essential for ligand binding and signal transduction. The EMBO Journal 10:3191–3197.
45. Nambu, J. R., Lewis, J. O., Wharton, K. A. and Crews, S. T. (1991) The drosophila single-minded gene encodes a helix-loop-helix protein that acts as a master regulator of CNS midline development. Cell 67:1157–1167.
46. Neugebauer, K. M., Emmett, C. J., Venstrom, K. A. and Reichardt, L. F. (1991) Vitronectin and thrombospondin promote retinal neurite outgrowth: Developmental regulation and role of integrins. Neuron 6:345–358.
47. O'Shea, K. S. and Dixit, V. M. (1988) Unique distribution of the extracellular matrix component thrombospondin in the developing mouse embryo. J. Cell Biol. 107:2737–2748.
48. O'Shea, K. S. and Rheinheimer, J. S. T. and Dixit, V. M. (1990) Deposition and role of thrombospondin in the histogenesis of the cerebellar cortex. J. Cell Biol. 110:1275–1283.
49. O'Shea, K. S., Liu, L-H. J. and Dixit, V. M. (1991) Thrombospondin and a 140 kd fragment promote adhesion and neurite outgrowth from embryonic central and peripheral neurons and from PC12 cells. Neuron 7:231–237.
50. Osterhout, D. J. and Higgins, D. (1990) Thrombospondin promotes axonal growth in sympathetic neurons. Soc. Neurosci. Abst. 16:312.
51. Osterhout, D. J., Frazier, W. A. and Higgin, D. (1992) Thrombospondin promotes process outgrowth in neurons from the peripheral and central nervous systems. Dev. Biol. In Press.
52. Patthy, L. (1990) Homology of a domain of the growth hormon/prolactin receptor family with type III modules of fibronectin. Cell 61:13–14.
53. Patthy, L. (1988) Detecting distant homologies of mosaic proteins. Analysis of the sequences of thrombomodulin, thrombospondin complement components C9, C8 alpha and C8 beta, vitronectin and plasma cell membrane glycoprotein PC-1. J. Mol. Biol. 202:689–696.
54. Perkins, S. J., Nealis, A. S., Haris, P. I., Chapman, D., Goundis, D. and Reid, K. B. M. (1989) Secondary structure in properdin of the complement cascades and related proteins: A study by fourier transforms infrared spectroscopy. Biochemistry 28:7176–7182.
55. Placzek, M., Tessier-Lavigne, M., Jessell, T. M. and Dodd, J. (1990a) Orientation of Commissural axons in vitro in response to a floor plate derived chemoattractant. Development 110:19–30.
56. Placzek, M., Tessier-Lavigne, M., Yamada, T., Jessell, T. M. and Dodd, J.(1990b) The guidance of developing axons by diffusible chemoattractants. Cold Spring Harbor Symp 55:279–988.
57. Placzek, M., Tessier-Lavigne, M., Yamada, T., Jessell, T. M. and Dodd, J. (1990c) Mesodermal control of neural cell identity: floor plate induction by the notochord. Science 250:985–988.
58. Placzek, M., Yamada, T., Tessier-Lavigne, M., Jessell, T. M., Dodd, J. (1991) Control of dorso ventral pattern in vertebrate neural development: induction and polarizing properties of the floor plate. Development (In Press).

59. Prater, C. A., Plotkin, J., Jaye, D. and Frazier, W. A. (1991) The properdin-like type I repeats of a human thrombospondin contain a cell attachment site. J. Cell Biol. 112:1031–1040.

60. Rich, K. A., George, F. W., Law, J. L. and Martin, W. J. (1990) Cell-adhesive motif in region II of malarial circumsporozoite protein. Science 249:1574–1577.

61. Rich, K. A., Hinton, D. R. and Blanks, J. B. (1991) Attachment of developing mouse retinal and lens cells to a sequence common to thrombospondin and malarial proteins. J. Cell Biol. 115:441a.

62. Roberts, D. D. (1988) Interactions of thrombospondin with sulfated glycolipids and proteoglycans of human melanoma cells. Cancer Research 48:6785–6793.

63. Robson, K. J. H., Hall, J. R. S., Jennings, M. W., Harris, T. J. R., Marsh, K., Newbold, C. I., Tate, V. E., Weatherall, D. J. (1988) A highly conserved amino-acid sequence in thrombospondin, properdin and in proteins from sporozoites and blood stages of a human malaria parasite. Nature 335:79–82.

64. Romijin, H. J., Gabets, A. M. M. C., Mud, M. T. and Walter, P. S. (1982) Nerve outgrowth, synaptogenesis and bioelectric activating in rate cerebral cortex tissue cultured in serum-free, chemically defined medium. Devl. Brain. Res. 2:583–589.

65. Sambrook, J., Fritsch, E. F. and Maniatis, T. (1989) Molecular Cloning. Cold Spring Harbor Laboratory Press.

66. Sanes, J. r., Engvall, E., Butkowski, R. and Hunter, D. D. 91990) Molecular heterogeneity of basal laminae: Isoforms of laminin and collagen IV at the neuromuscular junction and elsewhere. J. Cell Biol. 111:1685–1699.

67. Sanger, F., Nicklen, S. and Coulson, A. R. (1988) DNA sequencing with chain-terminating inhibitors. Proc. Natl. Acad. Sci. 74:5463.

68. Schachner, M., Antonicek, H., Fahrig, T. et al. (1990) Families of neural cell adhesion molecules. In Morphoregulatory Molecules (eds. G. M. Edelman, B. A. Cunningham and J. P. Thiery) John Wiley and Sons, New York, pp. 443–468.

69. Sive, H. L. and John, T. S. (1988) A simple subtractive hybridization technique employing photoactivatable biotin and phenol extraction. Nucl. Acids. Res. 16:10937.

70. Smith, K. F., Nolan, K. F., Reid, K. B. M. and Perkins, S. J. (1991) Neutron and X-ray scattering studies of the human complement protein properdin provide an analysis of the thrombospondin repeat. Biochemistry 30:8000–80008.

71. Steiner, D. F. (1991) Prohormone convertases revealed at last. Current Biology 1:375–377.

72. Sun, X., Mosher, D. F. and Rapraeger, A. (1989) Heparan sulfate-mediated binding of epithelial cell surface proteoglycan to thrombospondin. J. Biol. Chem 264:2885–2889.

73. Takada, Y., Elices, M. J., Crouse, C., Hemler, M. E. (1989) The primary structure of the a subunit of VLA-4: homology to other integrins and a possible cell-cell adhesion function. EMBO J. 8:1361–1368.

74. Tessier-Lavigne, M. and Paczek, M. (1991) Target attraction: are developing axons guided by chemotropism? Trends in Neuroscience 14:303–310.

75. Tessier-Lavigne, M., Placzek, M., Lumsden, A. G. S., Dodd, J. and Jessell, T. M. (1988) Chemotropic guidance of developing axons in the mammalian central nervous system. Nature 335:775–778.

76. Thomas, P. (1983) Hybridization of denatured RNA transferred or dotted onto nitrocellulose paper. Meth. Enzymol. 100:255–266.

77. Tuttle, R., Sandrock, A. W. and Matthew, W. D. (1989) Analysis of complex matrices functional in neuronal process extension using monoclonal antibodies in vitro and in vivo. Dev. Neurosci. 11:289–299.

78. van Straaten, H. W. M., Hekking, J. W. M., Wiertz-Hoessels, E. L., Thors, F. and Drukker, J. (1988) Effect of the notochord on the differentiation of a floor plate area in the neural tube of the chick embryo. Anat. Embryol. 177:317–324.

79. von Heijine, G. (1985) Signal sequences: the limits of variation. J. Mol. Biol. 184:99–105.

80. Wagner, M., Thaller, C., Jessell, T. M. and Eichele, G. (1990) Polarizing activity and retinoid synthesis by the floor plate of the neural tube. Nature 345:819–822.

81. Weber, A. (1938) Croissance de fibres nerveuses commissurales lors de lesion de la moelle epiniere chez de jeunes embryons de poulet. Biomorphosis 1:30–35.

82. Wehrle, B. and Chiqet M. (1990) Tenascin is accumulated along developing peripheral nerves and allows neurite outgrowth in vitro. Development 110:401–415.

83. Wilkinson, D. G., Bailes, J. A., Champion, J. E. and McMahon, A. P. (1987) A molecular analysis of mouse development from 8 to 10 days post coitum detects changes only in embryonic globin expression. Development 99:493–500.

84. Yaginuma, H., Homma, S., Kunzi, L. and Oppenheim, R. W. (1991) Pathfinding by growth cones of commissural interneurons in the chick embryo spinal cord: a light and electric micropscopic study. J. Comp. Neurol. 304:78–102.

85. Yaginuma, H. and Oppenheim, R. W. (1991) An experimental analysis of in vitro guidance cues used by axons of spinal interneurons in the chick embryo: evidence for chemotropism and related guidance mechanisms. J. Neuroscience 11:2598–2613.

86. Yamada, T., Placzek, M., Tanaka, H., Dodd, J. and Jessell, T. M. (1991) Control of cell pattern in the developing nervous system: Polarizing activity of the floor plate and notochord. Cell 64:635–647.

What is claimed is:

1. A method of producing a F-spondin polypeptide which comprises growing a host vector system comprising an isolated nucleic acid molecule encoding vertebrate F-spondin, under conditions permitting production of the polypeptide and recovering the polypeptide so produced.

2. A F-spondin polypeptide produced by the method of claim 1.

3. Purified, vertebrate F-spondin polypeptide.

4. A method of attaching nerve cells to a matrix comprising contacting the matrix with nerve cells and purified vertebrate F-spondin at a concentration effective to effect attachment of the cells to the matrix.

5. A method of stimulating outgrowth of a nerve cell comprising administering purified vertebrate F-spondin to the nerve cell at a concentration effective to stimulate outgrowth of the nerve cell.

6. A pharmaceutical composition comprising a pharmaceutically acceptable carrier and purified vertebrate F-spondin.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 36 base pairs (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:1:

CTAGCGAGCA GAAGCTGATC TCCGAGGAGG ACCTCA    36

(2) INFORMATION FOR SEQ ID NO:2:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:2:

CTAGTGAGGT CCTCCTCGGA GATCAGCTTC TGCTCG    36

(2) INFORMATION FOR SEQ ID NO:3:

(i) SEQUENCE CHARACTERISTICS:
                (A) LENGTH: 10 amino acids
                (B) TYPE: amino acid
                (C) STRANDEDNESS: single
                (D) TOPOLOGY: linear (ii) MOLECULE TYPE: protein (xi) SEQUENCE DESCRIPTION: SEQ ID NO:3:

Glu Gln Lys Leu Ile Ser Glu Glu Asp Leu
        1               5                   10

(2) INFORMATION FOR SEQ ID NO:4:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:4:

CATGGGAGCA GAAGCTGATC TCCGAGGAGG ACCTCG    36

(2) INFORMATION FOR SEQ ID NO:5:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:5:

CATGCGAGGT CCTCCTCGGA GATCAGCTTC TGCTCC    36

(2) INFORMATION FOR SEQ ID NO:6:

(i) SEQUENCE CHARACTERISTICS:
                (A) LENGTH: 4 amino acids
                (B) TYPE: amino acid
                (C) STRANDEDNESS: single
                (D) TOPOLOGY: linear -continued ( i i ) MOLECULE TYPE: protein ( x i ) SEQUENCE DESCRIPTION: SEQ ID NO:6:

```
Val  Thr  Cys  Gly
1
```

( 2 ) INFORMATION FOR SEQ ID NO:7:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:7:

```
Val  Ser  Cys  Gly
1
```

( 2 ) INFORMATION FOR SEQ ID NO:8:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

```
Ala  Thr  Cys  Gly
1
```

( 2 ) INFORMATION FOR SEQ ID NO:9:

( i ) SEQUENCE CHARACTERISTICS:
( A ) LENGTH: 4029 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 226..2647

( x i ) SEQUENCE DESCRIPTION: SEQ ID NO:9:

```
CCCTCCCTCT  TCGCGCTCCT  TCGCCACCGC  CCGCCCCTCA  GCTCCGCTGC  TCGGCTCCGC   60

TCAGAGCAGC  GCAGCTCCGC  AGCCAAAGCG  AGGCGGGCTC  GGGCTCCCCA  CCGCCAGTGC  120

CACCCGGGCT  CCTCCAGCTT  TCGCCTCTGC  AGCTCCCGTC  ACTTGGAGTA  AAAGTGTCCT  180

GACAGGGGTC  TGCAACATCA  GCAGAAAGTT  GGGAGGTCCT  CGAGA ATG AGG CTA          234
                                                  Met Arg Leu
                                                   1

TCT CCC GCG CCC CTG AGG CTT AGC CGG GGT CCG GCG CTG CTG GCC CTG            282
Ser Pro Ala Pro Leu Arg Leu Ser Arg Gly Pro Ala Leu Leu Ala Leu
      5              10                  15

GCG CTG CCC CTG GCC GCA GCG CTC GCT TTC TCG GAT GAG ACC CTG GAC            330
Ala Leu Pro Leu Ala Ala Ala Leu Ala Phe Ser Asp Glu Thr Leu Asp
 20                  25                  30                  35

AAA GTG GCC AAG TCG GAG GGC TAC TGC AGC CGC ATC TTG CGC GCC CAG            378
Lys Val Ala Lys Ser Glu Gly Tyr Cys Ser Arg Ile Leu Arg Ala Gln
             40                  45                  50

GGC ACA CGG CGT GAG GGA TAC ACA GAG TTC AGC CTC CGC GTG GAA GGC            426
Gly Thr Arg Arg Glu Gly Tyr Thr Glu Phe Ser Leu Arg Val Glu Gly
```

|  |  |  |  |  |  |  |  |  |  |  |  |  |  |  |  |  |
|---|---|---|---|---|---|---|---|---|---|---|---|---|---|---|---|---|
|  |  |  |  | 55 |  |  |  |  | 60 |  |  |  |  | 65 |  |  |
| GAC | CCT | GAC | TTC | TAT | AAG | CCA | GGA | AGC | AGC | TAC | CGA | GTG | ACA | CTC | TCG | 474 |
| Asp | Pro | Asp | Phe | Tyr | Lys | Pro | Gly | Ser | Ser | Tyr | Arg | Val | Thr | Leu | Ser |  |
|  |  | 70 |  |  |  |  | 75 |  |  |  |  | 80 |  |  |  |  |
| GCT | GCC | CCT | CCC | TCC | TAC | TTC | AGA | GGC | TTC | ACG | TTA | ATT | GCT | CTC | AAA | 522 |
| Ala | Ala | Pro | Pro | Ser | Tyr | Phe | Arg | Gly | Phe | Thr | Leu | Ile | Ala | Leu | Lys |  |
|  | 85 |  |  |  |  | 90 |  |  |  |  | 95 |  |  |  |  |  |
| GAG | AAC | CGC | GAA | GGC | GAT | AAG | GAA | GAA | GAC | CAC | GCG | GGC | ACC | TTC | CAG | 570 |
| Glu | Asn | Arg | Glu | Gly | Asp | Lys | Glu | Glu | Asp | His | Ala | Gly | Thr | Phe | Gln |  |
| 100 |  |  |  |  | 105 |  |  |  |  | 110 |  |  |  |  | 115 |  |
| ATC | ATA | GAT | GAA | GAA | GAA | ACC | CAG | TTT | ATG | AGT | AAC | TGT | CCT | GTG | GCA | 618 |
| Ile | Ile | Asp | Glu | Glu | Glu | Thr | Gln | Phe | Met | Ser | Asn | Cys | Pro | Val | Ala |  |
|  |  |  |  | 120 |  |  |  |  | 125 |  |  |  |  | 130 |  |  |
| GTC | ACT | GAA | AGC | ACC | CCT | CGG | AGG | AGG | ACA | CGG | ATC | CAG | GTG | TTT | TGG | 666 |
| Val | Thr | Glu | Ser | Thr | Pro | Arg | Arg | Arg | Thr | Arg | Ile | Gln | Val | Phe | Trp |  |
|  |  |  | 135 |  |  |  |  | 140 |  |  |  |  | 145 |  |  |  |
| ATA | GCG | CCA | CCC | ACA | GGG | ACA | GGC | TGT | GTG | ATT | CTG | AAG | GCC | AGC | ATT | 714 |
| Ile | Ala | Pro | Pro | Thr | Gly | Thr | Gly | Cys | Val | Ile | Leu | Lys | Ala | Ser | Ile |  |
|  |  | 150 |  |  |  |  | 155 |  |  |  |  | 160 |  |  |  |  |
| GTA | CAG | AAA | CGC | ATT | ATC | TAT | TTT | CAA | GAC | GAG | GGC | TCC | CTG | ACC | AAG | 762 |
| Val | Gln | Lys | Arg | Ile | Ile | Tyr | Phe | Gln | Asp | Glu | Gly | Ser | Leu | Thr | Lys |  |
| 165 |  |  |  |  | 170 |  |  |  |  | 175 |  |  |  |  |  |  |
| AAG | CTG | TGT | GAA | CAG | GAT | CCC | ACA | CTT | GAT | GGA | GTG | ACG | GAC | AGA | CCG | 810 |
| Lys | Leu | Cys | Glu | Gln | Asp | Pro | Thr | Leu | Asp | Gly | Val | Thr | Asp | Arg | Pro |  |
| 180 |  |  |  |  | 185 |  |  |  |  | 190 |  |  |  |  | 195 |  |
| ATC | TTA | GAC | TGC | TGC | GCC | TGC | GGA | ACT | GCC | AAG | TAC | AGA | CTC | ACG | TTT | 858 |
| Ile | Leu | Asp | Cys | Cys | Ala | Cys | Gly | Thr | Ala | Lys | Tyr | Arg | Leu | Thr | Phe |  |
|  |  |  |  | 200 |  |  |  |  | 205 |  |  |  |  | 210 |  |  |
| TAT | GGG | AAC | TGG | TCG | GAG | AAG | ACT | CAT | CCA | AAG | GAT | TAC | CCT | CGT | CGG | 906 |
| Tyr | Gly | Asn | Trp | Ser | Glu | Lys | Thr | His | Pro | Lys | Asp | Tyr | Pro | Arg | Arg |  |
|  |  |  | 215 |  |  |  |  | 220 |  |  |  |  | 225 |  |  |  |
| GCT | AAT | CAC | TGG | TCT | GCC | ATC | ATT | GGC | GGA | TCC | CAC | TCC | AAG | AAC | TAC | 954 |
| Ala | Asn | His | Trp | Ser | Ala | Ile | Ile | Gly | Gly | Ser | His | Ser | Lys | Asn | Tyr |  |
|  |  | 230 |  |  |  |  | 235 |  |  |  |  | 240 |  |  |  |  |
| GTG | CTG | TGG | GAG | TAC | GGA | GGG | TAT | GCC | AGT | GAA | GGG | GTC | AAG | CAA | GTT | 1002 |
| Val | Leu | Trp | Glu | Tyr | Gly | Gly | Tyr | Ala | Ser | Glu | Gly | Val | Lys | Gln | Val |  |
|  | 245 |  |  |  |  | 250 |  |  |  |  | 255 |  |  |  |  |  |
| GCT | GAA | CTT | GGC | TCA | CCA | GTA | AAA | ATG | GAG | GAA | GAA | ATT | CGA | CAA | CAG | 1050 |
| Ala | Glu | Leu | Gly | Ser | Pro | Val | Lys | Met | Glu | Glu | Glu | Ile | Arg | Gln | Gln |  |
| 260 |  |  |  |  | 265 |  |  |  |  | 270 |  |  |  |  | 275 |  |
| AGT | GAT | GAA | GTC | CTC | ACT | GTC | ATC | AAA | GCC | AAA | GCC | CAG | TGG | CCA | TCC | 1098 |
| Ser | Asp | Glu | Val | Leu | Thr | Val | Ile | Lys | Ala | Lys | Ala | Gln | Trp | Pro | Ser |  |
|  |  |  |  | 280 |  |  |  |  | 285 |  |  |  |  | 290 |  |  |
| TGG | CAG | CCT | GTC | AAT | GTG | AGA | GCA | GCA | CCC | TCA | GCC | GAA | TTC | TCA | GTG | 1146 |
| Trp | Gln | Pro | Val | Asn | Val | Arg | Ala | Ala | Pro | Ser | Ala | Glu | Phe | Ser | Val |  |
|  |  | 295 |  |  |  |  | 300 |  |  |  |  | 305 |  |  |  |  |
| GAC | AGG | ACA | CGC | CAC | TTG | ATG | TCC | TTC | CTA | ACC | ATG | ATG | GGC | CCC | AGT | 1194 |
| Asp | Arg | Thr | Arg | His | Leu | Met | Ser | Phe | Leu | Thr | Met | Met | Gly | Pro | Ser |  |
|  |  | 310 |  |  |  |  | 315 |  |  |  |  | 320 |  |  |  |  |
| CCT | GAC | TGG | AAC | GTG | GGC | CTA | TCT | GCA | GAG | GAT | CTG | TGC | ACC | AAG | GAG | 1242 |
| Pro | Asp | Trp | Asn | Val | Gly | Leu | Ser | Ala | Glu | Asp | Leu | Cys | Thr | Lys | Glu |  |
|  | 325 |  |  |  |  | 330 |  |  |  |  | 335 |  |  |  |  |  |
| TGT | GGC | TGG | GTC | CAG | AAA | GTG | GTG | CAG | GAC | CTA | ATT | CCC | TGG | GAT | GCT | 1290 |
| Cys | Gly | Trp | Val | Gln | Lys | Val | Val | Gln | Asp | Leu | Ile | Pro | Trp | Asp | Ala |  |
| 340 |  |  |  |  | 345 |  |  |  |  | 350 |  |  |  |  | 355 |  |
| GGC | ACG | GAC | AGC | GGG | GTG | ACC | TAC | GAG | TCA | CCA | AAC | AAG | CCC | ACA | ATT | 1338 |
| Gly | Thr | Asp | Ser | Gly | Val | Thr | Tyr | Glu | Ser | Pro | Asn | Lys | Pro | Thr | Ile |  |
|  |  |  |  | 360 |  |  |  |  | 365 |  |  |  |  | 370 |  |  |
| CCT | CAG | GAA | AAA | ATC | CGA | CCC | CTG | ACT | AGT | CTG | GAC | CAT | CCT | CAG | AGT | 1386 |
| Pro | Gln | Glu | Lys | Ile | Arg | Pro | Leu | Thr | Ser | Leu | Asp | His | Pro | Gln | Ser |

-continued

```
                        375                              380                              385
CCT   TTC   TAT   GAC   CCG   GAA   GGT   GGG   TCC   ATC   ACA   CAA   GTG   GCC   AGA   GTC    1434
Pro   Phe   Tyr   Asp   Pro   Glu   Gly   Gly   Ser   Ile   Thr   Gln   Val   Ala   Arg   Val
            390                           395                           400

GTC   ATC   GAG   AGA   ATT   GCC   CGG   AAG   GGA   GAA   CAA   TGC   AAC   ATT   GTA   CCT    1482
Val   Ile   Glu   Arg   Ile   Ala   Arg   Lys   Gly   Glu   Gln   Cys   Asn   Ile   Val   Pro
      405                           410                           415

GAC   AAT   GTG   GAT   GAT   ATT   GTA   GCC   GAC   CTG   GCT   CCA   GAA   GAG   AAA   GAT    1530
Asp   Asn   Val   Asp   Asp   Ile   Val   Ala   Asp   Leu   Ala   Pro   Glu   Glu   Lys   Asp
420                           425                           430                           435

GAA   GAT   GAC   ACC   CCT   GAA   ACC   TGC   ATC   TAC   TCC   AAC   TGG   TCC   CCA   TGG    1578
Glu   Asp   Asp   Thr   Pro   Glu   Thr   Cys   Ile   Tyr   Ser   Asn   Trp   Ser   Pro   Trp
                        440                           445                           450

TCG   GCC   TGC   AGC   TCT   TCC   ACT   TGT   GAA   AAG   GGT   AAG   AGG   ATG   CGG   CAA    1626
Ser   Ala   Cys   Ser   Ser   Ser   Thr   Cys   Glu   Lys   Gly   Lys   Arg   Met   Arg   Gln
                  455                           460                           465

CGC   ATG   CTG   AAG   GCA   CAG   CTG   GAC   CTC   AGT   GTC   CCC   TGT   CCT   GAC   ACC    1674
Arg   Met   Leu   Lys   Ala   Gln   Leu   Asp   Leu   Ser   Val   Pro   Cys   Pro   Asp   Thr
            470                           475                           480

CAG   GAC   TTC   CAG   CCC   TGC   ATG   GGC   CCC   GGC   TGC   AGC   GAT   GAA   GAT   GGC    1722
Gln   Asp   Phe   Gln   Pro   Cys   Met   Gly   Pro   Gly   Cys   Ser   Asp   Glu   Asp   Gly
      485                           490                           495

TCC   ACC   TGT   ACC   ATG   TCG   GAG   TGG   ATC   ACC   TGG   TCA   CCC   TGC   AGT   GTC    1770
Ser   Thr   Cys   Thr   Met   Ser   Glu   Trp   Ile   Thr   Trp   Ser   Pro   Cys   Ser   Val
500                           505                           510                           515

TCG   TGT   GGC   ATG   GGT   ATG   AGG   TCC   CGG   GAG   AGG   TAC   GTG   AAG   CAG   TTC    1818
Ser   Cys   Gly   Met   Gly   Met   Arg   Ser   Arg   Glu   Arg   Tyr   Val   Lys   Gln   Phe
                        520                           525                           530

CCG   GAA   GAC   GGC   TCG   GTG   TGC   ATG   CTG   CCC   ACG   GAA   GAG   ACA   GAG   AAG    1866
Pro   Glu   Asp   Gly   Ser   Val   Cys   Met   Leu   Pro   Thr   Glu   Glu   Thr   Glu   Lys
                  535                           540                           545

TGC   ACG   GTC   AAC   GAG   GAG   TGC   TCT   CCT   AGC   AGC   TGC   CTG   GTG   ACT   GAG    1914
Cys   Thr   Val   Asn   Glu   Glu   Cys   Ser   Pro   Ser   Ser   Cys   Leu   Val   Thr   Glu
            550                           555                           560

TGG   GGT   GAG   TGG   GAT   GAC   TGC   AGC   GCC   ACC   TGT   GGA   ATG   GGC   ATG   AAG    1962
Trp   Gly   Glu   Trp   Asp   Asp   Cys   Ser   Ala   Thr   Cys   Gly   Met   Gly   Met   Lys
565                           570                           575

AAG   CGG   CAC   CGC   ATG   GTC   AAG   ATG   AGC   CCC   GCG   GAC   GGC   TCC   ATG   TGC    2010
Lys   Arg   His   Arg   Met   Val   Lys   Met   Ser   Pro   Ala   Asp   Gly   Ser   Met   Cys
580                     585                           590                           595

AAG   GCG   GAG   ACT   TCG   CAG   GCG   GAG   AAA   TGC   ATG   ATG   CCT   GAG   TGC   CAT    2058
Lys   Ala   Glu   Thr   Ser   Gln   Ala   Glu   Lys   Cys   Met   Met   Pro   Glu   Cys   His
                        600                           605                           610

ACC   ATC   CCG   TGC   TTG   CTG   TCT   CCT   TGG   TCC   GAG   TGG   AGC   GAC   TGT   AGC    2106
Thr   Ile   Pro   Cys   Leu   Leu   Ser   Pro   Trp   Ser   Glu   Trp   Ser   Asp   Cys   Ser
                  615                           620                           625

GTG   ACC   TGT   GGG   AAG   GGC   ATG   CGG   ACG   CGC   CAG   CGG   ATG   CTC   AAG   TCT    2154
Val   Thr   Cys   Gly   Lys   Gly   Met   Arg   Thr   Arg   Gln   Arg   Met   Leu   Lys   Ser
            630                           635                           640

CTG   GCA   GAG   CTG   GGG   GAC   TGT   AAT   GAG   GAT   CTG   GAG   CAG   GCG   GAG   AAG    2202
Leu   Ala   Glu   Leu   Gly   Asp   Cys   Asn   Glu   Asp   Leu   Glu   Gln   Ala   Glu   Lys
      645                           650                           655

TGT   ATG   CTG   CCA   GAG   TGC   CCC   ATT   GAC   TGC   GAA   CTC   AGT   GAG   TGG   TCC    2250
Cys   Met   Leu   Pro   Glu   Cys   Pro   Ile   Asp   Cys   Glu   Leu   Ser   Glu   Trp   Ser
660                           665                           670                           675

CAG   TGG   TCT   GAA   TGT   AAC   AAG   TCC   TGT   GGG   AAA   GGT   CAC   ATG   ATT   CGA    2298
Gln   Trp   Ser   Glu   Cys   Asn   Lys   Ser   Cys   Gly   Lys   Gly   His   Met   Ile   Arg
                        680                           685                           690

ACC   CGG   ACA   ATC   CAA   ATG   GAA   CCT   CAG   TTT   GGA   GGT   GCA   CCC   TGC   CCA    2346
Thr   Arg   Thr   Ile   Gln   Met   Glu   Pro   Gln   Phe   Gly   Gly   Ala   Pro   Cys   Pro
```

|  |  |  |  |  |  |  |  |  |  |  |  |  |  |  |  |  |
|---|---|---|---|---|---|---|---|---|---|---|---|---|---|---|---|---|
|  |  | 695 |  |  |  | 700 |  |  |  |  | 705 |  |  |  |  |  |
| GAG | ACT | GTG | CAA | CGC | AAG | AAG | TGC | CGT | GCC | CGG | AAA | TGC | CTT | CGC | AGC | 2394 |
| Glu | Thr | Val | Gln | Arg | Lys | Lys | Cys | Arg | Ala | Arg | Lys | Cys | Leu | Arg | Ser |  |
|  |  | 710 |  |  |  | 715 |  |  |  |  | 720 |  |  |  |  |  |
| CCA | TCG | ATC | CAG | AAG | CTG | CGC | TGG | AGG | GAG | GCC | CGA | GAG | AGC | AGG | AGG | 2442 |
| Pro | Ser | Ile | Gln | Lys | Leu | Arg | Trp | Arg | Glu | Ala | Arg | Glu | Ser | Arg | Arg |  |
|  |  | 725 |  |  |  | 730 |  |  |  |  | 735 |  |  |  |  |  |
| AGT | GAG | CAG | CTG | AGG | GAA | GAG | TCA | GAT | GGA | GAG | CAG | TTC | CCA | GGC | TGT | 2490 |
| Ser | Glu | Gln | Leu | Arg | Glu | Glu | Ser | Asp | Gly | Glu | Gln | Phe | Pro | Gly | Cys |  |
| 740 |  |  |  |  | 745 |  |  |  |  | 750 |  |  |  |  | 755 |  |
| CGG | ATG | CGC | CCG | TGG | ACA | GCC | TGG | TCA | GAG | TGC | ACC | AAA | CTG | TGC | GGA | 2538 |
| Arg | Met | Arg | Pro | Trp | Thr | Ala | Trp | Ser | Glu | Cys | Thr | Lys | Leu | Cys | Gly |  |
|  |  |  |  | 760 |  |  |  |  | 765 |  |  |  |  | 770 |  |  |
| GGT | GGG | ATC | CAA | GAA | CGC | TAC | ATG | ACT | GTG | AAG | AAG | AGG | TTC | AAA | AGC | 2586 |
| Gly | Gly | Ile | Gln | Glu | Arg | Tyr | Met | Thr | Val | Lys | Lys | Arg | Phe | Lys | Ser |  |
|  |  |  | 775 |  |  |  |  | 780 |  |  |  |  | 785 |  |  |  |
| TCC | CAG | TTT | ACC | AGC | TGC | AAA | GAC | AAG | AAG | GAG | ATC | AGA | GCG | TGC | AAC | 2634 |
| Ser | Gln | Phe | Thr | Ser | Cys | Lys | Asp | Lys | Lys | Glu | Ile | Arg | Ala | Cys | Asn |  |
|  |  | 790 |  |  |  |  | 795 |  |  |  |  | 800 |  |  |  |  |
| GTG | CAC | CCT | TGT | T AGTAGGGGTT | | CAACTCCCCA | | GGGCTGCATT | | CCAGATTCTA | | | | | | 2687 |
| Val | His | Pro | Cys |  |  |  |  |  |  |  |  |  |  |  |  |  |
|  |  | 805 |  |  |  |  |  |  |  |  |  |  |  |  |  |  |

```
GTCACCAATG  GTTGGGTGGT  GTATTTGCTT  GTTAAGATG   ATTTAAATTG  TGTCCACATG  2747
TTTTCATTTT  TACCGGTGTG  GTTTGCCCAA  TAGTCTTATG  GAGGCCGAGG  GACATCTTGT  2807
CTGAATACTT  CTTGGTGAGT  ACAGGCCAAG  CGGGGCATCT  TGTCCCCAGG  CGCCATCTTC  2867
CTGCACTGAG  TTGAGTAGTG  TTGGTTCACC  TTGGTACTAA  ACTGAATCGT  GTCCCTCTGG  2927
AGCATCCCCT  GGTCAAGCAG  GGTGGAGACT  TTGGCCATCC  ACAAGGAGAA  GCAACCAGGA  2987
TGCAGCATGC  GGGAGACACA  GCCATTAATT  GCAAGGACA   GATCCTCCTC  TCTCACCTTT  3047
GGCCTGCTCA  CTCTTACAGA  AACCTGTTTG  TCCGCCTCCT  TTTTATTTA   GCACAACTCC  3107
AGGCATCTTG  GTAAGTCTCC  AGGGTCATGG  GTTCTTCGGT  GCCCTGAAGG  AGAAGCCCTG  3167
AGGTGAGGTG  GCATTTGTTA  CAAACCTCCC  AATACTGCTT  TACTGGCATC  ACAAGGTCAG  3227
CAGGTGATGA  TGGCTACTTC  ATTTCATTGT  GAGCCGTGAT  TTCCGTTGAG  TTTTGATTGT  3287
TGGTGCCATA  AATGTCCTAG  GATGCTGGAC  GGACACATCA  GCCTTGTCAG  CAGATCCTTC  3347
TTTGAGCCAA  TGTAGACAGT  AAGCTGGGCA  CTGGTTCCAA  AGCCAACTTA  AAATCTTCCT  3407
ACACATATCC  AGACCTTTTT  TTAGGTTGCC  CAAACTTCCT  TAGAATAAAG  CATTTTAGCT  3467
CTGAGAACTA  CTTGATAAGT  CTGCCAGGAA  GCCCCCAAGT  CAATTCTTCA  ACAAAAATAC  3527
TATCTTCCCT  ACTTAATTTT  TTTTAAGTCA  TGATATTTTA  TAGTTAGAGG  AGAGAGAGAC  3587
AATCTATTCC  CATGACTAAG  ACACAAACCT  ACAAGAAAGG  GTTACTCAGT  CAAGCCTGTG  3647
CCTGACTTCT  GGACCAGGCC  CCTGATTTTC  ATGGATAGTC  CAAAGGAAGG  CCAGGGGTTC  3707
CCACTGACTC  CAAGCCATCA  GCAGCACCCA  AACCCAGGAG  CAACAAATAT  TCAGAGAAAG  3767
AGGATGTTTA  TCTCAGCTAT  GAGCTCATTG  GCAGGTTGTA  CTCATGCATC  TGTTAAAAGC  3827
ACCACCACAT  CCTTTTGCAA  GTCTGTTTAT  TACCGCTTCA  TCCAAATACA  TTTTGTGGTC  3887
AAGATCGACA  CAGTGCTATG  AATACAGTAC  TTTAAGGTCT  GCATTAAACA  CATCAGAATA  3947
TTTCCTGCCA  CATCTATGTA  CAACCCCTGA  ATATGTATTT  TTCCTTAACA  CAAGAGAGCC  4007
TGTTCAATTA  AAAAAAAAA   AA                                              4029
```

( 2 ) INFORMATION FOR SEQ ID NO:10:

( i ) SEQUENCE CHARACTERISTICS:

( A ) LENGTH: 807 amino acids
( B ) TYPE: amino acid
( D ) TOPOLOGY: linear ( i i ) MOLECULE TYPE: protein ( x i ) SEQUENCE DESCRIPTION: SEQ ID NO:10:

| Met | Arg | Leu | Ser | Pro | Ala | Pro | Leu | Arg | Leu | Ser | Arg | Gly | Pro | Ala | Leu |
|---|---|---|---|---|---|---|---|---|---|---|---|---|---|---|---|
| 1 | | | | 5 | | | | | 10 | | | | | 15 | |
| Leu | Ala | Leu | Ala | Leu | Pro | Leu | Ala | Ala | Ala | Leu | Ala | Phe | Ser | Asp | Glu |
| | | | 20 | | | | | 25 | | | | | 30 | | |
| Thr | Leu | Asp | Lys | Val | Ala | Lys | Ser | Glu | Gly | Tyr | Cys | Ser | Arg | Ile | Leu |
| | | 35 | | | | | 40 | | | | | 45 | | | |
| Arg | Ala | Gln | Gly | Thr | Arg | Arg | Glu | Gly | Tyr | Thr | Glu | Phe | Ser | Leu | Arg |
| | 50 | | | | | 55 | | | | | 60 | | | | |
| Val | Glu | Gly | Asp | Pro | Asp | Phe | Tyr | Lys | Pro | Gly | Ser | Ser | Tyr | Arg | Val |
| 65 | | | | | 70 | | | | | 75 | | | | | 80 |
| Thr | Leu | Ser | Ala | Ala | Pro | Pro | Ser | Tyr | Phe | Arg | Gly | Phe | Thr | Leu | Ile |
| | | | | 85 | | | | | 90 | | | | | 95 | |
| Ala | Leu | Lys | Glu | Asn | Arg | Glu | Gly | Asp | Lys | Glu | Glu | Asp | His | Ala | Gly |
| | | | 100 | | | | | 105 | | | | | 110 | | |
| Thr | Phe | Gln | Ile | Ile | Asp | Glu | Glu | Thr | Gln | Phe | Met | Ser | Asn | Cys |
| | | 115 | | | | | 120 | | | | | 125 | | | |
| Pro | Val | Ala | Val | Thr | Glu | Ser | Thr | Pro | Arg | Arg | Arg | Thr | Arg | Ile | Gln |
| 130 | | | | | 135 | | | | | 140 | | | | | |
| Val | Phe | Trp | Ile | Ala | Pro | Pro | Thr | Gly | Thr | Gly | Cys | Val | Ile | Leu | Lys |
| 145 | | | | | 150 | | | | | 155 | | | | | 160 |
| Ala | Ser | Ile | Val | Gln | Lys | Arg | Ile | Ile | Tyr | Phe | Gln | Asp | Glu | Gly | Ser |
| | | | | 165 | | | | | 170 | | | | | 175 | |
| Leu | Thr | Lys | Lys | Leu | Cys | Glu | Gln | Asp | Pro | Thr | Leu | Asp | Gly | Val | Thr |
| | | | 180 | | | | | 185 | | | | | 190 | | |
| Asp | Arg | Pro | Ile | Leu | Asp | Cys | Cys | Ala | Cys | Gly | Thr | Ala | Lys | Tyr | Arg |
| | | 195 | | | | | 200 | | | | | 205 | | | |
| Leu | Thr | Phe | Tyr | Gly | Asn | Trp | Ser | Glu | Lys | Thr | His | Pro | Lys | Asp | Tyr |
| | 210 | | | | | 215 | | | | | 220 | | | | |
| Pro | Arg | Arg | Ala | Asn | His | Trp | Ser | Ala | Ile | Ile | Gly | Gly | Ser | His | Ser |
| 225 | | | | | 230 | | | | | 235 | | | | | 240 |
| Lys | Asn | Tyr | Val | Leu | Trp | Glu | Tyr | Gly | Gly | Tyr | Ala | Ser | Glu | Gly | Val |
| | | | | 245 | | | | | 250 | | | | | 255 | |
| Lys | Gln | Val | Ala | Glu | Leu | Gly | Ser | Pro | Val | Lys | Met | Glu | Glu | Glu | Ile |
| | | | 260 | | | | | 265 | | | | | 270 | | |
| Arg | Gln | Gln | Ser | Asp | Glu | Val | Leu | Thr | Val | Ile | Lys | Ala | Lys | Ala | Gln |
| | | 275 | | | | | 280 | | | | | 285 | | | |
| Trp | Pro | Ser | Trp | Gln | Pro | Val | Asn | Val | Arg | Ala | Ala | Pro | Ser | Ala | Glu |
| | 290 | | | | | 295 | | | | | 300 | | | | |
| Phe | Ser | Val | Asp | Arg | Thr | Arg | His | Leu | Met | Ser | Phe | Leu | Thr | Met | Met |
| 305 | | | | | 310 | | | | | 315 | | | | | 320 |
| Gly | Pro | Ser | Pro | Asp | Trp | Asn | Val | Gly | Leu | Ser | Ala | Glu | Asp | Leu | Cys |
| | | | | 325 | | | | | 330 | | | | | 335 | |
| Thr | Lys | Glu | Cys | Gly | Trp | Val | Gln | Lys | Val | Val | Gln | Asp | Leu | Ile | Pro |
| | | | 340 | | | | | 345 | | | | | 350 | | |
| Trp | Asp | Ala | Gly | Thr | Asp | Ser | Gly | Val | Thr | Tyr | Glu | Ser | Pro | Asn | Lys |
| | | 355 | | | | | 360 | | | | | 365 | | | |
| Pro | Thr | Ile | Pro | Gln | Glu | Lys | Ile | Arg | Pro | Leu | Thr | Ser | Leu | Asp | His |
| | 370 | | | | | 375 | | | | | 380 | | | | |

```
Pro  Gln  Ser  Pro  Phe  Tyr  Asp  Pro  Glu  Gly  Gly  Ser  Ile  Thr  Gln  Val
385                      390                      395                      400

Ala  Arg  Val  Val  Ile  Glu  Arg  Ile  Ala  Arg  Lys  Gly  Glu  Gln  Cys  Asn
                    405                      410                      415

Ile  Val  Pro  Asp  Asn  Val  Asp  Asp  Ile  Val  Ala  Asp  Leu  Ala  Pro  Glu
               420                      425                      430

Glu  Lys  Asp  Glu  Asp  Asp  Thr  Pro  Glu  Thr  Cys  Ile  Tyr  Ser  Asn  Trp
          435                      440                      445

Ser  Pro  Trp  Ser  Ala  Cys  Ser  Ser  Thr  Cys  Glu  Lys  Gly  Lys  Arg
     450                      455                      460

Met  Arg  Gln  Arg  Met  Leu  Lys  Ala  Gln  Leu  Asp  Leu  Ser  Val  Pro  Cys
465                      470                      475                      480

Pro  Asp  Thr  Gln  Asp  Phe  Gln  Pro  Cys  Met  Gly  Pro  Gly  Cys  Ser  Asp
               485                      490                      495

Glu  Asp  Gly  Ser  Thr  Cys  Thr  Met  Ser  Glu  Trp  Ile  Thr  Trp  Ser  Pro
               500                      505                      510

Cys  Ser  Val  Ser  Cys  Gly  Met  Gly  Met  Arg  Ser  Arg  Glu  Arg  Tyr  Val
          515                      520                      525

Lys  Gln  Phe  Pro  Glu  Asp  Gly  Ser  Val  Cys  Met  Leu  Pro  Thr  Glu  Glu
     530                      535                      540

Thr  Glu  Lys  Cys  Thr  Val  Asn  Glu  Glu  Cys  Ser  Pro  Ser  Cys  Leu
545                      550                      555                      560

Val  Thr  Glu  Trp  Gly  Glu  Trp  Asp  Asp  Cys  Ser  Ala  Thr  Cys  Gly  Met
               565                      570                      575

Gly  Met  Lys  Lys  Arg  His  Arg  Met  Val  Lys  Met  Ser  Pro  Ala  Asp  Gly
               580                      585                      590

Ser  Met  Cys  Lys  Ala  Glu  Thr  Ser  Gln  Ala  Glu  Lys  Cys  Met  Met  Pro
          595                      600                      605

Glu  Cys  His  Thr  Ile  Pro  Cys  Leu  Leu  Ser  Pro  Trp  Ser  Glu  Trp  Ser
     610                      615                      620

Asp  Cys  Ser  Val  Thr  Cys  Gly  Lys  Gly  Met  Arg  Thr  Arg  Gln  Arg  Met
625                      630                      635                      640

Leu  Lys  Ser  Leu  Ala  Glu  Leu  Gly  Asp  Cys  Asn  Glu  Asp  Leu  Glu  Gln
                    645                      650                      655

Ala  Glu  Lys  Cys  Met  Leu  Pro  Glu  Cys  Pro  Ile  Asp  Cys  Glu  Leu  Ser
               660                      665                      670

Glu  Trp  Ser  Gln  Trp  Ser  Glu  Cys  Asn  Lys  Ser  Cys  Gly  Lys  Gly  His
          675                      680                      685

Met  Ile  Arg  Thr  Arg  Thr  Ile  Gln  Met  Glu  Pro  Gln  Phe  Gly  Gly  Ala
690                      695                      700

Pro  Cys  Pro  Glu  Thr  Val  Gln  Arg  Lys  Lys  Cys  Arg  Ala  Arg  Lys  Cys
705                      710                      715                      720

Leu  Arg  Ser  Pro  Ser  Ile  Gln  Lys  Leu  Arg  Trp  Arg  Glu  Ala  Arg  Glu
               725                      730                      735

Ser  Arg  Arg  Ser  Glu  Gln  Leu  Arg  Glu  Glu  Ser  Asp  Gly  Glu  Gln  Phe
               740                      745                      750

Pro  Gly  Cys  Arg  Met  Arg  Pro  Trp  Thr  Ala  Trp  Ser  Glu  Cys  Thr  Lys
          755                      760                      765

Leu  Cys  Gly  Gly  Gly  Ile  Gln  Glu  Arg  Tyr  Met  Thr  Val  Lys  Lys  Arg
     770                      775                      780

Phe  Lys  Ser  Ser  Gln  Phe  Thr  Ser  Cys  Lys  Asp  Lys  Lys  Glu  Ile  Arg
785                      790                      795                      800

Ala  Cys  Asn  Val  His  Pro  Cys
                    805
```

( 2 ) INFORMATION FOR SEQ ID NO:11:

( i ) SEQUENCE CHARACTERISTICS:
    ( A ) LENGTH: 3226 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 136..2543

( x i ) SEQUENCE DESCRIPTION: SEQ ID NO:11:

```
GTGTCCCTCC CTCCTCCCTC CCTCCCTCTC TCCCTCCCTC CCCGCCTGCC CCCTCCCCGC    60

CTCTCCCCTC CCCTCTCCCG CGCCGCAGCC TCCCCCGGGC CGCCCGGCGC TGCCCGAGCT   120

GTGCGGGCGC CGAGG ATG GCA GCG CGG CTG CGG CCC CTG GCC CTG CGG CTG   171
              Met Ala Ala Arg Leu Arg Pro Leu Ala Leu Arg Leu
                1               5                  10

CTG GCG CGC ACC TTC CCC TTG GTG GCG AGG GGC TTC TCC GAC GAG ACC   219
Leu Ala Arg Thr Phe Pro Leu Val Ala Arg Gly Phe Ser Asp Glu Thr
         15                  20                  25

CTG GAG AAA GCC GCC AAA TCC GAG GGC TAC TGC AGC CGG ATC CTG CGA   267
Leu Glu Lys Ala Ala Lys Ser Glu Gly Tyr Cys Ser Arg Ile Leu Arg
     30                  35                  40

GCC CAA GGC ACC AGG AGG GAA GGG TAC AAT GAA TTT AGC CTG AGG GTG   315
Ala Gln Gly Thr Arg Arg Glu Gly Tyr Asn Glu Phe Ser Leu Arg Val
 45                  50                  55                  60

GAG GGC GAT CCG GAA TTC TAC AAG CCT GGG AAC AGT TAC CGC GTG ACG   363
Glu Gly Asp Pro Glu Phe Tyr Lys Pro Gly Asn Ser Tyr Arg Val Thr
                 65                  70                  75

CTT TCT GCT GCC ACT CCT GCG TAC TTT CGA GGA TTC ACA TTG ATT GCT   411
Leu Ser Ala Ala Thr Pro Ala Tyr Phe Arg Gly Phe Thr Leu Ile Ala
             80                  85                  90

CTG AAG GAA GGA AAA GAA GGT GAT AAA GAG GAA GAC CAT GCG GGA ACT   459
Leu Lys Glu Gly Lys Glu Gly Asp Lys Glu Glu Asp His Ala Gly Thr
         95                 100                 105

TTT CAG ATC ATA GAT GAA GAA GAG ACG CAG TTC ATG AGC AAT TGT CCC   507
Phe Gln Ile Ile Asp Glu Glu Glu Thr Gln Phe Met Ser Asn Cys Pro
    110                 115                 120

GTC GCG GTT ACT GAG AGC ACA CCT AGA AGG AGG ACA CGC ATC CAG GTC   555
Val Ala Val Thr Glu Ser Thr Pro Arg Arg Arg Thr Arg Ile Gln Val
125                 130                 135                 140

TTC TGG ACA GCT CCT CCT ACT GGT ACG GGC TGT GTC ATT CTG AAA GCC   603
Phe Trp Thr Ala Pro Pro Thr Gly Thr Gly Cys Val Ile Leu Lys Ala
                145                 150                 155

AGT ATT GTG CAG AAG CGC ATT ATT TAT TTT CAG GAC GAG GGT TCT CTC   651
Ser Ile Val Gln Lys Arg Ile Ile Tyr Phe Gln Asp Glu Gly Ser Leu
            160                 165                 170

ACC AAA AGA ATC TGT GAA CAA GAT TCA GCC TCT GAA GGT GTG ACT GAC   699
Thr Lys Arg Ile Cys Glu Gln Asp Ser Ala Ser Glu Gly Val Thr Asp
        175                 180                 185

AAA CCA ACA TTA GAT TGC TGT GCC TGT GGA ACT GCC AAA TAC AGG CTA   747
Lys Pro Thr Leu Asp Cys Cys Ala Cys Gly Thr Ala Lys Tyr Arg Leu
    190                 195                 200

ACG TTT TAT GGA AAT TGG TCG GAA AAA ACA CAT CCC AAA GAC TTT CCT   795
Thr Phe Tyr Gly Asn Trp Ser Glu Lys Thr His Pro Lys Asp Phe Pro
205                 210                 215                 220

CGG CGC ACC AAC CAT TGG TCT GCG ATC ATT GGT AGC TCT CAC TCA AAG   843
Arg Arg Thr Asn His Trp Ser Ala Ile Ile Gly Ser Ser His Ser Lys
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     |     | 225 |     |     |     |     | 230 |     |     |     |     | 235 |      |
| AAC | TAC | ATC | CTT | TGG | GAG | TAT | GGA | GGG | TAT | GCT | AGT | GAA | GGT | GTC | AAG | 891  |
| Asn | Tyr | Ile | Leu | Trp | Glu | Tyr | Gly | Gly | Tyr | Ala | Ser | Glu | Gly | Val | Lys |      |
|     |     |     | 240 |     |     |     |     | 245 |     |     |     |     | 250 |     |     |      |
| CAG | GTT | GCA | GAG | CTG | GGA | TCC | CCA | GTC | AAG | ATG | GAA | GAA | GAA | ATT | CGA | 939  |
| Gln | Val | Ala | Glu | Leu | Gly | Ser | Pro | Val | Lys | Met | Glu | Glu | Glu | Ile | Arg |      |
|     |     | 255 |     |     |     |     | 260 |     |     |     |     | 265 |     |     |     |      |
| CAA | CAA | AGT | GAT | GAG | GTT | TTA | ACA | GTC | ATC | AAG | GCA | AAA | GCA | CAG | TGG | 987  |
| Gln | Gln | Ser | Asp | Glu | Val | Leu | Thr | Val | Ile | Lys | Ala | Lys | Ala | Gln | Trp |      |
| 270 |     |     |     |     | 275 |     |     |     |     | 280 |     |     |     |     |     |      |
| CCT | GCC | TGG | CAG | CCT | CTG | AAT | GTG | AGA | GCT | GCT | CCC | TCT | GCT | GAG | TTT | 1035 |
| Pro | Ala | Trp | Gln | Pro | Leu | Asn | Val | Arg | Ala | Ala | Pro | Ser | Ala | Glu | Phe |      |
| 285 |     |     |     |     | 290 |     |     |     |     | 295 |     |     |     |     | 300 |      |
| TCT | GTT | GAT | CGC | CAC | CGG | CAC | CTG | ATG | TCC | TTC | CTC | ACC | ATG | CTG | GGG | 1083 |
| Ser | Val | Asp | Arg | His | Arg | His | Leu | Met | Ser | Phe | Leu | Thr | Met | Leu | Gly |      |
|     |     |     |     | 305 |     |     |     |     | 310 |     |     |     |     | 315 |     |      |
| CCC | AGT | CCC | GAC | TGG | AAT | GTG | GGC | CTG | TCT | GCT | GAG | GAC | CTC | TGC | ACC | 1131 |
| Pro | Ser | Pro | Asp | Trp | Asn | Val | Gly | Leu | Ser | Ala | Glu | Asp | Leu | Cys | Thr |      |
|     |     |     | 320 |     |     |     |     | 325 |     |     |     |     | 330 |     |     |      |
| AAG | GAC | TGT | GGC | TGG | GTT | CAG | AAA | GTC | GTG | CAG | GAT | TTA | ATC | CCC | TGG | 1179 |
| Lys | Asp | Cys | Gly | Trp | Val | Gln | Lys | Val | Val | Gln | Asp | Leu | Ile | Pro | Trp |      |
|     |     | 335 |     |     |     |     | 340 |     |     |     |     | 345 |     |     |     |      |
| GAT | GCC | GGC | ACA | GAC | AGT | GGC | GTC | ACC | TAT | GAG | TCA | CCC | AAC | AAA | CCT | 1227 |
| Asp | Ala | Gly | Thr | Asp | Ser | Gly | Val | Thr | Tyr | Glu | Ser | Pro | Asn | Lys | Pro |      |
| 350 |     |     |     |     | 355 |     |     |     |     | 360 |     |     |     |     |     |      |
| ACA | GTT | CCT | CAA | GAG | AAG | ATT | AGA | CCA | CTT | ACA | AGC | TTA | GAT | CAC | CCT | 1275 |
| Thr | Val | Pro | Gln | Glu | Lys | Ile | Arg | Pro | Leu | Thr | Ser | Leu | Asp | His | Pro |      |
| 365 |     |     |     |     | 370 |     |     |     |     | 375 |     |     |     |     | 380 |      |
| CAG | AGT | CCA | TTT | TAT | GAT | CCA | GAA | GGA | GGA | TCT | ATC | AAG | CTT | GTA | GCC | 1323 |
| Gln | Ser | Pro | Phe | Tyr | Asp | Pro | Glu | Gly | Gly | Ser | Ile | Lys | Leu | Val | Ala |      |
|     |     |     |     | 385 |     |     |     |     | 390 |     |     |     |     | 395 |     |      |
| AGA | GTC | GTG | CTT | GAA | AGA | ATT | GCA | CGC | AAG | GGG | GAG | CAG | TGC | AAC | TTC | 1371 |
| Arg | Val | Val | Leu | Glu | Arg | Ile | Ala | Arg | Lys | Gly | Glu | Gln | Cys | Asn | Phe |      |
|     |     |     | 400 |     |     |     |     | 405 |     |     |     |     | 410 |     |     |      |
| GTA | CCT | GAT | AAC | ATA | GAT | GAT | ATT | GTG | GCA | GAC | CTA | GCA | CCA | GAA | GAA | 1419 |
| Val | Pro | Asp | Asn | Ile | Asp | Asp | Ile | Val | Ala | Asp | Leu | Ala | Pro | Glu | Glu |      |
|     |     |     | 415 |     |     |     |     | 420 |     |     |     |     | 425 |     |     |      |
| AAA | GAA | GAA | GAT | GAT | ACC | CCT | GAG | ACC | TGC | ATA | TAT | TCA | AAC | TGG | TCC | 1467 |
| Lys | Glu | Glu | Asp | Asp | Thr | Pro | Glu | Thr | Cys | Ile | Tyr | Ser | Asn | Trp | Ser |      |
|     | 430 |     |     |     |     | 435 |     |     |     |     | 440 |     |     |     |     |      |
| CCC | TGG | TCA | GCC | TGC | AGC | TCC | TCT | ACC | TGT | GAG | AAG | GGC | AAG | AGG | ATG | 1515 |
| Pro | Trp | Ser | Ala | Cys | Ser | Ser | Ser | Thr | Cys | Glu | Lys | Gly | Lys | Arg | Met |      |
| 445 |     |     |     |     | 450 |     |     |     |     | 455 |     |     |     |     | 460 |      |
| AGG | CAG | AGA | ATG | CTT | AAA | GCT | CAG | CTG | GAC | CTC | AGT | GTG | CCC | TGT | CCT | 1563 |
| Arg | Gln | Arg | Met | Leu | Lys | Ala | Gln | Leu | Asp | Leu | Ser | Val | Pro | Cys | Pro |      |
|     |     |     |     | 465 |     |     |     |     | 470 |     |     |     |     | 475 |     |      |
| GAT | ACC | CAA | GAT | TTT | CAG | CCA | TGC | ATG | GGT | CCA | GGC | TGC | AGT | GAT | GAA | 1611 |
| Asp | Thr | Gln | Asp | Phe | Gln | Pro | Cys | Met | Gly | Pro | Gly | Cys | Ser | Asp | Glu |      |
|     |     | 480 |     |     |     |     | 485 |     |     |     |     | 490 |     |     |     |      |
| GAT | GGT | TCA | ACT | TGC | ATG | ATG | TCT | GAC | TGG | ATT | ACA | TGG | TCC | CCC | TGT | 1659 |
| Asp | Gly | Ser | Thr | Cys | Met | Met | Ser | Asp | Trp | Ile | Thr | Trp | Ser | Pro | Cys |      |
|     |     | 495 |     |     |     |     | 500 |     |     |     |     | 505 |     |     |     |      |
| AGT | GTT | TCC | TGT | GGA | ATG | GGA | ACG | CGA | TCT | AGA | GAG | AGA | TAT | GTA | AAG | 1707 |
| Ser | Val | Ser | Cys | Gly | Met | Gly | Thr | Arg | Ser | Arg | Glu | Arg | Tyr | Val | Lys |      |
|     |     | 510 |     |     |     |     | 515 |     |     |     |     | 520 |     |     |     |      |
| CAA | TTC | CCC | GAA | GAT | GGC | TCT | ATG | TGC | AAA | GTG | CCT | ACT | GAA | GAA | ACT | 1755 |
| Gln | Phe | Pro | Glu | Asp | Gly | Ser | Met | Cys | Lys | Val | Pro | Thr | Glu | Glu | Thr |      |
| 525 |     |     |     |     | 530 |     |     |     |     | 535 |     |     |     |     | 540 |      |
| GAG | AAA | TGT | ATT | GTA | AAT | GAG | GAA | TGC | TCC | CCT | AGC | AGC | TGC | CTT | GTC | 1803 |
| Glu | Lys | Cys | Ile | Val | Asn | Glu | Glu | Cys | Ser | Pro | Ser | Ser | Cys | Leu | Val |      |

|  |  |  |  |  |  |  |  |  |  |  |  |  |  |  |  |
|---|---|---|---|---|---|---|---|---|---|---|---|---|---|---|---|
|  |  |  | 545 |  |  |  | 550 |  |  |  |  | 555 |  |  |  |
| ACC | GAA | TGG | GGA | GAG | TGG | GAT | GAA | TGC | AGT | GCT | AGC | TGT | GGC | ACA | GGA |
| Thr | Glu | Trp | Gly | Glu | Trp | Asp | Glu | Cys | Ser | Ala | Ser | Cys | Gly | Thr | Gly |
|  |  |  | 560 |  |  |  | 565 |  |  |  |  | 570 |  |  |  |

1851

| ATG | AAA | AGG | CGA | CAC | AGA | ATG | ATC | AAG | ATG | ACT | CCT | GCT | GAT | GGA | TCT |
|---|---|---|---|---|---|---|---|---|---|---|---|---|---|---|---|
| Met | Lys | Arg | Arg | His | Arg | Met | Ile | Lys | Met | Thr | Pro | Ala | Asp | Gly | Ser |
|  |  | 575 |  |  |  | 580 |  |  |  |  | 585 |  |  |  |  |

1899

| ATG | TGC | AAG | GCA | GAA | ACT | ACA | GAG | GCA | GAG | AAA | TGC | ATG | ATG | CCC | GAA |
|---|---|---|---|---|---|---|---|---|---|---|---|---|---|---|---|
| Met | Cys | Lys | Ala | Glu | Thr | Thr | Glu | Ala | Glu | Lys | Cys | Met | Met | Pro | Glu |
|  |  | 590 |  |  |  | 595 |  |  |  |  | 600 |  |  |  |  |

1947

| TGC | CAT | ACT | ATT | CCC | TGC | CTT | CTA | TCC | CCA | TGG | TCT | GAA | TGG | AGC | GAC |
|---|---|---|---|---|---|---|---|---|---|---|---|---|---|---|---|
| Cys | His | Thr | Ile | Pro | Cys | Leu | Leu | Ser | Pro | Trp | Ser | Glu | Trp | Ser | Asp |
| 605 |  |  |  | 610 |  |  |  | 615 |  |  |  |  | 620 |  |  |

1995

| TGC | AGC | GTG | ACA | TGT | GGG | AAG | GGA | ATG | CGA | ACC | CGG | CAA | AGG | ATG | CTG |
|---|---|---|---|---|---|---|---|---|---|---|---|---|---|---|---|
| Cys | Ser | Val | Thr | Cys | Gly | Lys | Gly | Met | Arg | Thr | Arg | Gln | Arg | Met | Leu |
|  |  |  |  | 625 |  |  |  | 630 |  |  |  |  | 635 |  |  |

2043

| AAA | TCT | GCA | GCT | GAG | CTT | GGA | GAC | TGC | AAT | GAG | GAA | CTG | GAG | CAA | GCA |
|---|---|---|---|---|---|---|---|---|---|---|---|---|---|---|---|
| Lys | Ser | Ala | Ala | Glu | Leu | Gly | Asp | Cys | Asn | Glu | Glu | Leu | Glu | Gln | Ala |
|  |  |  | 640 |  |  |  | 645 |  |  |  |  | 650 |  |  |  |

2091

| GAG | AAA | TGC | ATG | CTA | CCT | GAA | TGC | CCC | ATT | GAC | TGT | GAG | CTA | ACG | GAG |
|---|---|---|---|---|---|---|---|---|---|---|---|---|---|---|---|
| Glu | Lys | Cys | Met | Leu | Pro | Glu | Cys | Pro | Ile | Asp | Cys | Glu | Leu | Thr | Glu |
|  |  | 655 |  |  |  | 660 |  |  |  |  | 665 |  |  |  |  |

2139

| TGG | TCC | CAG | TGG | TCC | GAG | TGC | AAT | ACC | TCC | TGT | GGG | AAG | GGC | CAC | ATG |
|---|---|---|---|---|---|---|---|---|---|---|---|---|---|---|---|
| Trp | Ser | Gln | Trp | Ser | Glu | Cys | Asn | Thr | Ser | Cys | Gly | Lys | Gly | His | Met |
| 670 |  |  |  | 675 |  |  |  |  | 680 |  |  |  |  |  |  |

2187

| ATC | AGA | ACA | AGA | ATG | ATC | AAA | ATA | GAA | CCA | CAG | TTT | GGA | GGA | ACA | GCA |
|---|---|---|---|---|---|---|---|---|---|---|---|---|---|---|---|
| Ile | Arg | Thr | Arg | Met | Ile | Lys | Ile | Glu | Pro | Gln | Phe | Gly | Gly | Thr | Ala |
| 685 |  |  |  | 690 |  |  |  | 695 |  |  |  |  | 700 |  |  |

2235

| TGC | CCA | GAA | ACT | GTC | CAA | CGT | ACT | AAA | TGT | CGA | GTA | AGG | AAA | TGC | CTG |
|---|---|---|---|---|---|---|---|---|---|---|---|---|---|---|---|
| Cys | Pro | Glu | Thr | Val | Gln | Arg | Thr | Lys | Cys | Arg | Val | Arg | Lys | Cys | Leu |
|  |  |  | 705 |  |  |  | 710 |  |  |  |  | 715 |  |  |  |

2283

| AGA | GGC | CCA | GGT | ATG | GAA | AAG | AGG | CGT | TGG | AAG | GAG | GCC | CGG | GAG | AAA |
|---|---|---|---|---|---|---|---|---|---|---|---|---|---|---|---|
| Arg | Gly | Pro | Gly | Met | Glu | Lys | Arg | Arg | Trp | Lys | Glu | Ala | Arg | Glu | Lys |
|  |  |  | 720 |  |  |  | 725 |  |  |  |  | 730 |  |  |  |

2331

| AGA | AGA | AGT | GAA | CAA | GCA | AAA | AAA | AAT | ATT | GAT | AAT | GAG | CAA | TAT | CCA |
|---|---|---|---|---|---|---|---|---|---|---|---|---|---|---|---|
| Arg | Arg | Ser | Glu | Gln | Ala | Lys | Lys | Asn | Ile | Asp | Asn | Glu | Gln | Tyr | Pro |
|  |  | 735 |  |  |  | 740 |  |  |  |  | 745 |  |  |  |  |

2379

| GTT | TGT | AGG | CTG | AAA | CCA | TGG | ACT | GCT | TGG | ACA | GAA | TGT | TCT | ACA | CTC |
|---|---|---|---|---|---|---|---|---|---|---|---|---|---|---|---|
| Val | Cys | Arg | Leu | Lys | Pro | Trp | Thr | Ala | Trp | Thr | Glu | Cys | Ser | Thr | Leu |
|  | 750 |  |  |  | 755 |  |  |  |  | 760 |  |  |  |  |  |

2427

| TGT | GGA | GGT | GGA | ATT | CAG | GAG | CGC | TAC | ATG | ATG | GTA | AAG | AAG | AGG | TCC |
|---|---|---|---|---|---|---|---|---|---|---|---|---|---|---|---|
| Cys | Gly | Gly | Gly | Ile | Gln | Glu | Arg | Tyr | Met | Met | Val | Lys | Lys | Arg | Ser |
| 765 |  |  |  | 770 |  |  |  |  | 775 |  |  |  |  | 780 |  |

2475

| AAA | AGC | ACT | CAG | TTT | ACT | AGC | TGC | AAA | GAC | AAA | AAG | GAG | CTA | AGA | GCA |
|---|---|---|---|---|---|---|---|---|---|---|---|---|---|---|---|
| Lys | Ser | Thr | Gln | Phe | Thr | Ser | Cys | Lys | Asp | Lys | Lys | Glu | Leu | Arg | Ala |
|  |  |  |  | 785 |  |  |  |  | 790 |  |  |  |  | 795 |  |

2523

| TGT | AAC | GTT | CAT | CCT | TGT | TA | GGAAACACA | AGGCTTCCAA | GTGATGCACT |
|---|---|---|---|---|---|---|---|---|---|
| Cys | Asn | Val | His | Pro | Cys |  |  |  |  |
|  |  |  | 800 |  |  |  |  |  |  |

2573

CTGAGCTATA AGGAAAGTCA ACCTTGGTTT GGTTTTTAAA ACAAACAAAA GTATAAAGTG 2633

TATATTAGTT TTCATTTTTG CAGTGTGGTT TGCTTTTAGT CTTGCTGGTG CAAGAAATAT 2693

ATTTTATAAA TATTTCCTCC GATTAATCTA GGTAAACTTT GATGCTCCAG CTAGCCCTTA 2753

CTGCATAAAA ATAGTAGGTC ATTGTGAGTC ATTAACTGA AGTACAGACA TATCTGTGGA 2813

CATGGAATAG CCATATAGAA ATACTACTTG TAAAGACATG GGATGCATGC ATATTAACAT 2873

AACTAATTTG AAGTGACATG TTTCATATGT GGGAGGATTT CTCTCTTGAT TTGATTTAAA 2933

AATCCAAAGC AGTGCCTATG TGATTATACA ACTATGCCAA GGAGAAATTT CAGTAATGCT 2993

-continued

```
GGTTCAATAA TATTAAAGGT GCATGTTTAT CTTTTTACAA TATTGGGTTA AGCGATAGTT  3053
GAAATAATTA CCCTACATAC TTTTGTTCAC ATGGATGCTG CGTTCCATGC AAAATCATCT  3113
TGTTTCTCA  AATAGCAACT TACTTAAATA ATCTGTGCAG CTCAATAGTG ATGTCAGCCC  3173
ATAACACAGT CACAACACAC AAAGACATGT GGCTATCACA GTACCTGTCA CTG          3226
```

( 2 ) INFORMATION FOR SEQ ID NO:12:

( i ) SEQUENCE CHARACTERISTICS:
        ( A ) LENGTH: 802 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Ala Ala Arg Leu Arg Pro Leu Ala Leu Arg Leu Leu Ala Arg Thr
 1               5                  10                  15

Phe Pro Leu Val Ala Arg Gly Phe Ser Asp Glu Thr Leu Glu Lys Ala
            20                  25                  30

Ala Lys Ser Glu Gly Tyr Cys Ser Arg Ile Leu Arg Ala Gln Gly Thr
        35                  40                  45

Arg Arg Glu Gly Tyr Asn Glu Phe Ser Leu Arg Val Glu Gly Asp Pro
    50                  55                  60

Glu Phe Tyr Lys Pro Gly Asn Ser Tyr Arg Val Thr Leu Ser Ala Ala
 65                 70                  75                  80

Thr Pro Ala Tyr Phe Arg Gly Phe Thr Leu Ile Ala Leu Lys Glu Gly
            85                  90                  95

Lys Glu Gly Asp Lys Glu Glu Asp His Ala Gly Thr Phe Gln Ile Ile
       100                 105                 110

Asp Glu Glu Glu Thr Gln Phe Met Ser Asn Cys Pro Val Ala Val Thr
    115                 120                 125

Glu Ser Thr Pro Arg Arg Arg Thr Arg Ile Gln Val Phe Trp Thr Ala
    130                 135                 140

Pro Pro Thr Gly Thr Gly Cys Val Ile Leu Lys Ala Ser Ile Val Gln
145                 150                 155                 160

Lys Arg Ile Ile Tyr Phe Gln Asp Glu Gly Ser Leu Thr Lys Arg Ile
                165                 170                 175

Cys Glu Gln Asp Ser Ala Ser Glu Gly Val Thr Asp Lys Pro Thr Leu
            180                 185                 190

Asp Cys Cys Ala Cys Gly Thr Ala Lys Tyr Arg Leu Thr Phe Tyr Gly
        195                 200                 205

Asn Trp Ser Glu Lys Thr His Pro Lys Asp Phe Pro Arg Arg Thr Asn
    210                 215                 220

His Trp Ser Ala Ile Ile Gly Ser Ser His Ser Lys Asn Tyr Ile Leu
225                 230                 235                 240

Trp Glu Tyr Gly Gly Tyr Ala Ser Glu Gly Val Lys Gln Val Ala Glu
                245                 250                 255

Leu Gly Ser Pro Val Lys Met Glu Glu Ile Arg Gln Gln Ser Asp
            260                 265                 270

Glu Val Leu Thr Val Ile Lys Ala Lys Ala Gln Trp Pro Ala Trp Gln
        275                 280                 285

Pro Leu Asn Val Arg Ala Ala Pro Ser Ala Glu Phe Ser Val Asp Arg
    290                 295                 300

His Arg His Leu Met Ser Phe Leu Thr Met Leu Gly Pro Ser Pro Asp
305                 310                 315                 320
```

-continued

```
Trp Asn Val Gly Leu Ser Ala Glu Asp Leu Cys Thr Lys Asp Cys Gly
                325                 330                 335

Trp Val Gln Lys Val Val Gln Asp Leu Ile Pro Trp Asp Ala Gly Thr
            340                 345                 350

Asp Ser Gly Val Thr Tyr Glu Ser Pro Asn Lys Pro Thr Val Pro Gln
        355                 360                 365

Glu Lys Ile Arg Pro Leu Thr Ser Leu Asp His Pro Gln Ser Pro Phe
    370                 375                 380

Tyr Asp Pro Glu Gly Gly Ser Ile Lys Leu Val Ala Arg Val Val Leu
385                 390                 395                 400

Glu Arg Ile Ala Arg Lys Gly Glu Gln Cys Asn Phe Val Pro Asp Asn
                405                 410                 415

Ile Asp Asp Ile Val Ala Asp Leu Ala Pro Glu Glu Lys Glu Asp
            420                 425                 430

Asp Thr Pro Glu Thr Cys Ile Tyr Ser Asn Trp Ser Pro Trp Ser Ala
        435                 440                 445

Cys Ser Ser Ser Thr Cys Glu Lys Gly Lys Arg Met Arg Gln Arg Met
    450                 455                 460

Leu Lys Ala Gln Leu Asp Leu Ser Val Pro Cys Pro Asp Thr Gln Asp
465                 470                 475                 480

Phe Gln Pro Cys Met Gly Pro Gly Cys Ser Asp Glu Asp Gly Ser Thr
                485                 490                 495

Cys Met Met Ser Asp Trp Ile Thr Trp Ser Pro Cys Ser Val Ser Cys
            500                 505                 510

Gly Met Gly Thr Arg Ser Arg Glu Arg Tyr Val Lys Gln Phe Pro Glu
        515                 520                 525

Asp Gly Ser Met Cys Lys Val Pro Thr Glu Glu Thr Glu Lys Cys Ile
    530                 535                 540

Val Asn Glu Glu Cys Ser Pro Ser Ser Cys Leu Val Thr Glu Trp Gly
545                 550                 555                 560

Glu Trp Asp Glu Cys Ser Ala Ser Cys Gly Thr Gly Met Lys Arg Arg
                565                 570                 575

His Arg Met Ile Lys Met Thr Pro Ala Asp Gly Ser Met Cys Lys Ala
            580                 585                 590

Glu Thr Thr Glu Ala Glu Lys Cys Met Met Pro Glu Cys His Thr Ile
        595                 600                 605

Pro Cys Leu Leu Ser Pro Trp Ser Glu Trp Ser Asp Cys Ser Val Thr
    610                 615                 620

Cys Gly Lys Gly Met Arg Thr Arg Gln Arg Met Leu Lys Ser Ala Ala
625                 630                 635                 640

Glu Leu Gly Asp Cys Asn Glu Glu Leu Glu Gln Ala Glu Lys Cys Met
                645                 650                 655

Leu Pro Glu Cys Pro Ile Asp Cys Glu Leu Thr Glu Trp Ser Gln Trp
            660                 665                 670

Ser Glu Cys Asn Thr Ser Cys Gly Lys Gly His Met Ile Arg Thr Arg
        675                 680                 685

Met Ile Lys Ile Glu Pro Gln Phe Gly Gly Thr Ala Cys Pro Glu Thr
    690                 695                 700

Val Gln Arg Thr Lys Cys Arg Val Arg Lys Cys Leu Arg Gly Pro Gly
705                 710                 715                 720

Met Glu Lys Arg Arg Trp Lys Glu Ala Arg Glu Lys Arg Arg Ser Glu
                725                 730                 735

Gln Ala Lys Lys Asn Ile Asp Asn Glu Gln Tyr Pro Val Cys Arg Leu
            740                 745                 750
```

5,750,502

-continued

```
Lys Pro Trp Thr Ala Trp Thr Glu Cys Ser Thr Leu Cys Gly Gly Gly
        755                 760                 765
Ile Gln Glu Arg Tyr Met Met Val Lys Lys Arg Ser Lys Ser Thr Gln
        770                 775                 780
Phe Thr Ser Cys Lys Asp Lys Lys Glu Leu Arg Ala Cys Asn Val His
785                 790                 795                 800
Pro Cys
```

( 2 ) INFORMATION FOR SEQ ID NO:13:

( i ) SEQUENCE CHARACTERISTICS:
        ( A ) LENGTH: 1816 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..1705

( x i ) SEQUENCE DESCRIPTION: SEQ ID NO:13:

```
T TCA GGT GAA TAT GTT CTT TGG AGT ATG AGA CAA GCC AGT GAT GGT        46
  Ser Gly Glu Tyr Val Leu Trp Ser Met Arg Gln Ala Ser Asp Gly
  1               5                   10                  15

GTC AAA CAA GTA GCT GAG TTG GGT TCT CCA GTC AAA ATG GAA GAA GAA      94
Val Lys Gln Val Ala Glu Leu Gly Ser Pro Val Lys Met Glu Glu Glu
                  20                  25                  30

ATT CGA CAG AAG GGA GAT GAA GTT CTA ACA GTA ATC AAA GCC AAA GCT     142
Ile Arg Gln Lys Gly Asp Glu Val Leu Thr Val Ile Lys Ala Lys Ala
              35                  40                  45

CAG TGG CCG GCC TGG CAG CCC CTC AAT GTG AGG GCC GCC CCT TCA GCT     190
Gln Trp Pro Ala Trp Gln Pro Leu Asn Val Arg Ala Ala Pro Ser Ala
          50                  55                  60

GAG TTC TCT GTG GAC AGA AGC CGT CAC CTG ATG TCA TTT CTG GCC ATG     238
Glu Phe Ser Val Asp Arg Ser Arg His Leu Met Ser Phe Leu Ala Met
    65                  70                  75

ATG GGT CCT AGC CCA GAC TGG AAT GTA GGA CTC ACC TCC GAG GAT CTC     286
Met Gly Pro Ser Pro Asp Trp Asn Val Gly Leu Thr Ser Glu Asp Leu
80                  85                  90                  95

TGT ACC AAA GAG TGT GGC TGG GTT CAG AAG GTG GTC CAG GAT TTG ATT     334
Cys Thr Lys Glu Cys Gly Trp Val Gln Lys Val Val Gln Asp Leu Ile
                    100                 105                 110

CCA TGG GAT GCA GGC ACT GAC AGT GGG GTA ACC TAC GAG TCT CCA AAC     382
Pro Trp Asp Ala Gly Thr Asp Ser Gly Val Thr Tyr Glu Ser Pro Asn
                115                 120                 125

AAG CCC ACC ATT CCC CAG GAT AAA ATC CGA CCT CTG ACA AGT CTG GAT     430
Lys Pro Thr Ile Pro Gln Asp Lys Ile Arg Pro Leu Thr Ser Leu Asp
            130                 135                 140

CAC CCA CAA AGC CCT TCT ATG ACC AGA GGT GGG CCA ATC ATA CCT ATA     478
His Pro Gln Ser Pro Ser Met Thr Arg Gly Gly Pro Ile Ile Pro Ile
        145                 150                 155

GCT CGA GTT GTG ATT GAA AGG ATT GCC AGG AAG GGA GAA CAG TGC AAT     526
Ala Arg Val Val Ile Glu Arg Ile Ala Arg Lys Gly Glu Gln Cys Asn
160                 165                 170                 175

ATT ATA CCC GAC AAC GTG GAT GAC ATA GTA GCA GAT CTG GTA ACG GAA     574
Ile Ile Pro Asp Asn Val Asp Asp Ile Val Ala Asp Leu Val Thr Glu
                    180                 185                 190

GAG AAA GAC GAA GAT GAT ACC CCG GAG ACC TGC ATA TAT TCC AAC TGG     622
Glu Lys Asp Glu Asp Asp Thr Pro Glu Thr Cys Ile Tyr Ser Asn Trp
                195                 200                 205
```

-continued

| | | | | | | | | | | | | | | | | |
|---|---|---|---|---|---|---|---|---|---|---|---|---|---|---|---|---|
| TCC | CCC | TGG | TCG | GCC | TGC | AGC | TCG | GCC | ACC | TGC | GAC | AAG | GGC | AAG | CGG | 670 |
| Ser | Pro | Trp 210 | Ser | Ala | Cys | Ser | Ser 215 | Ala | Thr | Cys | Asp | Lys 220 | Gly | Lys | Arg | |
| ATG | AGA | CAG | CGC | ATG | TTA | AAG | GCT | CAG | TTA | GAT | CTC | AGT | GTT | CCC | TGC | 718 |
| Met | Arg 225 | Gln | Arg | Met | Leu | Lys 230 | Ala | Gln | Leu | Asp | Leu 235 | Ser | Val | Pro | Cys | |
| CCA | GAC | ACT | CAG | GAC | TTT | GAA | CCC | TGC | ATG | GGG | CCC | GGC | TGC | AGC | GAT | 766 |
| Pro 240 | Asp | Thr | Gln | Asp | Phe 245 | Glu | Pro | Cys | Met | Gly 250 | Pro | Gly | Cys | Ser | Asp 255 | |
| GAC | GAA | GCC | TCT | ACC | TGC | ATG | ATG | TCA | GAA | TGG | ATC | ACC | TGG | TCG | CCG | 814 |
| Asp | Glu | Ala | Ser | Thr 260 | Cys | Met | Met | Ser | Glu 265 | Trp | Ile | Thr | Trp | Ser 270 | Pro | |
| TGC | AGC | GCC | TCC | TGC | GGG | ATG | GGA | ATT | GAG | GTC | AGG | GAG | AGA | TAC | GTC | 862 |
| Cys | Ser | Ala | Ser 275 | Cys | Gly | Met | Gly | Ile 280 | Glu | Val | Arg | Glu | Arg 285 | Tyr | Val | |
| AAG | CAG | TTC | CCA | GAA | GAC | GGT | TCC | TTG | TGT | AAA | GTC | CCA | ACG | GAA | GAA | 910 |
| Lys | Gln | Phe | Pro 290 | Glu | Asp | Gly | Ser | Leu 295 | Cys | Lys | Val | Pro | Thr 300 | Glu | Glu | |
| ACT | GAG | AAA | TGC | ATT | GTC | AAT | GAG | GAG | TGT | GAG | CCA | AGC | AGC | TGT | ATA | 958 |
| Thr | Glu | Lys 305 | Cys | Ile | Val | Asn | Glu 310 | Glu | Cys | Glu | Pro | Ser 315 | Ser | Cys | Ile | |
| GTC | ACG | GAA | TGG | GCA | GAG | TGG | GAG | GAG | TGC | AGC | GCT | ACA | TGC | CGG | ATG | 1006 |
| Val | Thr | Glu | Trp | Ala 325 | Glu | Trp | Glu | Glu | Cys 330 | Ser | Ala | Thr | Cys | Arg 335 | Met | |
| GGT | ATG | AAG | AAG | CGG | CAC | AGG | ATG | ATA | AAG | ATG | ACT | CCA | GCG | GAT | GGA | 1054 |
| Gly | Met | Lys | Lys | Arg 340 | His | Arg | Met | Ile | Lys 345 | Met | Thr | Pro | Ala | Asp 350 | Gly | |
| TCT | ATG | TGC | AAA | GCC | GAC | ACA | ACA | GAG | GTT | GAG | AAA | TGC | ATG | ATG | CCC | 1102 |
| Ser | Met | Cys | Lys 355 | Ala | Asp | Thr | Thr | Glu 360 | Val | Glu | Lys | Cys | Met 365 | Met | Pro | |
| GAA | TGT | CAT | ACC | ATC | CCG | TGC | GTG | TTG | TCC | CCT | TGG | TCT | GAA | TGG | AGT | 1150 |
| Glu | Cys | His 370 | Thr | Ile | Pro | Cys | Val 375 | Leu | Ser | Pro | Trp | Ser 380 | Glu | Trp | Ser | |
| GAT | TGC | AGC | GTT | ACC | TGT | GGC | AAA | GGC | ACC | AGA | ACC | AGA | CAG | AGA | ATG | 1198 |
| Asp | Cys | Ser | Val | Thr 385 | Cys | Gly | Lys | Gly | Thr 390 | Arg | Thr | Arg | Gln | Arg 395 | Met | |
| TTG | AAG | TCC | CCG | TCT | GAA | CTT | GGA | GAT | TGC | AAT | GAG | GAA | CTG | GAA | CTG | 1246 |
| Leu 400 | Lys | Ser | Pro | Ser | Glu 405 | Leu | Gly | Asp | Cys | Asn 410 | Glu | Glu | Leu | Glu | Leu 415 | |
| AAA | CAA | GTG | GAA | AAG | TGC | ATG | CTT | CCT | GAA | TGC | CCT | ATA | AGC | TGT | GAA | 1294 |
| Lys | Gln | Val | Glu | Lys 420 | Cys | Met | Leu | Pro | Glu 425 | Cys | Pro | Ile | Ser | Cys 430 | Glu | |
| TTG | ACA | GAG | TGG | TCT | TAC | TGG | TCT | GAG | TGT | AAC | AAA | TGC | TCG | GGC | AAG | 1342 |
| Leu | Thr | Glu | Trp 435 | Ser | Tyr | Trp | Ser | Glu 440 | Cys | Asn | Lys | Cys | Ser 445 | Gly | Lys | |
| GGT | CAC | ATG | ATT | CGT | ACC | CGA | ATG | ATC | ACA | ATG | GAA | CCA | CAG | TTT | GGA | 1390 |
| Gly | His | Met | Ile 450 | Arg | Thr | Arg | Met | Ile 455 | Thr | Met | Glu | Pro | Gln 460 | Phe | Gly | |
| GGA | GCC | GTC | TGT | CCG | GAA | ACC | GTG | CAA | CGC | AAA | AAA | TGC | CGA | TTA | CGT | 1438 |
| Gly | Ala | Val | Cys 465 | Pro | Glu | Thr | Val 470 | Gln | Arg | Lys | Lys | Cys 475 | Arg | Leu | Arg | |
| AAA | TGT | CAA | AAA | AGT | TCC | GGG | AAT | GAG | CGA | AGG | CAT | TTA | AAG | GAT | GCC | 1486 |
| Lys | Cys | Gln | Lys | Ser 480 | Ser | Gly | Asn | Glu | Arg 485 | Arg | His | Leu | Lys | Asp 490 | Ala 495 | |
| CGA | GAG | AAG | AGA | AGG | AGT | GAA | AAA | ATA | AAG | GAA | GAT | TCA | GAT | GGA | GAA | 1534 |
| Arg | Glu | Lys | Arg | Arg 500 | Ser | Glu | Lys | Ile | Lys 505 | Glu | Asp | Ser | Asp | Gly 510 | Glu | |
| CAG | TAC | CCT | GTA | TGT | AAA | ATG | AAA | CCA | TGG | ACT | GCA | TGG | ACG | GAA | TGT | 1582 |
| Gln | Tyr | Pro | Val 515 | Cys | Lys | Met | Lys | Pro 520 | Trp | Thr | Ala | Trp | Thr 525 | Glu | Cys | |

```
ACC AAA TTC TGC GGT GGC GGG ATA CAA GAG CGG TTC ATG ACT GTG AAG    1630
Thr Lys Phe Cys Gly Gly Gly Ile Gln Glu Arg Phe Met Thr Val Lys
        530                 535                 540

AAG AGA TTC AAA AGT TCT CAG TTC ACC AGC TGC AAG GAC AAG AAG GAG    1678
Lys Arg Phe Lys Ser Ser Gln Phe Thr Ser Cys Lys Asp Lys Lys Glu
545                 550                 555

ATC CGG GCT TGC AAT GTC CAT CCA TGT TAACCTGCCT GAAAAGAGGG          1725
Ile Arg Ala Cys Asn Val His Pro Cys
560                 565

ATTGACACTA CAATCGCAAC AGAAGTCAAT CTTTATTAGA TATTTTTTAT CATAGAATAT  1785

ATACATGTGC TTTCATTTTG CATGTACTTT T                                 1816
```

( 2 ) INFORMATION FOR SEQ ID NO:14:

( i ) SEQUENCE CHARACTERISTICS:
        ( A ) LENGTH: 559 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:14:

```
Met Asn His Leu Gly Asn Val Lys Tyr Leu Val Ile Val Phe Leu Ile
1               5                   10                  15

Phe Phe Asp Leu Phe Leu Val Asn Gly Arg Asp Val Gln Asn Asn Ile
                20                  25                  30

Val Asp Glu Ile Lys Tyr Ser Glu Val Cys Asn Asp Gln Val Asp
            35                  40                  45

Leu Tyr Leu Leu Met Asp Cys Ser Gly Ser Ile Arg Arg His Asn Trp
        50                  55                  60

Val Asn His Ala Val Pro Leu Ala Met Lys Leu Ile Gln Gln Leu Asn
65                  70                  75                  80

Leu Asn Asp Asn Ala Ile His Leu Tyr Val Asn Val Phe Ser Asn Asn
                85                  90                  95

Ala Lys Glu Ile Ile Arg Leu His Ser Asp Ala Ser Lys Asn Lys Glu
                100                 105                 110

Lys Ala Leu Ile Ile Ile Arg Ser Leu Leu Ser Thr Asn Leu Pro Tyr
            115                 120                 125

Gly Arg Thr Asn Leu Thr Asp Ala Leu Leu Gln Val Arg Lys His Leu
        130                 135                 140

Asn Asp Arg Ile Asn Arg Glu Asn Ala Asn Gln Leu Val Val Ile Leu
145                 150                 155                 160

Thr Asp Gly Ile Pro Asp Ser Ile Gln Asp Ser Leu Lys Glu Ser Arg
                165                 170                 175

Lys Leu Ser Asp Arg Gly Val Lys Ile Ala Val Phe Gly Ile Gly Gln
            180                 185                 190

Gly Ile Asn Val Ala Phe Asn Arg Phe Leu Val Gly Cys His Pro Ser
        195                 200                 205

Asp Gly Lys Cys Asn Leu Tyr Ala Asp Ser Ala Trp Glu Asn Val Lys
    210                 215                 220

Asn Val Ile Gly Pro Phe Met Lys Ala Val Cys Val Glu Val Glu Lys
225                 230                 235                 240

Thr Ala Ser Cys Gly Val Trp Asp Glu Trp Ser Pro Cys Ser Val Thr
```

|     |     |     |     |     | 245 |     |     |     |     | 250 |     |     |     |     | 255 |     |     |
| --- | --- | --- | --- | --- | --- | --- | --- | --- | --- | --- | --- | --- | --- | --- | --- | --- | --- |

Cys Gly Lys Gly Thr Arg Ser Arg Lys Arg Glu Ile Leu His Glu Gly
                260                     265                 270

Cys Thr Ser Glu Ile Gln Glu Gln Cys Glu Glu Glu Arg Cys Pro Pro
            275                 280                 285

Lys Trp Glu Pro Leu Asp Val Pro Asp Glu Pro Glu Asp Asp Gln Pro
        290                 295                 300

Arg Pro Arg Gly Asp Asn Ser Ser Val Gln Lys Pro Glu Glu Asn Ile
305                 310                 315                 320

Ile Asp Asn Asn Pro Gln Glu Pro Ser Pro Asn Pro Glu Glu Gly Lys
                325                 330                 335

Asp Glu Asn Pro Asn Gly Phe Asp Leu Asp Glu Asn Pro Glu Asn Pro
            340                 345                 350

Pro Asn Pro Asp Ile Pro Glu Gln Lys Pro Asn Ile Pro Glu Asp Ser
        355                 360                 365

Glu Lys Glu Val Pro Ser Asp Val Pro Lys Asn Pro Glu Asp Asp Arg
    370                 375                 380

Glu Glu Asn Phe Asp Ile Pro Lys Lys Pro Glu Asn Lys His Asp Asn
385                 390                 395                 400

Gln Asn Asn Leu Pro Asn Asp Lys Ser Asp Arg Asn Ile Pro Tyr Ser
                405                 410                 415

Pro Leu Pro Pro Lys Val Leu Asp Asn Glu Arg Lys Gln Ser Asp Pro
            420                 425                 430

Gln Ser Gln Asp Asn Asn Gly Asn Arg His Val Pro Asn Ser Glu Asp
        435                 440                 445

Arg Glu Thr Arg Pro His Gly Arg Asn Asn Glu Asn Arg Ser Tyr Asn
    450                 455                 460

Arg Lys Tyr Asn Asp Thr Pro Lys His Pro Glu Arg Glu Glu His Glu
465                 470                 475                 480

Lys Pro Asp Asn Asn Lys Lys Lys Gly Glu Ser Asp Asn Lys Tyr Lys
                485                 490                 495

Ile Ala Gly Gly Ile Ala Gly Gly Leu Ala Leu Ala Cys Ala Gly
            500                 505                 510

Leu Ala Tyr Lys Phe Val Val Pro Gly Ala Ala Thr Pro Tyr Ala Gly
        515                 520                 525

Glu Pro Ala Pro Phe Asp Glu Thr Leu Gly Glu Glu Asp Lys Asp Leu
    530                 535                 540

Asp Glu Pro Glu Gln Phe Arg Leu Pro Glu Glu Asn Glu Trp Asn
545                 550                 555

( 2 ) INFORMATION FOR SEQ ID NO:15:

( i ) SEQUENCE CHARACTERISTICS:
        ( A ) LENGTH: 469 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:15:

Met Ile Thr Glu Gly Ala Gln Ala Pro Arg Leu Leu Leu Pro Pro Leu
1               5                   10                  15

Leu Leu Leu Leu Thr Leu Pro Ala Thr Gly Ser Asp Pro Val Leu Cys

-continued

```
                    20                      25                      30
Phe  Thr  Gln  Tyr  Glu  Glu  Ser  Ser  Gly  Lys  Cys  Lys  Gly  Leu  Leu  Gly
          35                       40                  45

Gly  Gly  Val  Ser  Val  Glu  Asp  Cys  Cys  Leu  Asn  Thr  Ala  Phe  Ala  Tyr
     50                       55                  60

Gln  Lys  Arg  Ser  Gly  Gly  Leu  Cys  Gln  Pro  Cys  Arg  Ser  Pro  Arg  Trp
65                       70                  75                            80

Ser  Leu  Trp  Ser  Thr  Trp  Ala  Pro  Cys  Ser  Val  Thr  Cys  Ser  Glu  Gly
                    85                  90                       95

Ser  Gln  Leu  Arg  Tyr  Arg  Arg  Cys  Val  Gly  Trp  Asn  Gly  Gln  Cys  Ser
               100                      105                 110

Gly  Lys  Val  Ala  Pro  Gly  Thr  Leu  Glu  Trp  Gln  Leu  Gln  Ala  Cys  Glu
               115                      120                 125

Asp  Gln  Gln  Cys  Cys  Pro  Glu  Met  Gly  Gly  Trp  Ser  Gly  Trp  Gly  Pro
     130                      135                 140

Trp  Glu  Pro  Cys  Ser  Val  Thr  Cys  Ser  Lys  Gly  Thr  Arg  Thr  Arg  Arg
145                      150                      155                      160

Arg  Ala  Cys  Asn  His  Pro  Ala  Pro  Lys  Cys  Gly  Gly  His  Cys  Pro  Gly
                    165                      170                 175

Gln  Ala  Gln  Glu  Ser  Glu  Ala  Cys  Asp  Thr  Gln  Gln  Val  Cys  Pro  Thr
               180                      185                 190

His  Gly  Ala  Trp  Ala  Thr  Trp  Gly  Pro  Trp  Thr  Pro  Cys  Ser  Ala  Ser
          195                      200                 205

Cys  His  Gly  Gly  Pro  His  Glu  Pro  Lys  Glu  Thr  Arg  Ser  Arg  Lys  Cys
     210                      215                 220

Ser  Ala  Pro  Glu  Pro  Ser  Gln  Lys  Pro  Pro  Gly  Lys  Pro  Cys  Pro  Gly
225                      230                      235                      240

Leu  Ala  Tyr  Glu  Gln  Arg  Arg  Cys  Thr  Gly  Leu  Pro  Pro  Cys  Pro  Val
               245                      250                 255

Ala  Gly  Gly  Trp  Gly  Pro  Trp  Gly  Pro  Val  Ser  Pro  Cys  Pro  Val  Thr
               260                      265                 270

Cys  Gly  Leu  Gly  Gln  Thr  Met  Glu  Gln  Arg  Thr  Cys  Asn  His  Pro  Val
     275                      280                 285

Pro  Gln  His  Gly  Gly  Pro  Phe  Cys  Ala  Gly  Asp  Ala  Thr  Arg  Thr  His
     290                      295                 300

Ile  Cys  Asn  Thr  Ala  Val  Pro  Cys  Pro  Val  Asp  Gly  Glu  Trp  Asp  Ser
305                      310                      315                      320

Trp  Gly  Glu  Trp  Ser  Pro  Cys  Ile  Arg  Arg  Asn  Met  Lys  Ser  Ile  Ser
                    325                      330                 335

Cys  Gln  Glu  Ile  Pro  Gly  Gln  Gln  Ser  Arg  Gly  Arg  Thr  Cys  Arg  Gly
               340                      345                 350

Pro  Lys  Phe  Asp  Gly  His  Arg  Cys  Ala  Gly  Gln  Gln  Gln  Asp  Ile  Arg
          355                      360                 365

His  Cys  Tyr  Ser  Ile  Gln  His  Cys  Pro  Leu  Lys  Gly  Ser  Trp  Ser  Glu
     370                      375                 380

Trp  Ser  Thr  Trp  Gly  Leu  Cys  Met  Pro  Pro  Cys  Gly  Pro  Asn  Pro  Thr
385                      390                      395                      400

Arg  Ala  Arg  Gln  Arg  Leu  Cys  Thr  Pro  Leu  Leu  Pro  Lys  Tyr  Pro  Pro
                    405                      410                 415

Thr  Val  Ser  Met  Val  Glu  Gly  Gln  Gly  Glu  Lys  Asn  Val  Thr  Phe  Trp
               420                      425                 430

Gly  Arg  Pro  Leu  Pro  Arg  Cys  Glu  Glu  Leu  Gln  Gly  Gln  Lys  Leu  Val
          435                      440                 445
```

```
        Val  Glu  Glu  Lys  Arg  Pro  Cys  Leu  His  Val  Pro  Ala  Cys  Lys  Asp  Pro
             450                      455                      460

Glu  Glu  Glu  Glu  Leu
             465
```

( 2 ) INFORMATION FOR SEQ ID NO:16:

( i ) SEQUENCE CHARACTERISTICS:
    ( A ) LENGTH: 557 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:16:

```
        Ser  Ala  Cys  Arg  Ser  Phe  Ala  Val  Ala  Ile  Cys  Xaa  Leu  Glu  Ile  Xaa
        1                  5                       10                       15

Ile  Leu  Thr  Ala  Gln  Tyr  Thr  Thr  Ser  Tyr  Asp  Pro  Glu  Leu  Thr  Glu
                       20                       25                       30

Ser  Ser  Gly  Ser  Ala  Ser  His  Ile  Asp  Arg  Arg  Met  Ser  Pro  Trp  Ser
                  35                       40                       45

Glu  Trp  Ser  Gln  Cys  Asp  Pro  Cys  Leu  Arg  Gln  Met  Phe  Arg  Ser  Arg
             50                       55                       60

Ser  Ile  Glu  Val  Phe  Gly  Gln  Phe  Asn  Gly  Lys  Arg  Cys  Thr  Asp  Ala
        65                       70                       75                       80

Val  Gly  Asp  Arg  Arg  Gln  Cys  Val  Pro  Thr  Glu  Pro  Cys  Glu  Asp  Ala
                            85                       90                       95

Glu  Asp  Asp  Cys  Gly  Asn  Asp  Phe  Gln  Cys  Ser  Thr  Gly  Arg  Cys  Ile
                       100                      105                      110

Lys  Met  Arg  Leu  Arg  Cys  Asn  Gly  Asp  Asn  Asp  Cys  Gly  Asp  Phe  Ser
                       115                      120                      125

Asp  Glu  Asp  Asp  Cys  Glu  Ser  Glu  Pro  Arg  Pro  Pro  Cys  Arg  Asp  Arg
             130                      135                      140

Val  Val  Glu  Glu  Ser  Glu  Leu  Ala  Arg  Thr  Ala  Gly  Tyr  Gly  Ile  Asn
        145                      150                      155                      160

Ile  Leu  Gly  Met  Asp  Pro  Leu  Ser  Thr  Pro  Phe  Asp  Asn  Glu  Phe  Tyr
                            165                      170                      175

Asn  Gly  Leu  Cys  Asn  Arg  Asp  Arg  Asp  Gly  Asn  Thr  Leu  Thr  Tyr  Tyr
                       180                      185                      190

Arg  Arg  Pro  Trp  Asn  Val  Ala  Ser  Leu  Ile  Tyr  Glu  Thr  Lys  Gly  Glu
                       195                      200                      205

Lys  Asn  Phe  Arg  Thr  Glu  His  Tyr  Glu  Glu  Gln  Ile  Glu  Ala  Phe  Lys
             210                      215                      220

Ser  Ile  Ile  Gln  Glu  Lys  Thr  Ser  Asn  Phe  Asn  Ala  Ala  Ile  Ser  Leu
        225                      230                      235                      240

Lys  Phe  Thr  Pro  Thr  Glu  Thr  Asn  Lys  Ala  Glu  Gln  Cys  Cys  Glu  Glu
                            245                      250                      255

Thr  Ala  Ser  Ser  Ile  Ser  Leu  His  Gly  Lys  Gly  Ser  Phe  Arg  Phe  Ser
                       260                      265                      270

Tyr  Ser  Lys  Asn  Glu  Thr  Tyr  Gln  Leu  Phe  Leu  Ser  Tyr  Ser  Ser  Lys
                       275                      280                      285

Lys  Glu  Lys  Met  Phe  Leu  His  Val  Lys  Gly  Glu  Ile  His  Leu  Gly  Arg
             290                      295                      300
```

```
Phe  Val  Met  Arg  Asn  Arg  Asp  Val  Leu  Thr  Thr  Thr  Phe  Val  Asp  Asp
305            310                      315                      320

Ile  Lys  Ala  Leu  Pro  Thr  Thr  Tyr  Glu  Lys  Gly  Glu  Tyr  Phe  Ala  Phe
                325                      330                      335

Leu  Glu  Thr  Tyr  Gly  Thr  His  Tyr  Ser  Ser  Ser  Gly  Ser  Leu  Gly  Gly
                340                      345                      350

Leu  Tyr  Glu  Leu  Ile  Tyr  Val  Leu  Asp  Lys  Ala  Ser  Met  Lys  Arg  Lys
          355                      360                      365

Gly  Val  Glu  Leu  Lys  Asp  Ile  Lys  Arg  Cys  Leu  Gly  Tyr  His  Leu  Asp
     370                      375                      380

Val  Ser  Leu  Ala  Phe  Ser  Glu  Ile  Ser  Val  Gly  Ala  Glu  Phe  Asn  Lys
385                      390                      395                      400

Asp  Asp  Cys  Val  Lys  Arg  Gly  Glu  Gly  Arg  Ala  Val  Asn  Ile  Pro  Ser
                405                      410                      415

Glu  Asn  Leu  Ile  Asp  Asp  Val  Val  Ser  Leu  Ile  Arg  Gly  Gly  Thr  Arg
               420                      425                      430

Lys  Tyr  Ala  Phe  Glu  Leu  Lys  Glu  Lys  Leu  Leu  Arg  Gly  Thr  Val  Ile
          435                      440                      445

Asp  Val  Thr  Asp  Phe  Val  Asn  Trp  Ala  Ser  Ser  Ile  Asn  Asp  Ala  Pro
     450                      455                      460

Val  Leu  Ile  Ser  Gln  Lys  Leu  Ser  Pro  Ile  Tyr  Asn  Leu  Val  Pro  Val
465                      470                      475                      480

Lys  Met  Lys  Asn  Ala  His  Leu  Lys  Lys  Gln  Asn  Leu  Glu  Arg  Ala  Ile
                485                      490                      495

Glu  Asp  Tyr  Ile  Asn  Glu  Phe  Ser  Val  Arg  Lys  Cys  His  Thr  Cys  Gln
               500                      505                      510

Asn  Gly  Gly  Thr  Val  Ile  Leu  Met  Asp  Gly  Lys  Cys  Leu  Cys  Ala  Cys
          515                      520                      525

Pro  Phe  Lys  Phe  Glu  Gly  Ile  Ala  Cys  Glu  Ile  Ser  Lys  Gln  Lys  Ile
     530                      535                      540

Ser  Glu  Gly  Leu  Pro  Ala  Leu  Glu  Phe  Pro  Asn  Glu  Lys
545                      550                      555
```

( 2 ) INFORMATION FOR SEQ ID NO:17:

( i ) SEQUENCE CHARACTERISTICS:
        ( A ) LENGTH: 584 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Met  Phe  Ala  Val  Val  Phe  Phe  Ile  Leu  Ser  Leu  Met  Thr  Cys  Gln  Pro
1                    5                        10                       15

Gly  Val  Thr  Ala  Gln  Glu  Lys  Val  Asn  Gln  Arg  Val  Arg  Arg  Ala  Ala
               20                       25                       30

Thr  Pro  Ala  Ala  Val  Thr  Cys  Gln  Leu  Ser  Asn  Trp  Ser  Glu  Trp  Thr
               35                       40                       45

Asp  Cys  Phe  Pro  Cys  Gln  Asp  Lys  Lys  Tyr  Arg  His  Arg  Ser  Leu  Leu
     50                       55                       60

Gln  Pro  Asn  Lys  Phe  Gly  Gly  Thr  Ile  Cys  Ser  Gly  Asp  Ile  Trp  Asp
65                       70                       75                       80

Gln  Ala  Ser  Cys  Ser  Ser  Ser  Thr  Thr  Cys  Val  Arg  Gln  Ala  Gln  Cys
                    85                       90                       95

Gly  Gln  Asp  Phe  Gln  Cys  Lys  Glu  Thr  Gly  Arg  Cys  Leu  Lys  Arg  His
```

```
                          100                    105                    110
Leu  Val  Cys  Asn  Gly  Asp  Gln  Asp  Cys  Leu  Asp  Gly  Ser  Asp  Glu  Asp
               115                    120                    125
Asp  Cys  Glu  Asp  Val  Arg  Ala  Ile  Asp  Glu  Asp  Cys  Ser  Gln  Tyr  Glu
     130                    135                    140
Pro  Ile  Pro  Gly  Ser  Gln  Lys  Ala  Ala  Leu  Gly  Tyr  Asn  Ile  Leu  Thr
145                    150                    155                         160
Gln  Glu  Asp  Ala  Gln  Ser  Val  Tyr  Asp  Ala  Ser  Tyr  Tyr  Gly  Gly  Gln
               165                    170                              175
Cys  Glu  Thr  Val  Tyr  Asn  Gly  Glu  Trp  Arg  Glu  Leu  Arg  Tyr  Asp  Ser
               180                    185                    190
Thr  Cys  Glu  Arg  Leu  Tyr  Tyr  Gly  Asp  Asp  Glu  Lys  Tyr  Phe  Arg  Lys
               195                    200                    205
Pro  Tyr  Asn  Phe  Leu  Lys  Tyr  His  Phe  Glu  Ala  Leu  Ala  Asp  Thr  Gly
     210                    215                    220
Ile  Ser  Ser  Glu  Phe  Tyr  Asp  Asn  Ala  Asn  Asp  Leu  Leu  Ser  Lys  Val
225                    230                    235                         240
Lys  Lys  Asp  Lys  Ser  Asp  Ser  Phe  Gly  Val  Thr  Ile  Gly  Ile  Gly  Pro
               245                    250                              255
Ala  Gly  Ser  Pro  Leu  Leu  Val  Gly  Val  Gly  Val  Ser  His  Ser  Gln  Asp
               260                    265                    270
Thr  Ser  Phe  Leu  Asn  Glu  Leu  Asn  Lys  Tyr  Asn  Glu  Lys  Lys  Phe  Ile
          275                    280                    285
Phe  Thr  Arg  Ile  Phe  Thr  Lys  Val  Gln  Thr  Ala  His  Phe  Lys  Met  Arg
     290                    295                    300
Lys  Asp  Asp  Ile  Met  Leu  Asp  Glu  Gly  Met  Leu  Gln  Ser  Leu  Met  Glu
305                    310                    315                         320
Leu  Pro  Asp  Gln  Tyr  Asn  Tyr  Gly  Met  Tyr  Ala  Lys  Phe  Ile  Asn  Asp
               325                    330                         335
Tyr  Gly  Thr  His  Tyr  Ile  Thr  Ser  Gly  Ser  Met  Gly  Gly  Ile  Tyr  Glu
               340                    345                    350
Tyr  Ile  Leu  Val  Ile  Asp  Lys  Ala  Lys  Met  Glu  Ser  Leu  Gly  Ile  Thr
          355                    360                    365
Ser  Arg  Asp  Ile  Thr  Thr  Cys  Phe  Gly  Gly  Ser  Leu  Gly  Ile  Gln  Tyr
     370                    375                    380
Glu  Asp  Lys  Ile  Asn  Val  Gly  Gly  Gly  Leu  Ser  Gly  Asp  His  Cys  Lys
385                    390                    395                         400
Lys  Phe  Gly  Gly  Gly  Lys  Thr  Glu  Arg  Ala  Arg  Lys  Ala  Met  Ala  Val
               405                    410                    415
Glu  Asp  Ile  Ile  Ser  Arg  Val  Arg  Gly  Gly  Ser  Ser  Gly  Trp  Ser  Gly
               420                    425                    430
Gly  Leu  Ala  Gln  Asn  Arg  Ser  Thr  Ile  Thr  Tyr  Arg  Ser  Trp  Gly  Arg
               435                    440                    445
Ser  Leu  Lys  Tyr  Asn  Pro  Val  Val  Ile  Asp  Phe  Glu  Met  Gln  Pro  Ile
     450                    455                    460
His  Glu  Val  Leu  Arg  His  Thr  Ser  Leu  Gly  Pro  Leu  Glu  Ala  Lys  Arg
465                    470                    475                         480
Gln  Asn  Leu  Arg  Arg  Ala  Leu  Asp  Gln  Tyr  Leu  Met  Glu  Phe  Asn  Ala
               485                    490                         495
Cys  Arg  Cys  Gly  Pro  Cys  Phe  Asn  Asn  Gly  Val  Pro  Ile  Leu  Glu  Gly
               500                    505                    510
Thr  Ser  Cys  Arg  Cys  Gln  Cys  Arg  Leu  Gly  Ser  Leu  Gly  Ala  Ala  Cys
               515                    520                    525
```

```
Glu  Gln  Thr  Gln  Thr  Glu  Gly  Ala  Lys  Ala  Asp  Gly  Ser  Trp  Ser  Cys
     530                 535                      540

Trp  Ser  Ser  Trp  Ser  Val  Cys  Arg  Ala  Gly  Ile  Gln  Glu  Arg  Arg  Arg
545                      550                      555                      560

Glu  Cys  Asp  Asn  Pro  Ala  Pro  Gln  Asn  Gly  Gly  Ala  Ser  Cys  Pro  Gly
                    565                      570                      575

Arg  Lys  Val  Gln  Thr  Gln  Ala  Cys
               580
```

( 2 ) INFORMATION FOR SEQ ID NO:18:

( i ) SEQUENCE CHARACTERISTICS:
       ( A ) LENGTH: 412 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:18:

```
Met  Met  Arg  Lys  Leu  Ala  Ile  Leu  Ser  Val  Ser  Ser  Phe  Leu  Phe  Val
1                   5                        10                      15

Glu  Ala  Leu  Phe  Gln  Glu  Tyr  Gln  Cys  Tyr  Gly  Ser  Ser  Ser  Asn  Thr
               20                  25                            30

Arg  Val  Leu  Asn  Glu  Leu  Asn  Tyr  Asp  Asn  Ala  Gly  Thr  Asn  Leu  Tyr
          35                       40                      45

Asn  Glu  Leu  Glu  Met  Asn  Tyr  Tyr  Gly  Lys  Gln  Glu  Asn  Trp  Tyr  Ser
     50                       55                      60

Leu  Lys  Lys  Asn  Ser  Arg  Ser  Leu  Gly  Glu  Asn  Asp  Asp  Gly  Asn  Asn
65                       70                      75                      80

Asn  Asn  Gly  Asp  Asn  Gly  Arg  Glu  Gly  Lys  Asp  Glu  Asp  Lys  Arg  Asp
               85                       90                      95

Gly  Asn  Asn  Glu  Asp  Asn  Glu  Lys  Leu  Arg  Lys  Pro  Lys  His  Lys  Lys
               100                      105                     110

Leu  Lys  Gln  Pro  Gly  Asp  Gly  Asn  Pro  Asp  Pro  Asn  Ala  Asn  Pro  Asn
          115                      120                     125

Val  Asp  Pro  Asn  Ala  Asn  Pro  Asn  Val  Asp  Pro  Asn  Ala  Asn  Pro  Asn
     130                      135                     140

Val  Asp  Pro  Asn  Ala  Asn  Pro  Asn  Ala  Asn  Pro  Asn  Ala  Asn  Pro  Asn
145                      150                     155                     160

Ala  Asn  Pro  Asn  Ala  Asn  Pro  Asn  Ala  Asn  Pro  Asn  Ala  Asn  Pro  Asn
               165                      170                     175

Ala  Asn  Pro  Asn  Ala  Asn  Pro  Asn  Ala  Asn  Pro  Asn  Ala  Asn  Pro  Asn
               180                      185                     190

Ala  Asn  Pro  Asn  Ala  Asn  Pro  Asn  Ala  Asn  Pro  Asn  Ala  Asn  Pro  Asn
               195                      200                     205

Val  Asp  Pro  Asn  Ala  Asn  Pro  Asn  Ala  Asn  Pro  Asn  Ala  Asn  Pro  Asn
     210                      215                     220

Ala  Asn  Pro  Asn  Ala  Asn  Pro  Asn  Ala  Asn  Pro  Asn  Ala  Asn  Pro  Asn
225                      230                     235                     240

Ala  Asn  Pro  Asn  Ala  Asn  Pro  Asn  Ala  Asn  Pro  Asn  Ala  Asn  Pro  Asn
               245                      250                     255

Ala  Asn  Pro  Asn  Ala  Asn  Pro  Asn  Ala  Asn  Pro  Asn  Ala  Asn  Pro  Asn
               260                      265                     270

Ala  Asn  Pro  Asn  Ala  Asn  Pro  Asn  Ala  Asn  Pro  Asn  Ala  Asn  Pro  Asn
               275                      280                     285

Lys  Asn  Asn  Gln  Gly  Asn  Gly  Gln  Gly  His  Asn  Met  Pro  Asn  Asp  Pro
```

```
                290                        295                        300
Asn  Arg  Asn  Val  Asp  Glu  Asn  Ala  Asn  Ala  Asn  Ala  Val  Lys  Asn
305                      310                      315                      320

Asn  Asn  Asn  Glu  Glu  Pro  Ser  Asp  Lys  His  Ile  Glu  Gln  Tyr  Leu  Lys
                    325                      330                           335

Lys  Ile  Lys  Asn  Ser  Ile  Ser  Thr  Glu  Trp  Ser  Pro  Cys  Ser  Val  Thr
                340                      345                      350

Cys  Gly  Asn  Gly  Ile  Gln  Val  Arg  Ile  Lys  Pro  Gly  Ser  Ala  Asn  Lys
               355                      360                      365

Pro  Lys  Asp  Glu  Leu  Asp  Tyr  Glu  Asn  Asp  Ile  Glu  Lys  Lys  Ile  Cys
     370                      375                      380

Lys  Met  Glu  Lys  Cys  Ser  Ser  Val  Phe  Asn  Val  Val  Asn  Ser  Ser  Ile
385                      390                      395                           400

Gly  Leu  Ile  Met  Val  Leu  Ser  Phe  Leu  Phe  Leu  Asn
                    405                      410
```

( 2 ) INFORMATION FOR SEQ ID NO:19:

( i ) SEQUENCE CHARACTERISTICS:
        ( A ) LENGTH: 1172 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Met  Val  Trp  Arg  Leu  Val  Leu  Leu  Ala  Leu  Trp  Val  Trp  Pro  Ser  Thr
1                   5                        10                       15

Gln  Ala  Gly  His  Gln  Asp  Lys  Asp  Thr  Thr  Phe  Asp  Leu  Phe  Ser  Ile
               20                       25                      30

Ser  Asn  Ile  Asn  Arg  Lys  Thr  Ile  Gly  Ala  Lys  Gln  Phe  Arg  Gly  Pro
               35                       40                      45

Asp  Pro  Gly  Val  Pro  Ala  Tyr  Arg  Phe  Val  Arg  Phe  Asp  Tyr  Ile  Pro
     50                       55                      60

Pro  Val  Asn  Ala  Asp  Asp  Leu  Ser  Lys  Ile  Thr  Lys  Ile  Met  Arg  Gln
65                       70                       75                       80

Lys  Glu  Gly  Phe  Phe  Leu  Thr  Ala  Gln  Leu  Lys  Gln  Asp  Gly  Lys  Ser
               85                       90                      95

Arg  Gly  Thr  Leu  Leu  Ala  Leu  Glu  Gly  Pro  Gly  Leu  Ser  Gln  Arg  Gln
               100                      105                     110

Phe  Glu  Ile  Val  Ser  Asn  Gly  Pro  Ala  Asp  Thr  Leu  Asp  Leu  Thr  Tyr
               115                      120                     125

Trp  Ile  Asp  Gly  Thr  Arg  His  Val  Val  Ser  Leu  Glu  Asp  Val  Gly  Leu
130                      135                      140

Ala  Asp  Ser  Gln  Trp  Lys  Asn  Val  Thr  Val  Gln  Val  Ala  Gly  Glu  Thr
145                      150                      155                      160

Tyr  Ser  Leu  His  Val  Gly  Cys  Asp  Leu  Ile  Gly  Pro  Val  Ala  Leu  Asp
                    165                      170                     175

Glu  Pro  Phe  Tyr  Glu  His  Leu  Gln  Ala  Glu  Lys  Ser  Arg  Met  Tyr  Val
               180                      185                     190

Ala  Lys  Gly  Ser  Ala  Arg  Glu  Ser  His  Phe  Arg  Gly  Leu  Leu  Gln  Asn
          195                      200                     205

Val  His  Leu  Val  Phe  Glu  Asn  Ser  Val  Glu  Asp  Ile  Leu  Ser  Lys  Lys
     210                      215                      220

Gly  Cys  Gln  Gln  Gly  Gln  Gly  Ala  Glu  Ile  Asn  Ala  Ile  Ser  Glu  Asn
225                      230                      235                      240
```

```
Thr Glu Thr Leu Arg Leu Gly Pro His Val Thr Thr Glu Tyr Val Gly
                245             250             255

Pro Ser Ser Glu Arg Arg Pro Glu Val Cys Glu Arg Ser Cys Glu Glu
            260             265             270

Leu Gly Asn Met Val Gln Glu Leu Ser Gly Leu His Val Leu Val Asn
        275             280             285

Gln Leu Ser Glu Asn Leu Lys Arg Val Ser Asn Asp Asn Gln Phe Leu
290             295             300

Trp Glu Leu Ile Gly Gly Pro Pro Lys Thr Arg Asn Met Ser Ala Cys
305             310             315             320

Trp Gln Asp Gly Arg Phe Phe Ala Glu Asn Glu Thr Trp Val Val Asp
                325             330             335

Ser Cys Thr Thr Cys Thr Cys Lys Lys Phe Lys Thr Ile Cys His Gln
            340             345             350

Ile Thr Cys Pro Pro Ala Thr Cys Ala Ser Pro Ser Phe Val Glu Gly
        355             360             365

Glu Cys Cys Pro Ser Cys Leu His Ser Val Asp Gly Glu Glu Gly Trp
370             375             380

Ser Pro Trp Ala Glu Trp Thr Gln Cys Ser Val Thr Cys Gly Ser Gly
385             390             395             400

Thr Gln Gln Arg Gly Arg Ser Cys Asp Val Thr Ser Asn Thr Cys Leu
                405             410             415

Gly Pro Ser Ile Gln Thr Arg Ala Cys Ser Leu Ser Lys Cys Asp Thr
            420             425             430

Arg Ile Arg Gln Asp Gly Gly Trp Ser His Trp Ser Pro Trp Ser Ser
        435             440             445

Cys Ser Val Thr Cys Gly Val Gly Asn Ile Thr Arg Ile Arg Leu Cys
450             455             460

Asn Ser Pro Val Pro Gln Met Gly Gly Lys Asn Cys Lys Gly Ser Gly
465             470             475             480

Arg Glu Thr Lys Ala Cys Gln Gly Ala Pro Cys Pro Ile Asp Gly Arg
                485             490             495

Trp Ser Pro Trp Ser Pro Trp Ser Ala Cys Thr Val Thr Cys Ala Gly
            500             505             510

Gly Ile Arg Glu Arg Thr Arg Val Cys Asn Ser Pro Glu Pro Gln Tyr
        515             520             525

Gly Gly Lys Ala Cys Val Gly Asp Val Gln Glu Arg Gln Met Cys Asn
530             535             540

Lys Arg Ser Cys Pro Val Asp Gly Cys Leu Ser Asn Pro Cys Phe Pro
545             550             555             560

Gly Ala Gln Cys Ser Ser Phe Pro Asp Gly Ser Trp Ser Cys Gly Phe
                565             570             575

Cys Pro Val Gly Phe Leu Gly Asn Gly Thr His Cys Glu Asp Leu Asp
            580             585             590

Glu Cys Ala Leu Val Pro Asp Ile Cys Phe Ser Thr Ser Lys Val Pro
        595             600             605

Arg Cys Val Asn Thr Gln Pro Gly Phe His Cys Leu Pro Cys Pro Pro
610             615             620

Arg Tyr Arg Gly Asn Gln Pro Val Gly Val Gly Leu Glu Ala Ala Lys
625             630             635             640

Thr Glu Lys Gln Val Cys Glu Pro Glu Asn Pro Cys Lys Asp Lys Thr
                645             650             655

His Asn Cys His Lys His Ala Glu Cys Ile Tyr Leu Gly His Phe Ser
```

-continued

|   |   |   | 660 |   |   |   | 665 |   |   |   | 670 |   |   |
|---|---|---|---|---|---|---|---|---|---|---|---|---|---|

Asp Pro Met Tyr Lys Cys Glu Cys Gln Thr Gly Tyr Ala Gly Asp Gly
        675                 680                 685

Leu Ile Cys Gly Glu Asp Ser Asp Leu Asp Gly Trp Pro Asn Leu Asn
        690                 695                 700

Leu Val Cys Ala Thr Asn Ala Thr Tyr His Cys Ile Lys Asp Asn Cys
705                 710                 715                 720

Pro His Leu Pro Asn Ser Gly Gln Glu Asp Phe Asp Lys Asp Gly Ile
                725                 730                 735

Gly Asp Ala Cys Asp Asp Asp Asn Asp Gly Val Thr Asp Glu
        740                 745                 750

Lys Asp Asn Cys Gln Leu Leu Phe Asn Pro Arg Gln Ala Asp Tyr Asp
755                 760                 765

Lys Asp Glu Val Gly Asp Arg Cys Asp Asn Cys Pro Tyr Val His Asn
770                 775                 780

Pro Ala Gln Ile Asp Thr Asp Asn Asn Gly Glu Gly Asp Ala Cys Ser
785                 790                 795                 800

Val Asp Ile Asp Gly Asp Asp Val Phe Asn Glu Arg Asp Asn Cys Pro
                805                 810                 815

Tyr Val Tyr Asn Thr Asp Gln Arg Asp Thr Asp Gly Asp Gly Val Gly
                820                 825                 830

Asp His Cys Asp Asn Cys Pro Leu Val His Asn Pro Asp Gln Thr Asp
        835                 840                 845

Val Asp Asn Asp Leu Val Gly Asp Gln Cys Asp Asn Asn Glu Asp Ile
850                 855                 860

Asp Asp Asp Gly His Gln Asn Asn Gln Asp Asn Cys Pro Tyr Ile Ser
865                 870                 875                 880

Asn Ala Asn Gln Ala Asp His Asp Arg Asp Gly Gln Gly Asp Ala Cys
                885                 890                 895

Asp Pro Asp Asp Asp Asn Asp Gly Val Pro Asp Asp Arg Asp Asn Cys
                900                 905                 910

Arg Leu Val Phe Asn Pro Asp Gln Glu Asp Leu Asp Gly Asp Gly Arg
        915                 920                 925

Gly Asp Ile Cys Lys Asp Phe Asp Asn Asp Ile Pro Asp Ile
        930                 935                 940

Asp Asp Val Cys Pro Glu Asn Asn Ala Ile Ser Glu Thr Asp Phe Arg
945                 950                 955                 960

Asn Phe Gln Met Val Pro Leu Asp Pro Lys Gly Thr Thr Gln Ile Asp
                965                 970                 975

Pro Asn Trp Val Ile Arg His Gln Gly Lys Glu Leu Val Gln Thr Ala
                980                 985                 990

Asn Ser Asp Pro Gly Ile Ala Val Gly Phe Asp Glu Phe Gly Ser Val
        995                 1000                1005

Asp Phe Ser Gly Thr Phe Tyr Val Asn Thr Asp Arg Asp Asp Asp Tyr
        1010                1015                1020

Ala Gly Phe Val Phe Gly Tyr Gln Ser Ser Ser Arg Phe Tyr Val Val
1025                1030                1035                1040

Met Trp Lys Gln Val Thr Gln Thr Tyr Trp Glu Asp Gln Pro Thr Arg
                1045                1050                1055

Ala Tyr Gly Tyr Ser Gly Val Ser Leu Lys Val Val Asn Ser Thr Thr
                1060                1065                1070

Gly Thr Gly Glu His Leu Arg Asn Ala Leu Trp His Thr Gly Asn Thr
        1075                1080                1085

Pro Gly Gln Val Arg Thr Leu Trp His Asp Pro Arg Asn Ile Gly Trp
    1090                1095                1100

Lys Asp Tyr Thr Ala Tyr Arg Trp His Leu Thr His Arg Pro Lys Thr
1105                1110                1115                1120

Gly Tyr Ile Arg Val Leu Val His Glu Gly Lys Gln Val Met Ala Asp
                1125                1130                1135

Ser Gly Pro Ile Tyr Asp Gln Thr Tyr Ala Gly Gly Arg Leu Gly Leu
            1140                1145                1150

Phe Val Phe Ser Gln Glu Met Val Tyr Phe Ser Asp Leu Lys Tyr Glu
            1155                1160                1165

Cys Arg Asp Ile
        1170

(2) INFORMATION FOR SEQ ID NO:20:

(i) SEQUENCE CHARACTERISTICS:
   (A) LENGTH: 1170 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:20:

Met Gly Leu Ala Trp Gly Leu Gly Val Leu Phe Leu Met His Val Cys
1                5               10                15

Gly Thr Asn Arg Ile Pro Glu Ser Gly Asp Asn Ser Val Phe Asp
            20              25              30

Ile Phe Glu Leu Thr Gly Ala Ala Arg Lys Gly Ser Gly Arg Arg Leu
        35              40              45

Val Lys Gly Pro Asp Pro Ser Ser Pro Ala Phe Arg Ile Glu Asp Ala
    50              55              60

Asn Leu Ile Pro Pro Val Pro Asp Asp Lys Phe Gln Asp Leu Val Asp
65              70              75              80

Ala Val Arg Thr Glu Lys Gly Phe Leu Leu Leu Ala Ser Leu Arg Gln
            85              90              95

Met Lys Lys Thr Arg Gly Thr Leu Leu Ala Leu Glu Arg Lys Asp His
            100             105             110

Ser Gly Gln Val Phe Ser Val Val Ser Asn Gly Lys Ala Gly Thr Leu
            115             120             125

Asp Leu Ser Leu Thr Val Gln Gly Lys Gln His Val Val Ser Val Glu
    130             135             140

Glu Ala Leu Leu Ala Thr Gly Gln Trp Lys Ser Ile Thr Leu Phe Val
145             150             155             160

Gln Glu Asp Arg Ala Gln Leu Tyr Ile Asp Cys Glu Lys Met Glu Asn
            165             170             175

Ala Glu Leu Asp Val Pro Ile Gln Ser Val Phe Thr Arg Asp Leu Ala
            180             185             190

Ser Ile Ala Arg Leu Arg Ile Ala Lys Gly Gly Val Asn Asp Asn Phe
        195             200             205

Gln Gly Val Leu Gln Asn Val Arg Phe Val Phe Gly Thr Thr Pro Glu
    210             215             220

Asp Ile Leu Arg Asn Lys Gly Cys Ser Ser Ser Thr Ser Val Leu Leu
225             230             235             240

Thr Leu Asp Asn Asn Val Val Asn Gly Ser Ser Pro Ala Ile Arg Thr
            245             250             255

Asn Tyr Ile Gly His Lys Thr Lys Asp Leu Gln Ala Ile Cys Gly Ile

|     |     |     |     |     |     |     |     |     |     |     |     |     |     |
|-----|-----|-----|-----|-----|-----|-----|-----|-----|-----|-----|-----|-----|-----|
|     |     |     |     | 260 |     |     |     | 265 |     |     |     | 270 |     |
| Ser | Cys | Asp | Glu | Leu | Ser | Ser | Met | Val | Leu | Glu | Leu | Arg | Gly | Leu | Arg |
|     |     | 275 |     |     |     |     | 280 |     |     |     | 285 |     |     |
| Thr | Ile | Val | Thr | Thr | Leu | Gln | Asp | Ser | Ile | Arg | Lys | Val | Thr | Glu | Glu |
|     | 290 |     |     |     |     | 295 |     |     |     |     | 300 |     |     |
| Asn | Lys | Glu | Leu | Ala | Asn | Glu | Leu | Arg | Arg | Pro | Pro | Leu | Cys | Tyr | His |
| 305 |     |     |     |     | 310 |     |     |     |     | 315 |     |     |     |     | 320 |
| Asn | Gly | Val | Gln | Tyr | Arg | Asn | Asn | Glu | Glu | Trp | Thr | Val | Asp | Ser | Cys |
|     |     |     |     | 325 |     |     |     |     | 330 |     |     |     |     | 335 |
| Thr | Glu | Cys | His | Cys | Gln | Asn | Ser | Val | Thr | Ile | Cys | Lys | Lys | Val | Ser |
|     |     |     | 340 |     |     |     |     | 345 |     |     |     |     | 350 |     |
| Cys | Pro | Ile | Met | Pro | Cys | Ser | Asn | Ala | Thr | Val | Pro | Asp | Gly | Glu | Cys |
|     |     | 355 |     |     |     |     | 360 |     |     |     |     | 365 |     |     |
| Cys | Pro | Arg | Cys | Trp | Pro | Ser | Asp | Ser | Ala | Asp | Asp | Gly | Trp | Ser | Pro |
|     | 370 |     |     |     |     | 375 |     |     |     |     | 380 |     |     |     |
| Trp | Ser | Glu | Trp | Thr | Ser | Cys | Ser | Thr | Ser | Cys | Gly | Asn | Gly | Ile | Gln |
| 385 |     |     |     |     | 390 |     |     |     |     | 395 |     |     |     |     | 400 |
| Gln | Arg | Gly | Arg | Ser | Cys | Asp | Ser | Leu | Asn | Asn | Arg | Cys | Glu | Gly | Ser |
|     |     |     |     | 405 |     |     |     |     | 410 |     |     |     |     | 415 |
| Ser | Val | Gln | Thr | Arg | Thr | Cys | His | Ile | Gln | Glu | Cys | Asp | Lys | Arg | Phe |
|     |     |     | 420 |     |     |     |     | 425 |     |     |     |     | 430 |     |
| Lys | Gln | Asp | Gly | Gly | Trp | Ser | His | Trp | Ser | Pro | Trp | Ser | Ser | Cys | Ser |
|     |     |     | 435 |     |     |     |     | 440 |     |     |     |     | 445 |     |
| Val | Thr | Cys | Gly | Asp | Gly | Val | Ile | Thr | Arg | Ile | Arg | Leu | Cys | Asn | Ser |
|     |     |     | 450 |     |     |     |     | 455 |     |     |     |     | 460 |     |
| Pro | Ser | Pro | Gln | Met | Asn | Gly | Lys | Pro | Cys | Glu | Gly | Glu | Ala | Arg | Glu |
| 465 |     |     |     |     | 470 |     |     |     |     | 475 |     |     |     |     | 480 |
| Thr | Lys | Ala | Cys | Lys | Lys | Asp | Ala | Cys | Pro | Ile | Asn | Gly | Gly | Trp | Gly |
|     |     |     |     | 485 |     |     |     |     | 490 |     |     |     |     | 495 |
| Pro | Trp | Ser | Pro | Trp | Asp | Ile | Cys | Ser | Val | Thr | Cys | Gly | Gly | Gly | Val |
|     |     |     | 500 |     |     |     |     | 505 |     |     |     |     | 510 |     |
| Gln | Lys | Arg | Ser | Arg | Leu | Cys | Asn | Asn | Pro | Thr | Pro | Gln | Phe | Gly | Gly |
|     |     |     | 515 |     |     |     |     | 520 |     |     |     |     | 525 |     |
| Lys | Asp | Cys | Val | Gly | Asp | Val | Thr | Glu | Asn | Gln | Ile | Cys | Asn | Lys | Gln |
|     | 530 |     |     |     |     | 535 |     |     |     |     | 540 |     |     |     |
| Asp | Cys | Pro | Ile | Asp | Gly | Cys | Leu | Ser | Asn | Pro | Cys | Phe | Ala | Gly | Val |
| 545 |     |     |     |     | 550 |     |     |     |     | 555 |     |     |     |     | 560 |
| Lys | Cys | Thr | Ser | Tyr | Pro | Asp | Gly | Ser | Trp | Lys | Cys | Gly | Ala | Cys | Pro |
|     |     |     |     | 565 |     |     |     |     | 570 |     |     |     |     | 575 |
| Pro | Gly | Tyr | Ser | Gly | Asn | Gly | Ile | Gln | Cys | Thr | Asp | Val | Asp | Glu | Cys |
|     |     |     | 580 |     |     |     |     | 585 |     |     |     |     | 590 |     |
| Lys | Glu | Val | Pro | Asp | Ala | Cys | Phe | Asn | His | Asn | Gly | Glu | His | Arg | Cys |
|     |     |     | 595 |     |     |     |     | 600 |     |     |     |     | 605 |     |
| Glu | Asn | Thr | Asp | Pro | Gly | Tyr | Asn | Cys | Leu | Pro | Cys | Pro | Pro | Arg | Phe |
|     | 610 |     |     |     |     | 615 |     |     |     |     | 620 |     |     |     |
| Thr | Gly | Ser | Gln | Pro | Phe | Gly | Gln | Gly | Val | Glu | His | Ala | Thr | Ala | Asn |
| 625 |     |     |     |     | 630 |     |     |     |     | 635 |     |     |     |     | 640 |
| Lys | Gln | Val | Cys | Lys | Pro | Arg | Asn | Pro | Cys | Thr | Asp | Gly | Thr | His | Asp |
|     |     |     |     | 645 |     |     |     |     | 650 |     |     |     |     | 655 |
| Cys | Asn | Lys | Asn | Ala | Lys | Cys | Asn | Tyr | Leu | Gly | His | Tyr | Ser | Asp | Pro |
|     |     |     | 660 |     |     |     |     | 665 |     |     |     |     | 670 |     |
| Met | Tyr | Arg | Cys | Glu | Cys | Lys | Pro | Gly | Tyr | Ala | Gly | Asn | Gly | Ile | Ile |
|     |     | 675 |     |     |     |     | 680 |     |     |     |     | 685 |     |     |

-continued

| | | | | | | | | | | | | | | |
|---|---|---|---|---|---|---|---|---|---|---|---|---|---|---|
| Cys | Gly | Glu | Asp | Thr | Asp | Leu | Asp | Gly | Trp | Pro | Asn | Glu | Asn | Leu | Val |
| | 690 | | | | 695 | | | | 700 | | | | | |
| Cys | Val | Ala | Asn | Ala | Thr | Tyr | His | Cys | Lys | Lys | Asp | Asn | Cys | Pro | Asn |
| 705 | | | | | 710 | | | | 715 | | | | | | 720 |
| Leu | Pro | Asn | Ser | Gly | Gln | Glu | Asp | Tyr | Asp | Lys | Asp | Gly | Ile | Gly | Asp |
| | | | | 725 | | | | | 730 | | | | | 735 | |
| Ala | Cys | Asp | Asp | Asp | Asp | Asn | Asp | Lys | Ile | Pro | Asp | Asp | Arg | Asp |
| | | | 740 | | | | | 745 | | | | 750 | | |
| Asn | Cys | Pro | Phe | His | Tyr | Asn | Pro | Ala | Gln | Tyr | Asp | Tyr | Asp | Arg | Asp |
| | | 755 | | | | | 760 | | | | | 765 | | | |
| Asp | Val | Gly | Asp | Arg | Cys | Asp | Asn | Cys | Pro | Tyr | Asn | His | Asn | Pro | Asp |
| | 770 | | | | | 775 | | | | | 780 | | | | |
| Gln | Ala | Asp | Thr | Asp | Asn | Asn | Gly | Glu | Gly | Asp | Ala | Cys | Ala | Ala | Asp |
| 785 | | | | | 790 | | | | | 795 | | | | | 800 |
| Ile | Asp | Gly | Asp | Gly | Ile | Leu | Asn | Glu | Arg | Asp | Asn | Cys | Gln | Tyr | Val |
| | | | | 805 | | | | | 810 | | | | | 815 | |
| Tyr | Asn | Val | Asp | Gln | Arg | Asp | Thr | Asp | Met | Asp | Gly | Val | Gly | Asp | Gln |
| | | | 820 | | | | | 825 | | | | | 830 | | |
| Cys | Asp | Asn | Cys | Pro | Leu | Glu | His | Asn | Pro | Asp | Gln | Leu | Asp | Ser | Asp |
| | | 835 | | | | | 840 | | | | | 845 | | | |
| Ser | Asp | Arg | Ile | Gly | Asp | Thr | Cys | Asp | Asn | Asn | Gln | Asp | Ile | Asp | Glu |
| | 850 | | | | | 855 | | | | | 860 | | | | |
| Asp | Gly | His | Gln | Asn | Asn | Leu | Asp | Asn | Cys | Pro | Tyr | Val | Pro | Asn | Ala |
| 865 | | | | | 870 | | | | | 875 | | | | | 880 |
| Asn | Gln | Ala | Asp | His | Asp | Lys | Asp | Gly | Lys | Gly | Asp | Ala | Cys | Asp | His |
| | | | | 885 | | | | | 890 | | | | | 895 | |
| Asp | Asp | Asp | Asn | Asp | Gly | Ile | Pro | Asp | Asp | Lys | Asp | Asn | Cys | Arg | Leu |
| | | | 900 | | | | | 905 | | | | | 910 | | |
| Val | Pro | Asn | Pro | Asp | Gln | Lys | Asp | Ser | Asp | Gly | Asp | Gly | Arg | Gly | Asp |
| | | 915 | | | | | 920 | | | | | 925 | | | |
| Ala | Cys | Lys | Asp | Asp | Phe | Asp | His | Asp | Ser | Val | Pro | Asp | Ile | Asp | Asp |
| | 930 | | | | | 935 | | | | | 940 | | | | |
| Ile | Cys | Pro | Glu | Asn | Val | Asp | Ile | Ser | Glu | Thr | Asp | Phe | Arg | Arg | Phe |
| 945 | | | | | 950 | | | | | 955 | | | | | 960 |
| Gln | Met | Ile | Pro | Leu | Asp | Pro | Lys | Gly | Thr | Ser | Gln | Asn | Asp | Pro | Asn |
| | | | | 965 | | | | | 970 | | | | | 975 | |
| Trp | Val | Val | Arg | His | Gln | Gly | Lys | Glu | Leu | Val | Gln | Thr | Val | Asn | Cys |
| | | | 980 | | | | | 985 | | | | | 990 | | |
| Asp | Pro | Gly | Leu | Ala | Val | Gly | Tyr | Asp | Glu | Phe | Asn | Ala | Val | Asp | Phe |
| | | 995 | | | | | 1000 | | | | | 1005 | | | |
| Ser | Gly | Thr | Phe | Phe | Ile | Asn | Thr | Glu | Arg | Asp | Asp | Asp | Tyr | Ala | Gly |
| | | 1010 | | | | | 1015 | | | | | 1020 | | | |
| Phe | Val | Phe | Gly | Tyr | Gln | Ser | Ser | Ser | Arg | Phe | Tyr | Val | Val | Met | Trp |
| 1025 | | | | | 1030 | | | | | 1035 | | | | | 1040 |
| Lys | Gln | Val | Thr | Gln | Ser | Tyr | Trp | Asp | Thr | Asn | Pro | Thr | Arg | Ala | Gln |
| | | | | 1045 | | | | | 1050 | | | | | 1055 | |
| Gly | Tyr | Ser | Gly | Leu | Ser | Val | Lys | Val | Val | Asn | Ser | Thr | Thr | Gly | Pro |
| | | | | 1060 | | | | | 1065 | | | | | 1070 | |
| Gly | Glu | His | Leu | Arg | Asn | Ala | Leu | Trp | His | Thr | Gly | Asn | Thr | Pro | Gly |
| | | | | 1075 | | | | | 1080 | | | | | 1085 | |
| Gln | Val | Arg | Thr | Leu | Trp | His | Asp | Pro | Arg | His | Ile | Gly | Trp | Lys | Asp |
| | | | | 1090 | | | | | 1095 | | | | | 1100 | |
| Phe | Thr | Ala | Tyr | Arg | Trp | Arg | Leu | Ser | His | Arg | Pro | Lys | Thr | Gly | Phe |
| 1105 | | | | | 1110 | | | | | 1115 | | | | | 1120 |

```
Ile Arg Val Val Met Tyr Glu Gly Lys Lys Ile Met Ala Asp Ser Gly
            1125            1130              1135

Pro Ile Tyr Asp Lys Thr Tyr Ala Gly Gly Arg Leu Gly Leu Phe Val
            1140            1145              1150

Phe Ser Gln Glu Met Val Phe Phe Ser Asp Leu Lys Tyr Glu Cys Arg
            1155            1160              1165

Asp Pro
    1170
```